(12) United States Patent
Yeniel et al.

(10) Patent No.: US 12,383,256 B2
(45) Date of Patent: Aug. 12, 2025

(54) SUTURING DEVICE AND METHODS OF USE THEREOF

(71) Applicant: Soranus Arge Ve Danişmanlik Hizmetleri Sanayi Ticaret Anonim Şirketi, Izmir (TR)

(72) Inventors: Ahmet Özgür Yeniel, Izmir (TR); Özgün Selim Germiyan, Izmir (TR); Yetkin Kader, Izmir (TR); Abdullah Alkan, Izmir (TR)

(73) Assignee: Soranus Arge Ve Danismanlik Hizmetleri Sanayi Ticaret Anonim Sirketi, Izmir (TR)

( * ) Notice: Subject to any disclaimer, the term of this patent is extended or adjusted under 35 U.S.C. 154(b) by 0 days.

(21) Appl. No.: 18/605,086

(22) Filed: Mar. 14, 2024

(65) Prior Publication Data

US 2024/0299024 A1 Sep. 12, 2024

Related U.S. Application Data

(63) Continuation of application No. 18/371,975, filed on Sep. 22, 2023, now Pat. No. 11,931,022, which is a
(Continued)

(30) Foreign Application Priority Data

Sep. 7, 2021 (TR) .......................... TR2021/014052
Nov. 10, 2021 (TR) .......................... TR2021/017512

(51) Int. Cl.
*A61B 17/04* (2006.01)
*A61B 17/00* (2006.01)

(52) U.S. Cl.
CPC ...... *A61B 17/0469* (2013.01); *A61B 17/0485* (2013.01); *A61B 2017/00367* (2013.01)

(58) Field of Classification Search
CPC ............ A61B 17/0469; A61B 17/0485; A61B 2017/00367
See application file for complete search history.

(56) References Cited

U.S. PATENT DOCUMENTS 3,587,587 A 6/1971 Raskin
5,284,487 A 2/1994 Hartmeister
(Continued)

FOREIGN PATENT DOCUMENTS

CN 201719295 U 1/2011
DM 218609 1/2022
(Continued)

OTHER PUBLICATIONS

Glazener Cma, Cooper K, Mashayekhi A. Anterior vaginal repair for urinary incontinence in women. Cochrane Database of Systematic Reviews 2017, Issue 7. Art. No. CD001755. DOI: 10.1002/14651858.CD001755.pub2.
(Continued)

*Primary Examiner* — Phong Son H Dang
(74) *Attorney, Agent, or Firm* — Greenberg Traurig, LLP; Roman Fayerberg; David J. Dykeman

(57) ABSTRACT

The present disclosure includes a suturing device including: a fixed arm having a fixed jaw including a first grasping slot configured to receive a needle; a movable arm coupled to a movable jaw including a second grasping slot configured to receive the needle, the movable arm configured to pivot relative to the fixed arm to pivot the movable jaw relative to the fixed jaw until the needle is received in the first grasping slot and the second grasping slot; and a needle transfer mechanism configured to grasp the needle in the first grasping slot or the second grasping slot. In some aspects, the suturing device includes a safety member configured to control when the movable arm moves. The present disclosure includes a loading apparatus including a loading slot
(Continued)

configured to receive a fixed jaw and a slider configured to move the needle towards into the fixed jaw.

19 Claims, 57 Drawing Sheets

Related U.S. Application Data continuation of application No. 18/114,874, filed on Feb. 27, 2023, now Pat. No. 11,903,576, which is a continuation of application No. PCT/TR2022/050959, filed on Sep. 7, 2022.

(56) References Cited

U.S. PATENT DOCUMENTS

| | | | |
|---|---|---|---|
| 5,472,081 A * | 12/1995 | Kilgrow | A61B 17/06133 |
| | | | 206/382 |
| 5,690,652 A | 11/1997 | Wurster | |
| 5,715,942 A * | 2/1998 | Li | A61B 17/04 |
| | | | 206/339 |
| 5,871,488 A | 2/1999 | Tovey | |
| 5,980,538 A | 11/1999 | Fuchs | |
| 6,051,006 A | 4/2000 | Shluzas | |
| 7,615,061 B2 | 11/2009 | White | |
| 8,535,348 B1 | 9/2013 | Alshemari | |
| 8,602,211 B2 * | 12/2013 | Sasur | B65D 85/24 |
| | | | 206/382 |
| 8,628,545 B2 | 1/2014 | Cabrera et al. | |
| 8,821,518 B2 | 9/2014 | Saliman | |
| 8,864,776 B2 | 10/2014 | Bogart et al. | |
| 8,968,340 B2 | 3/2015 | Chowaniec et al. | |
| 9,370,354 B1 * | 6/2016 | Martin | A61B 17/0625 |
| 9,427,228 B2 * | 8/2016 | Hart | A61B 17/06114 |
| 9,782,167 B1 * | 10/2017 | Carne | A61B 17/0625 |
| 9,788,830 B2 * | 10/2017 | Martin | A61B 17/0482 |
| 10,265,063 B1 | 4/2019 | Moses | |
| 10,271,836 B2 | 4/2019 | Marczyk et al. | |
| 10,413,289 B2 | 9/2019 | Cabrera | |
| 10,709,439 B2 | 7/2020 | Malkowski | |
| 10,973,510 B2 | 4/2021 | Malkowski et al. | |
| 11,096,683 B2 | 8/2021 | Marczyk et al. | |
| 11,903,576 B2 | 2/2024 | Yeniel | |
| 11,931,022 B2 | 3/2024 | Yeniel | |
| 2002/0065526 A1 | 5/2002 | Oren | |
| 2002/0138084 A1 | 9/2002 | Weber | |
| 2003/0220658 A1 | 11/2003 | Hatch | |
| 2004/0249394 A1 | 12/2004 | Morris | |
| 2005/0288690 A1 | 12/2005 | Bourque | |
| 2007/0060930 A1 | 3/2007 | Hamilton | |
| 2007/0270885 A1 | 11/2007 | Weinert | |
| 2009/0259233 A1 | 10/2009 | Bogart | |
| 2010/0016866 A1 * | 1/2010 | Meade | A61B 17/06114 |
| | | | 606/139 |
| 2010/0256637 A1 | 10/2010 | Contijoch | |
| 2011/0208237 A1 | 8/2011 | Su | |
| 2012/0283754 A1 | 11/2012 | Murillo | |
| 2013/0274743 A1 | 10/2013 | Banfalvi | |
| 2013/0304096 A1 | 11/2013 | Nguyen | |
| 2014/0107671 A1 | 4/2014 | Lau | |
| 2014/0135821 A1 | 5/2014 | Coleman | |
| 2014/0277109 A1 | 9/2014 | Alshomer | |
| 2017/0056228 A1 | 3/2017 | Saadat | |
| 2017/0071597 A1 | 3/2017 | Gorski | |
| 2017/0340320 A1 | 11/2017 | Baril | |
| 2017/0360431 A1 | 12/2017 | Baril | |
| 2018/0221011 A1 | 8/2018 | Malkowski | |
| 2018/0317904 A1 * | 11/2018 | Malkowski | A61B 17/0625 |
| 2019/0083108 A1 | 3/2019 | Dacosta | |
| 2020/0038012 A1 * | 2/2020 | Nicholas | A61B 17/0625 |
| 2021/0007733 A1 | 1/2021 | Yeniel | |
| 2021/0204934 A1 | 7/2021 | Huntington | |
| 2021/0330317 A1 | 10/2021 | Sartor | |
| 2022/0387020 A1 * | 12/2022 | Luckman | A61B 17/06133 |

FOREIGN PATENT DOCUMENTS

| | | |
|---|---|---|
| EP | 0836427 A1 | 4/1998 |
| EP | 0903109 A1 | 3/1999 |
| WO | 2006128092 A2 | 11/2006 |
| WO | 2017044838 A1 | 3/2017 |
| WO | 2020210437 A1 | 10/2020 |

OTHER PUBLICATIONS

Holdo, B., Long-term clinical outcomes with the retropubic tension-free vaginal tape (TVT) procedure compared to Burch colposuspension for correcting stress urinary incontinence (SUI). Int Urogynecol J 28, 1739-1746 (2017). https://doi.org/10.1007/s00192-017-3345-0.

Sumana Koduri; Transvaginal therapy of genuine stress incontinence; DOI:https://doi.org/10.1016/S0090-4295(00)00509-4; Research Article| vol. 56, Issue 6, Supplement 1, Dec. 23-27, 2000.

Lamblin, G, Van-Nieuwenhuyse, A., Chabert, P. et al. A randomized controlled trial comparing anatomical and functional outcome between vaginal colposuspension and transvaginal mesh. Int Urogynecol J 25, 961-970 (2014). https://doi.org/10.1007/s00192-014-2344-7.

Giacomo Novara; Updated Systematic Review and Meta-Analysis of the Comparative Data on Colposuspensions, Pubovaginal Slings, and Midurethral Tapes in the Surgical Treatment of Female Stress Urinary Incontinence, European Urology, vol. 58, Issue 2, 2010, pp. 218-238, ISSN 0302-2838, https://doi.org/10.1016/j.eururo.2010.04.022. (https://www.sciencedirect.com/science/article/pii/S0302283810003702).

Seracchioli, R., Laparoscopic management of severe ureteral obstruction after vaginal hysterectomy and colposuspension. Int Urogynecol J 29, 1557-1558 (2018). https://doi.org/10.1007/s00192-018-3675-6.

Tuan Shao; Tension-free vaginal tape retropubic sling for recurrent stress urinary incontinence after Burch colposuspension failure; Mar. 24, 2011 https://doi.org/10.1111/j.1442-2042.2011.02755.x.

PCT/TR2022/050959, International Search Report, Date: Dec. 19, 2022, By: Authorized Officer Ruth Boswetter.

URL: https://www.youtube.com/watch?v=XZLulWAGF2U; Date Aug. 29, 2012; By: Andrew Write; Title: "Endostitch load and unload".

https://cordis.europa.eu; "Periodic Report for Period 1;" published on Jul. 14, 2021.

https://cordis.europa.eu; "Vaginal Arco-ColpoSuspension Device for the treatment of Urinary Incontinence in Women," published on Jun. 15, 2020.

* cited by examiner

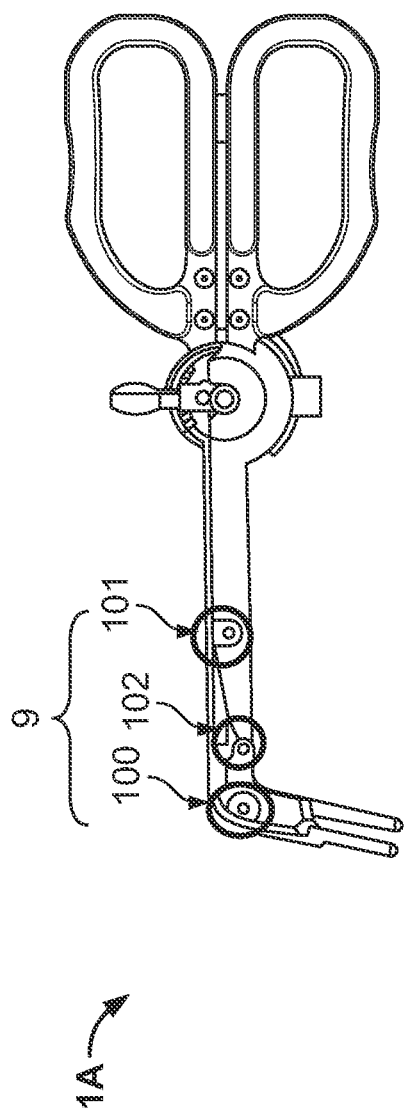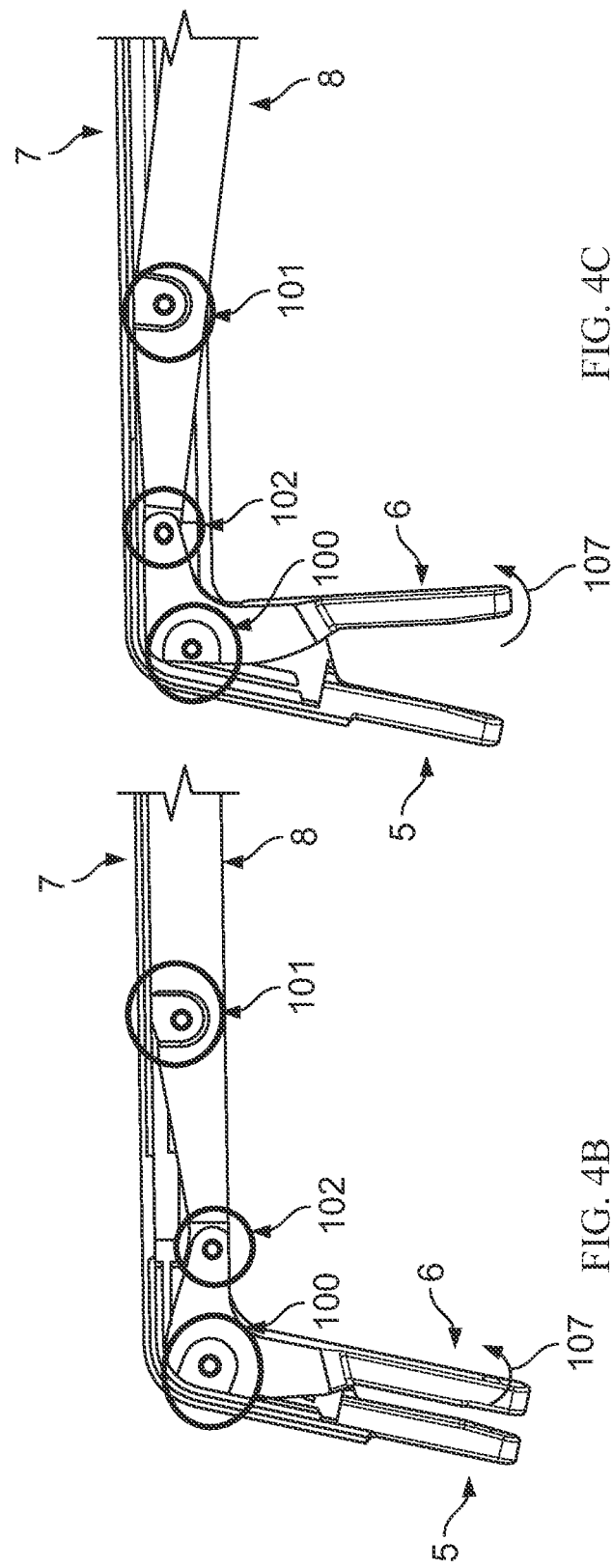

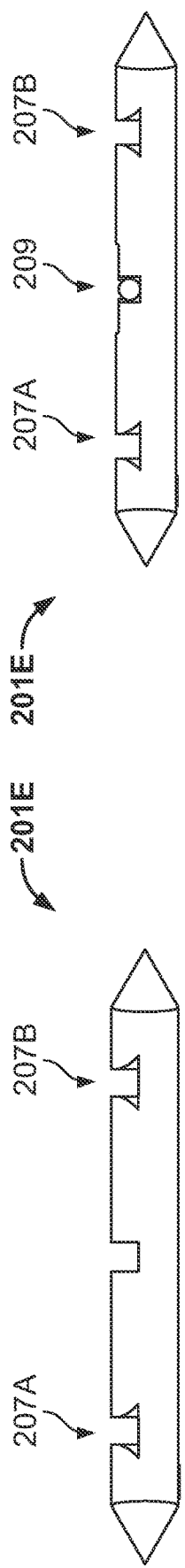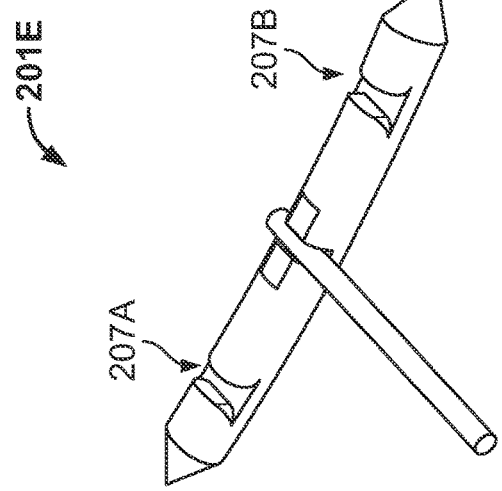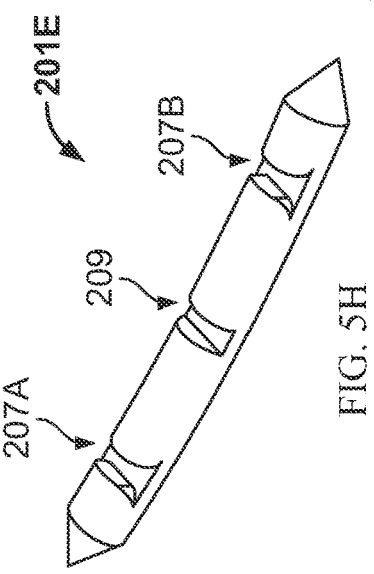

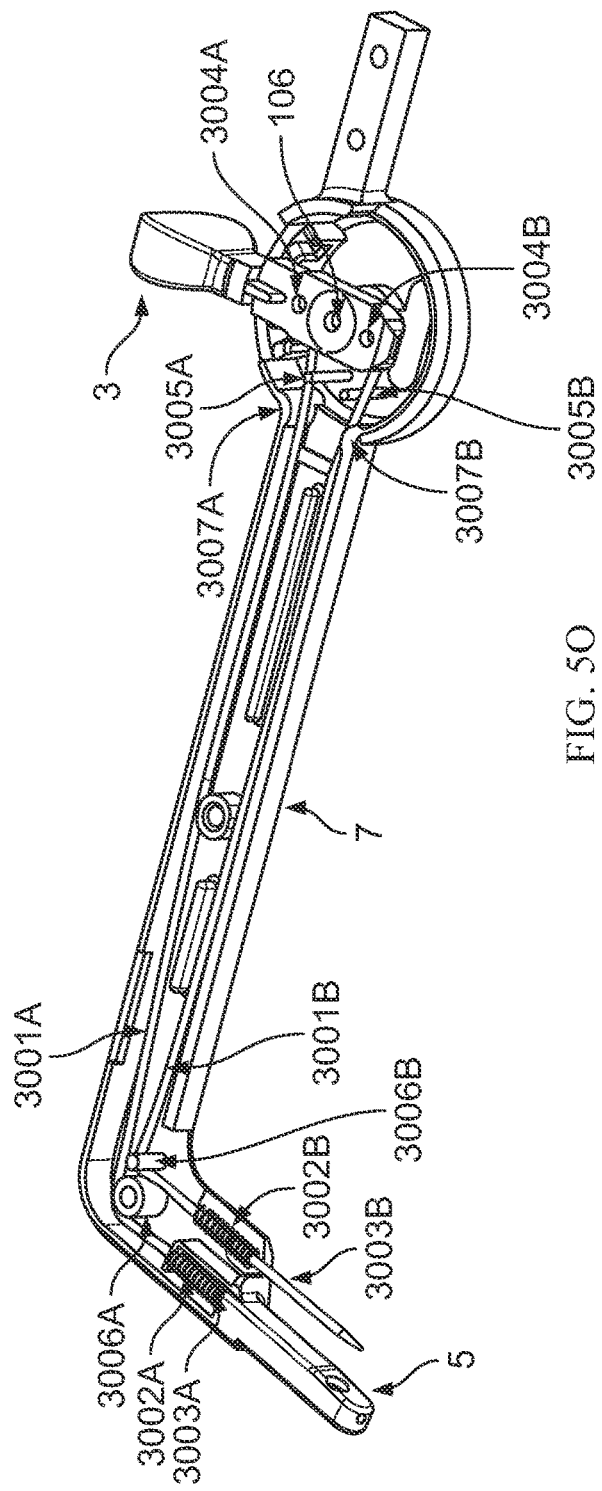
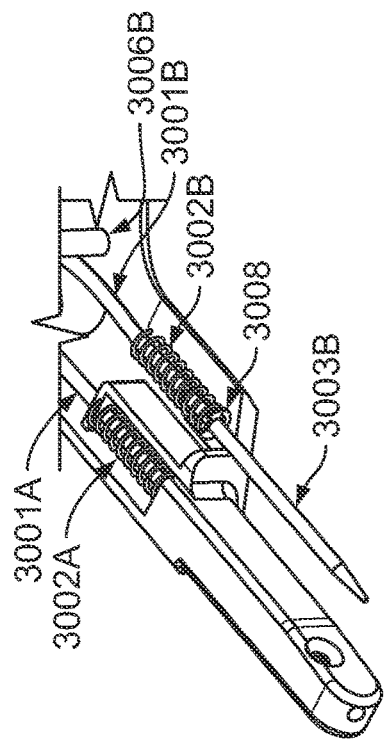
FIG. 5O
FIG. 5P

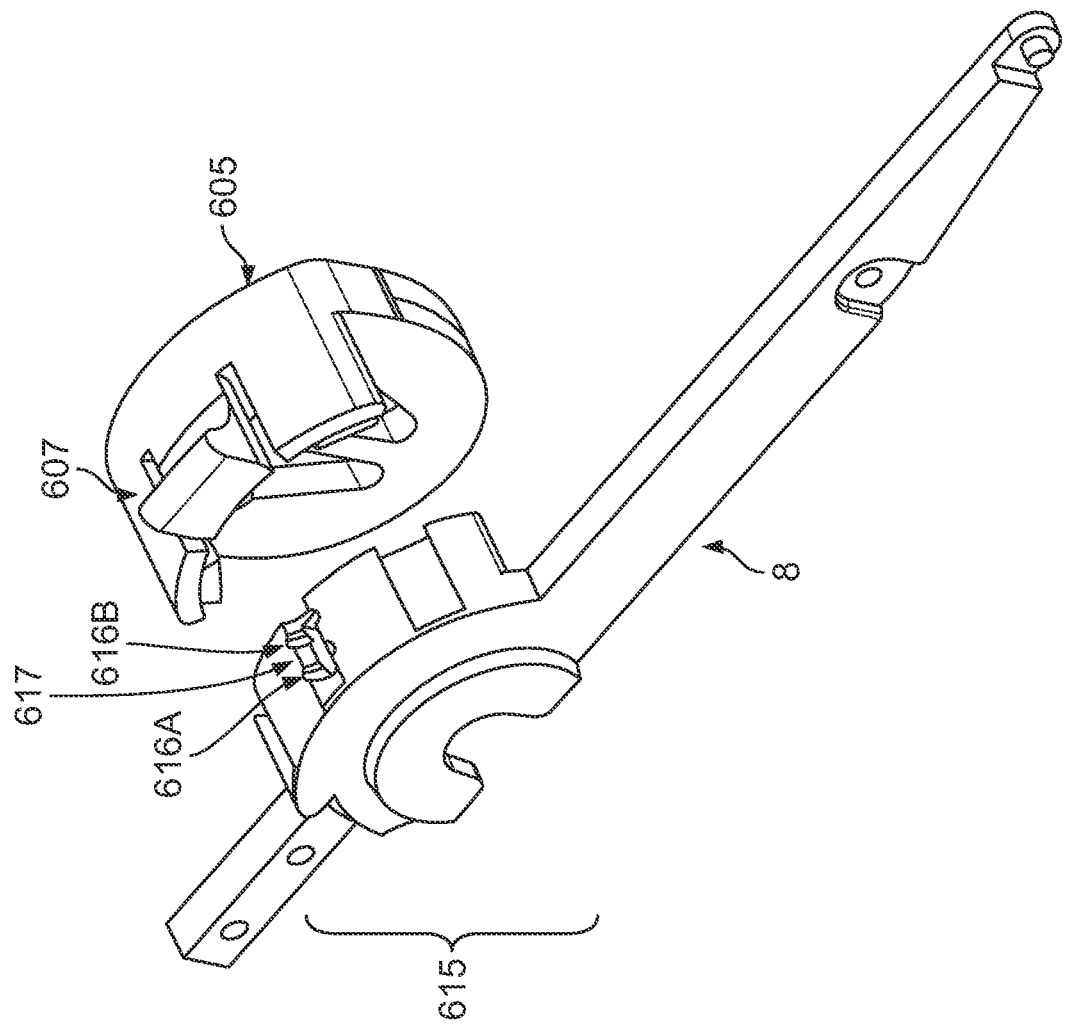
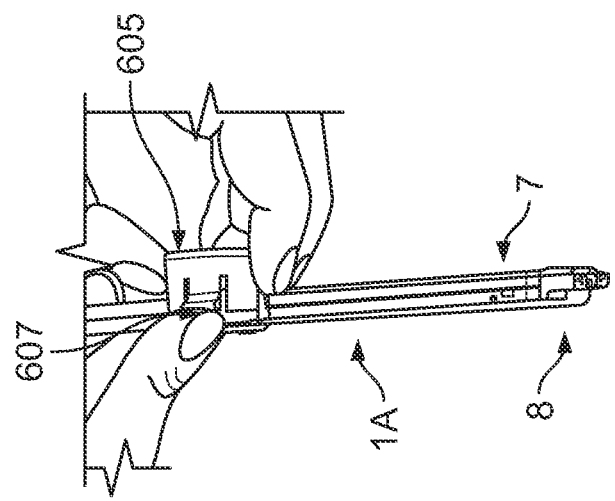
FIG. 9B
FIG. 9A

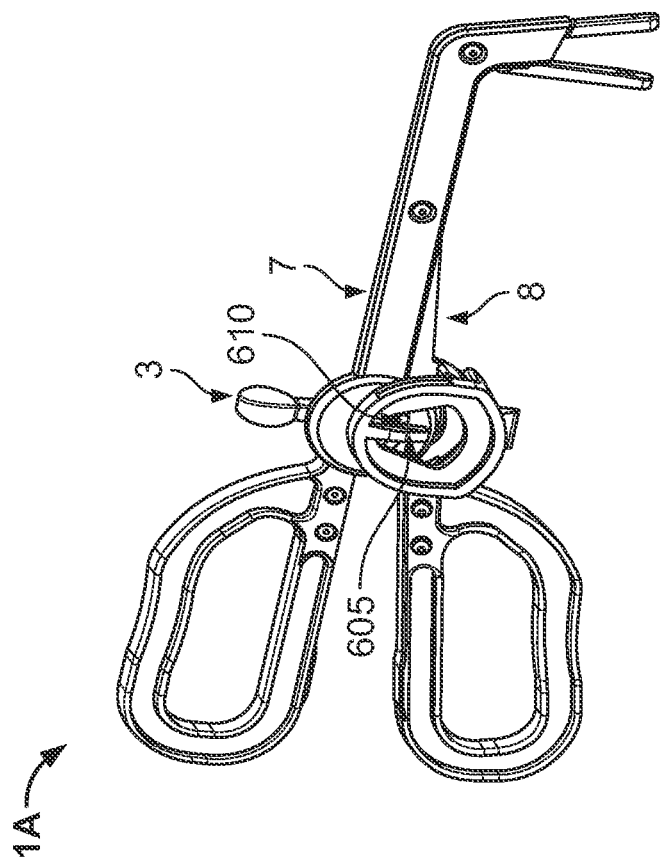
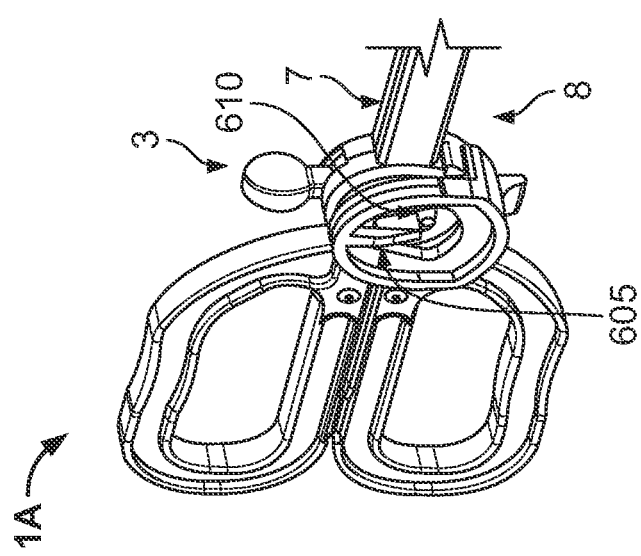
FIG. 10B
FIG. 10A

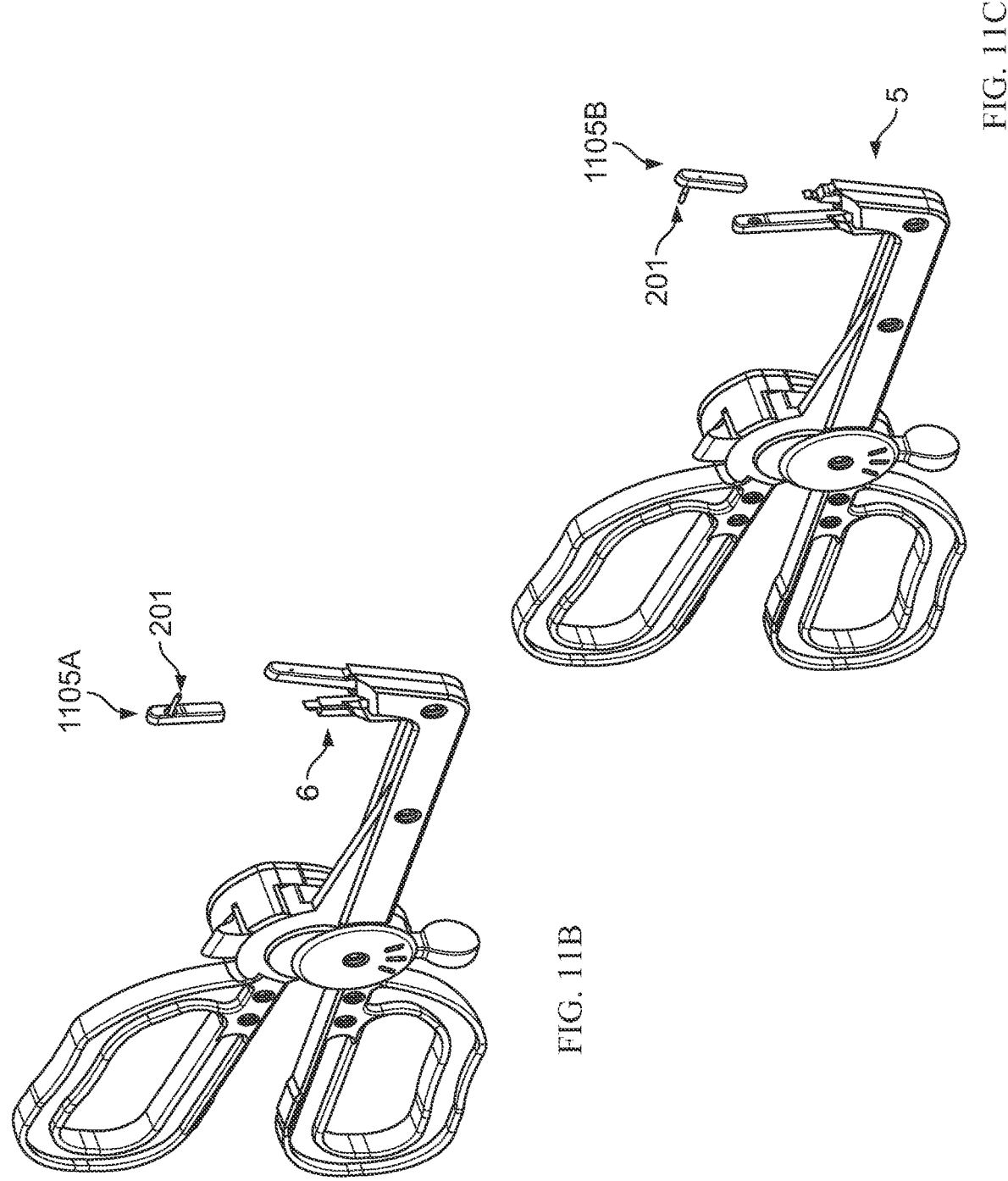

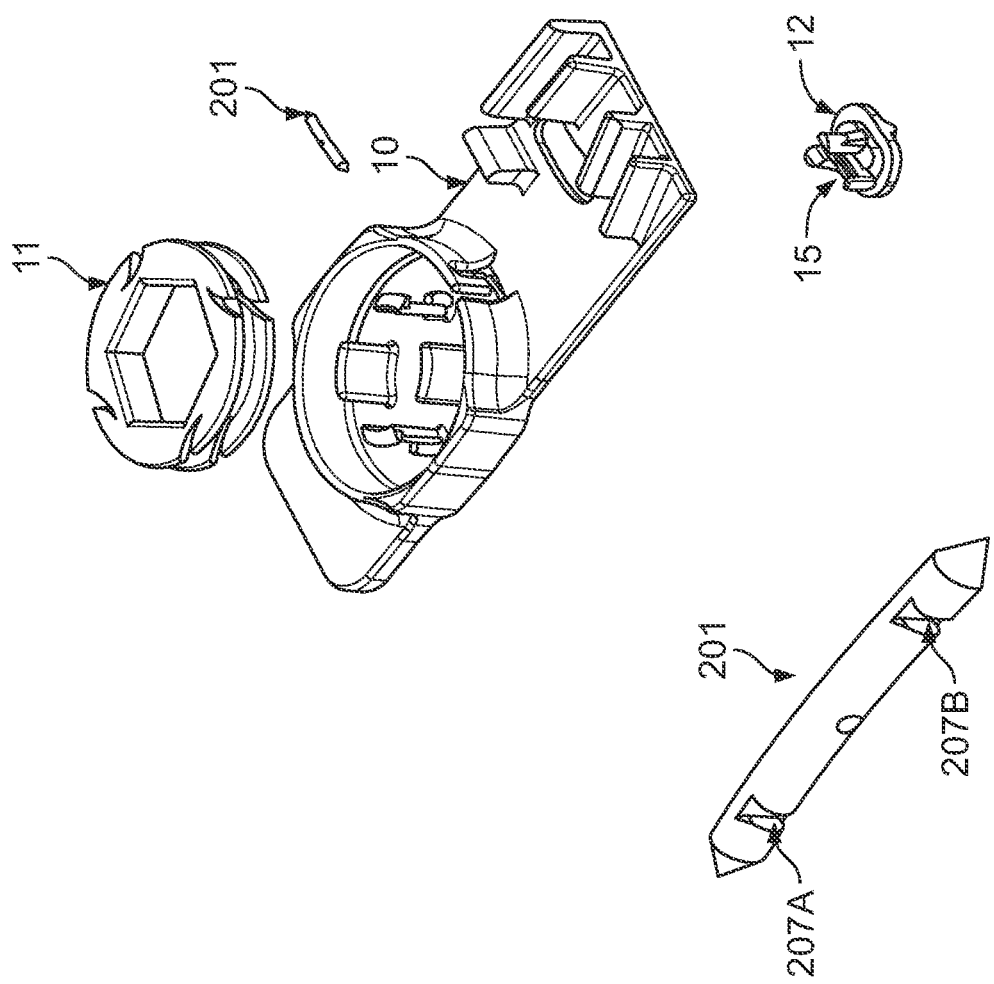
FIG. 14C
FIG. 14B
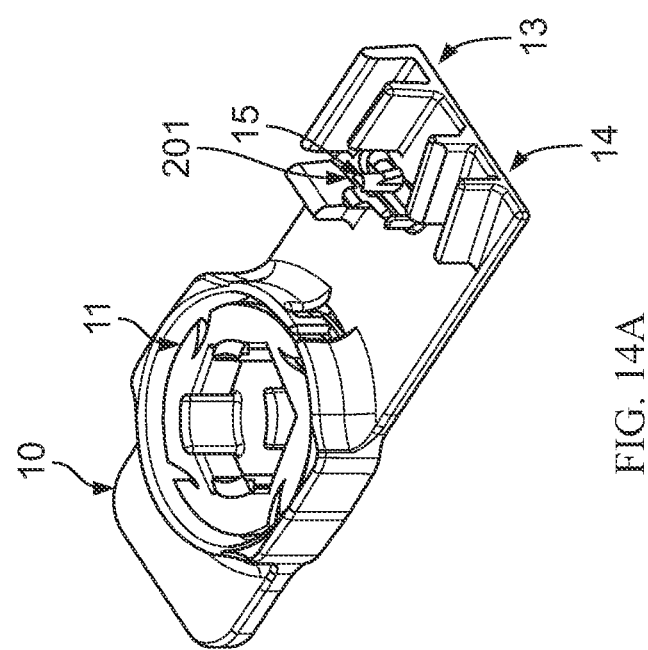
FIG. 14A

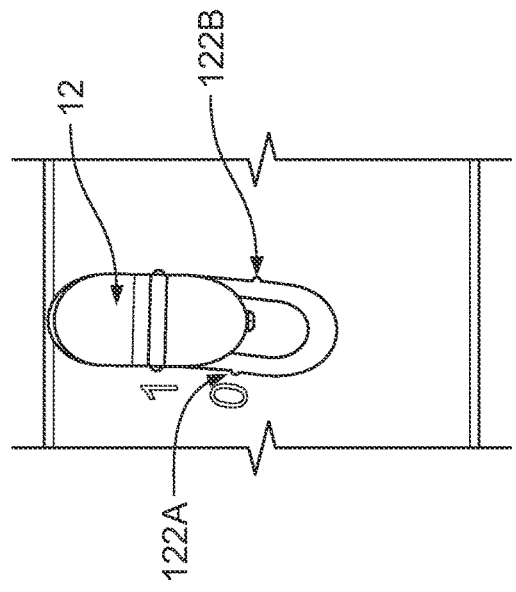
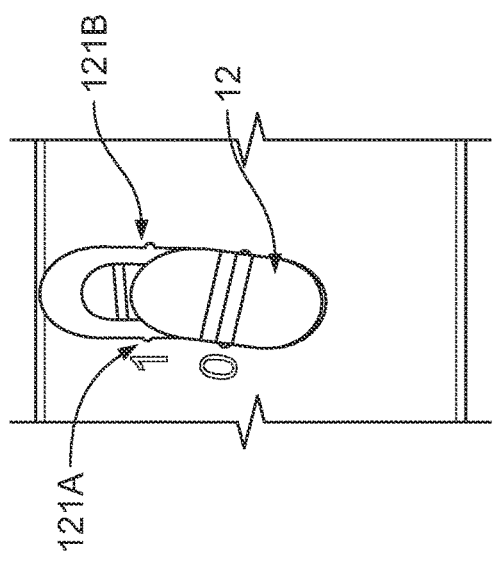
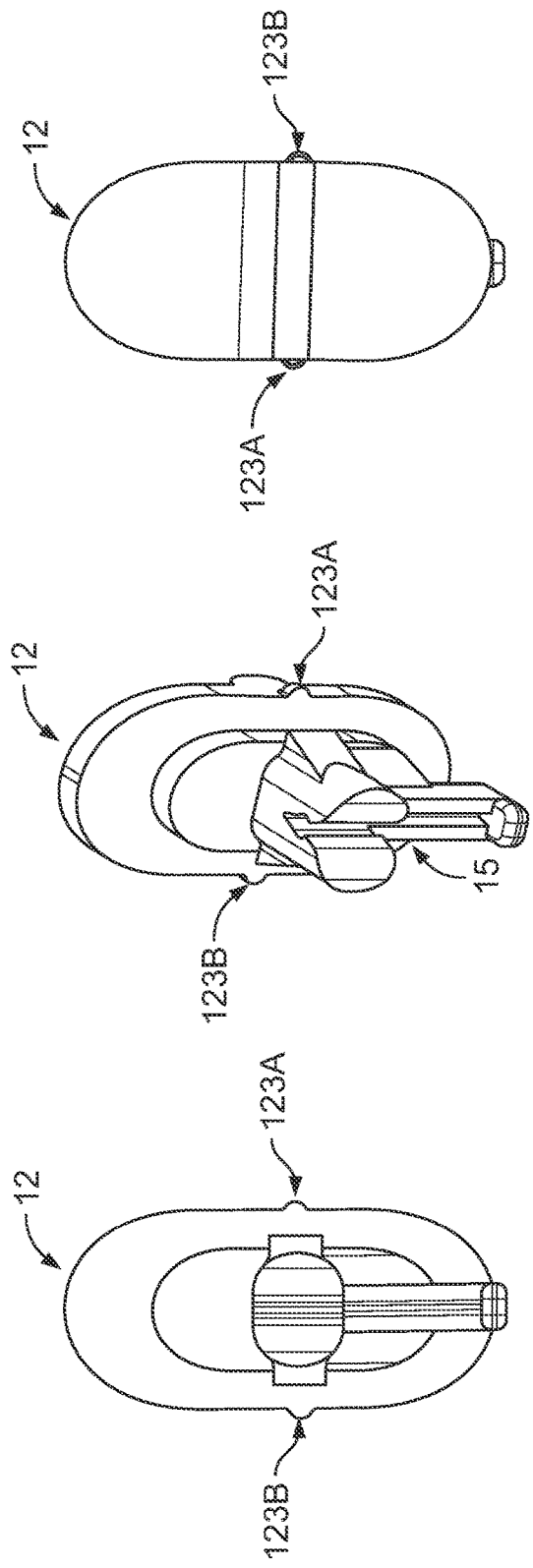

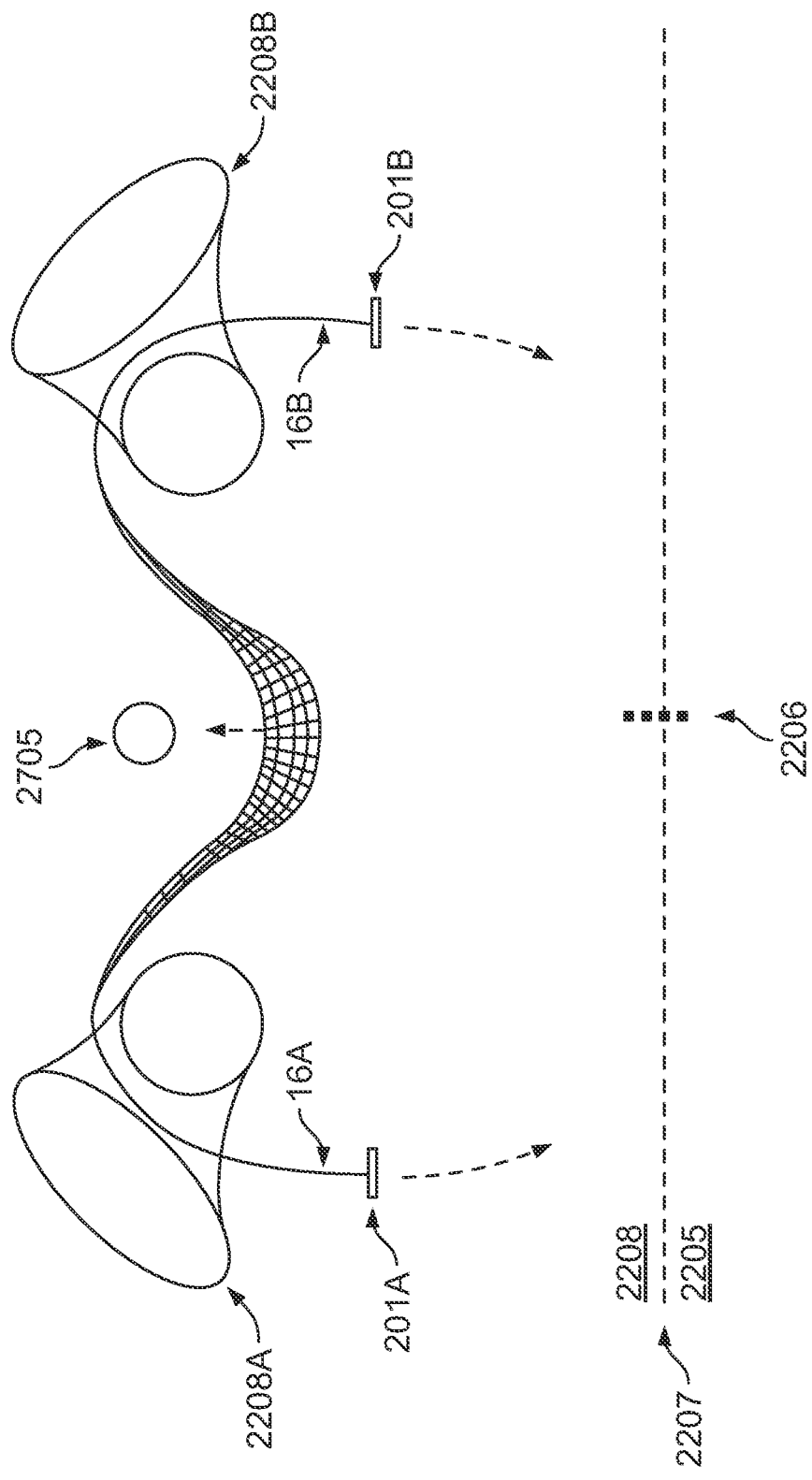

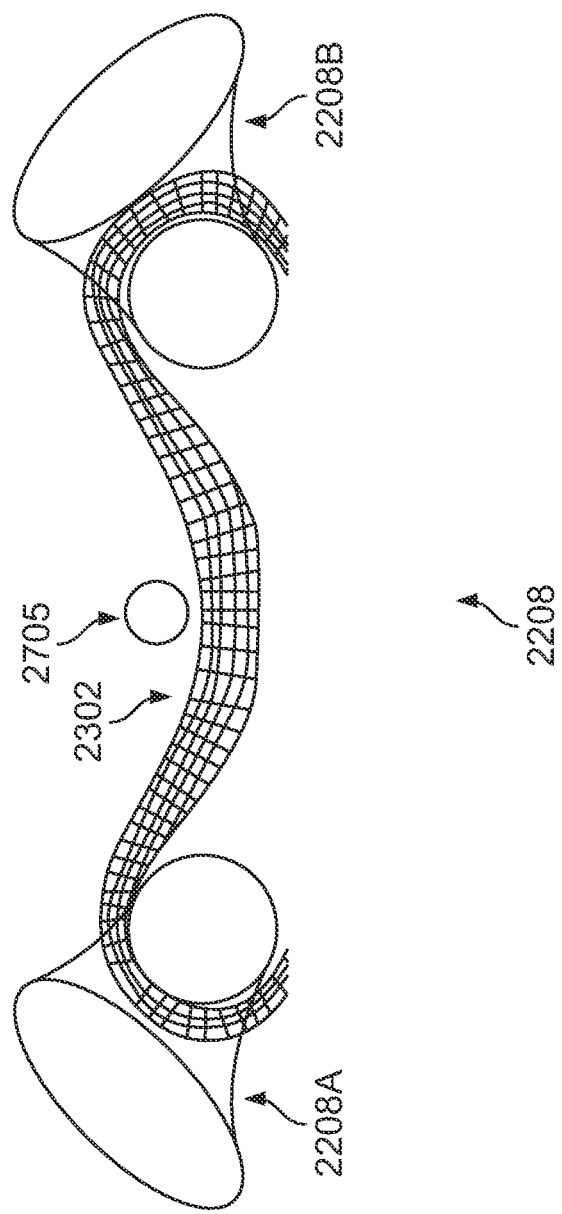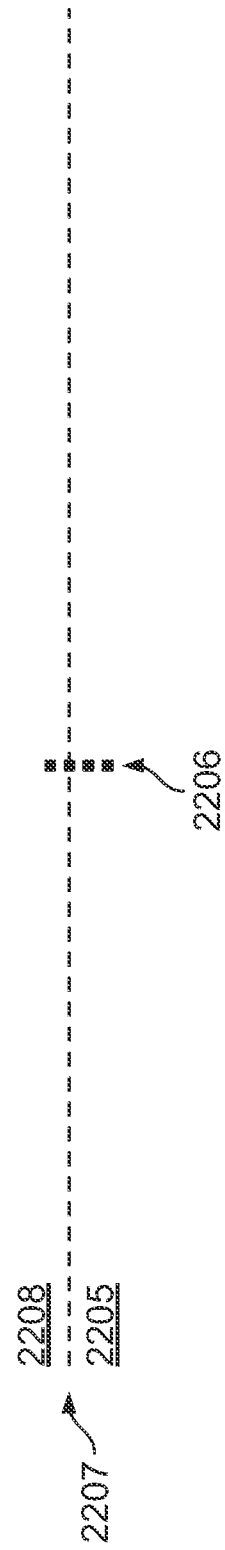
FIG. 27G

SUTURING DEVICE AND METHODS OF USE THEREOF

RELATED APPLICATIONS

This application is a continuation application of U.S. application Ser. No. 18/371,975, filed Sep. 22, 2023, which is a continuation application of U.S. application Ser. No. 18/114,874, filed on Feb. 27, 2023, now U.S. Pat. No. 11,903,576, which is a continuation application of PCT Application PCT/TR2022/050959, filed on Sep. 7, 2022, which claims the benefit of and priority to Turkish Patent Application 2021/017512, filed on Nov. 10, 2021, and Turkish Patent Application 2021/014052, filed on Sep. 7, 2021, each of which are hereby incorporated herein by reference in their entireties.

FIELD

This disclosure relates to suturing devices used in surgical operations, a suture loading apparatus for loading a suture into a suturing device, and methods of their use.

BACKGROUND

Urinary incontinence (UI) refers to the unintentional loss of urine. The disease comes in three different forms: Stress UI, Urge UI and Mixed UI. The most common is Stress UI, which happens when physical movement or activity—such as coughing, sneezing, running or heavy lifting—puts pressure (e.g., stress) on the bladder.

Abdominal colposuspension based on native tissue repair for Stress UI is based on elevation of the vaginal wall towards bilateral strong pelvic floor supportive structures such as Arcus Tendineus Fascia Pelvis (ATFP), iliopectineal ligament. However, native tissue repair is invasive and difficult because it is intensive and is a major surgery (abdominal). Transvaginal surgery is based on mesh repair for SUI. It involves the placement of tension-free mesh (sling). This method often involves placing artificial implants such as a synthetic sling or mesh.

Pelvic organ prolapse refers to the prolapse (drop) of pelvic organs from their normal position. The pelvic organs include the vagina, cervix, uterus, bladder, urethra, and rectum.

Surgical treatment of POP can be done through the abdomen or the vagina. Abdominal surgeries to repair POP can be done either based on native tissue repair or by placing artificial mesh. Transvaginal surgeries too can be either done based on native tissue repair or by placing artificial mesh. Native tissue repair done through the vagina is based on the elevation of vaginal wall or cervix (if the patient's uterus has been removed for another reason) towards strong pelvic floor supportive structures such as the Sacrospinous ligament, Sacro-uterine ligament, and Arcus Tendineus Fascia Pelvis (ATFP).

SUMMARY

In some aspects, the techniques described herein relate to a suturing device including: a fixed arm 7 integral with a fixed jaw 5 including a first grasping slot 103 configured to receive a needle 201; a movable jaw 6 including a second grasping slot 104 configured to receive the needle 201, the movable jaw 6 configured to pivot about a reference location 9 on the fixed arm 7 and relative to the fixed jaw 5 while the fixed jaw 5 remains immovable; a movable arm 8 coupled to the movable jaw 6, the movable arm 8 configured to pivot about the reference location 9 and relative to the fixed arm 7 while the fixed arm 7 remains immovable, the movable arm 8 configured to pivot away from the fixed arm 7 to move the movable jaw 6 away from the fixed jaw 5, the movable arm 8 configured to pivot towards the fixed arm 7 to move the movable jaw 6 towards the fixed jaw 5 until the needle 201 is disposed in the first grasping slot 103 and the second grasping slot 104; and a needle transfer mechanism 4 configured to secure the needle 201 in the first grasping slot 103 or the second grasping slot 104.

In some aspects, the techniques described herein relate to a suturing device, wherein the fixed arm 7 further includes an arm joint 101 located in the reference location 9, wherein the arm joint 101 is coupled to the movable arm 8, and wherein the movable arm 8 is configured to pivot about the arm joint 101 and relative to the fixed arm 7.

In some aspects, the techniques described herein relate to a suturing device, wherein the fixed arm 7 further includes a jaw joint 100 located in the reference location 9, wherein the jaw joint 100 is coupled to the movable jaw 6, and wherein the movable jaw 6 is configured to pivot about the jaw joint 100 and relative to the fixed jaw 5.

In some aspects, the techniques described herein relate to a suturing device, wherein the suturing device further includes a connecting joint 102 located in the reference location 9, wherein the connecting joint 102 is configured to link the movable arm 8 and the movable jaw 6, wherein the movable arm 8 is configured to move the connecting joint 102 to cause the movable jaw 6 to pivot about the jaw joint 100.

In some aspects, the techniques described herein relate to a suturing device, wherein the suturing device further includes an attachment member 1105 configured to be attached to the fixed jaw 5 or the movable jaw 6, the attachment member 1105 including the needle 201.

In some aspects, the techniques described herein relate to a suturing device, wherein the needle transfer mechanism 4 further includes: a first control bar 505A configured to advance towards a first notch 207A of the needle 201 disposed in the first grasping slot 103 to grasp the needle 201 in the first grasping slot 103 or retract from the first notch 207A to release the needle 201 from the first grasping slot 103; and a second control bar 505B configured to advance towards a second notch 207B of the needle 201 disposed in the second grasping slot 104 to grasp the needle 201 in the second grasping slot 104 or retract from the second notch 207B to release the needle 201 from the second grasping slot 104.

In some aspects, the techniques described herein relate to a suturing device, wherein the needle transfer mechanism 4 further includes: a first control bar 505A configured to advance a first grasping member 510A towards a first notch 207A of the needle 201 disposed in the first grasping slot 103 to grasp the needle 201 in the first grasping slot 103 or retract the first grasping member 510A from the first notch 207A to release the needle 201 from the first grasping slot 103; and a second control bar 505B configured to advance a second grasping member 510B towards a second notch 207B of the needle 201 disposed in the second grasping slot 104 to grasp the needle 201 in the second grasping slot 104 or retract the second grasping member 510B from the second notch 207B to release the needle 201 from the second grasping slot 104.

In some aspects, the techniques described herein relate to a suturing device, wherein the needle transfer mechanism 4 further includes: a first cable 3001A configured to advance to release a first spring 3002A to advance a first piston 3003A towards a first notch 207A of the needle 201 disposed in the first grasping slot 103 to grasp the needle 201 in the first grasping slot 103, the first cable 3001A further configured to pull the first piston 3003A to compress the first spring 3002A to retract the first piston 3003A from the first notch 207A to release the needle 201 from the first grasping slot 103; and a second cable 3001B configured to advance to release a second spring 3002B to advance a second piston 3003B towards a second notch 207B of the needle 201 disposed in the second grasping slot 104 to grasp the needle 201 in the second grasping slot 104, the second cable 3001B further configured to pull the second piston 3003B to compress the second spring 3002B to retract the second piston 3003B from the second notch 207B to release the needle 201 from the second grasping slot 104.

In some aspects, the techniques described herein relate to a suturing device, further including a lever 3 configured to move among: a first position 110A to advance the first control bar 505A to grasp the needle 201 in the first grasping slot 103 and retract the second control bar 505B to release the needle 201 from the second grasping slot 104, a second position 110B to retract the first control bar 505A to release the needle 201 from the first grasping slot 103 and retract the second control bar 505B to release the needle 201 from the second grasping slot 104, and a third position 110C to retract the first control bar 505A to release the needle 201 from the first grasping slot 103 and advance the second control bar 505B to grasp the needle 201 in the second grasping slot 104.

In some aspects, the techniques described herein relate to a suturing device, further including a lever 3 configured to move among: a first position 110A to advance the first cable 3001A to release the first spring 3002A to advance the first piston 3003A to grasp the needle 201 in the first grasping slot 103 and to pull the second cable 3001B to pull the second piston 3003B to compress the second spring 3002B to retract the second piston 3003B to release the needle 201 from the second grasping slot 104, a second position 1101B to pull the first cable 3001A to pull the first piston 3003A to semi-compress the first spring 3002A to semi-retract the first piston 3003A to release the needle 201 from the first grasping slot 103 and to pull the second cable 3001B to pull the second piston 3003B to semi-compress the second spring 3002B to semi-retract the second piston 3003B to release the needle 201 from the second grasping slot 104, and a third position 110C to pull the first cable 3001A to pull the first piston 3003A to compress the first spring 3002A to retract the first piston 3003A to release the needle 201 from the first grasping slot 103 and to advance the second cable 3001B to release the second spring 3002B to advance the second piston 3003B to grasp the needle 201 in the second grasping slot 104.

In some aspects, the techniques described herein relate to a suturing device, further including a lever 3 configured to move among: a first position 110A to advance the first cable 3001A to release the first spring 3002A to advance the first piston 3003A to grasp the needle 201 in the first grasping slot 103 and to pull the second cable 3001B to pull the second piston 3003B to compress the second spring 3002B to retract the second piston 3003B to release the needle 201 from the second grasping slot 104, a second position 110B to semi-pull the first cable 3001A to pull the first piston 3003A to semi-compress the first spring 3002A to semi-retract the first piston 3003A to grasp the needle 201 in the first grasping slot 103 and to semi-pull the second cable 3001B to pull the second piston 3003B to semi-compress the second spring 3002B to semi-retract the second piston 3003B to grasp the needle 201 in the second grasping slot 104, and a third position 110C to pull the first cable 3001A to pull the first piston 3003A to compress the first spring 3002A to retract the first piston 3003A to release the needle 201 from the first grasping slot 103 and to advance the second cable 3001B to release the second spring 3002B to advance the second piston 3003B to grasp the needle 201 in the second grasping slot 104.

In some aspects, the techniques described herein relate to a suturing device, further including a cover 108 partially disposed over the lever 3, the cover 108 including indicators corresponding to movements of the lever 3 to the first position 110A, the second position 110B, and the third position 110C.

In some aspects, the techniques described herein relate to a suturing device, further including a switching joint 106 coupled to the first control bar 505A and the second control bar 505B.

In some aspects, the techniques described herein relate to a suturing device, wherein the lever 3 is coupled to the switching joint 106, wherein the lever 3 is configured to rotate the switching joint 106 to move the first control bar 505A and the second control bar 505B.

In some aspects, the techniques described herein relate to a suturing device, further including a switching joint 106 coupled to the first cable 3001A and the second cable 3001B.

In some aspects, the techniques described herein relate to a suturing device, wherein the lever 3 is coupled to the switching joint 106, wherein the lever 3 is configured to rotate the switching joint 106 to pull or advance the first cable 3001A and the second cable 3001B.

In some aspects, the techniques described herein relate to a suturing device, wherein the movable arm 8 includes a stopper 605, and wherein the second control bar 505B includes a safety member 610 configured to interlock with the stopper 605 when the lever 3 is in the second position 110B to prevent the movable arm 8 from moving to prevent the needle 201 from falling out.

In some aspects, the techniques described herein relate to a suturing device, wherein the stopper 605 is configured to slide into an activated position on the movable arm 8 to secure the stopper 605 adjacent to the safety member 610 to enable the stopper 605 and the safety member 610 to interlock.

In some aspects, the techniques described herein relate to a suturing device, wherein the stopper 605 is configured to slide into a deactivated position on the movable arm 8 to secure the stopper 605 away from the safety member 610 to prevent the stopper 605 and the safety member 610 from interlocking.

In some aspects, the techniques described herein relate to a loading apparatus 10 including: a first loading slot 13 disposed in the loading apparatus 10, the first loading slot 13 configured to receive a fixed jaw 5; and a slider 12 including a slot 15 configured to hold a needle 201, the slider 12 configured to move within a loading channel 320 to move the slot 15 holding the needle 201 towards the first loading slot 13 and into a first grasping slot 103 of the fixed jaw 5.

In some aspects, the techniques described herein relate to a loading apparatus 10, further including a pulley 11 including a thread 16 coupled to the needle 201, wherein the pulley 11 is configured to rotate such that the thread 16 moves when the first grasping slot 103 of the fixed jaw 5 exits the first loading slot 13.

In some aspects, the techniques described herein relate to a loading apparatus 10, further including a second loading slot 14 disposed in the loading apparatus 10, the second loading slot 14 configured to receive a movable jaw 6, wherein the slider 12 is configured to move within the loading channel 320 to move the slot 15 holding the needle 201 towards the second loading slot 14 and into a second grasping slot 104 of the movable jaw 6.

In some aspects, the techniques described herein relate to a method including: moving a movable arm 8 of a suturing device away from a fixed arm 7 of the suturing device and about a reference location on the fixed arm 7 while the fixed arm 7 remains immovable, moving the movable arm 8 away causes a movable jaw 6 of the suturing device to pivot about the reference location and move away from a fixed jaw 5 extending from the fixed arm 7 that remains immovable and touching a cavity tissue; moving the movable arm 8 about the reference location and towards the fixed arm 7 to pivot the movable jaw 6 about the reference location and towards the fixed jaw 5 until a needle 201 secured in the fixed jaw 5 pierces through a target tissue between the fixed jaw 5 and the movable jaw 6 until the needle 201 is disposed in the movable jaw 6; actuating a needle transfer mechanism 4 of the suturing device to transfer the needle 201 from the fixed jaw 5 to the movable jaw 6; and moving the movable arm 8 about the reference location and away from the fixed arm 7 to pivot the movable jaw 6 with the needle 201 about the reference location and away from the fixed jaw 5 to move the needle 201 through the target tissue.

In some aspects, the techniques described herein relate to a method, further including pivoting the movable arm 8 relative to the fixed arm 7 and about an arm joint 101, the arm joint 101 coupled to the movable arm 8 and located in the reference location, pivoting the movable arm 8 causes the movable jaw 6 to pivot relative to the fixed jaw 5 and about a jaw joint 100 located in the reference location and coupled to the fixed arm 7.

In some aspects, the techniques described herein relate to a method, further including moving the movable arm 8 to move a connecting joint 102 configured to link the movable arm 8 and the movable jaw 6 to cause the movable jaw 6 to pivot about the jaw joint 100.

In some aspects, the techniques described herein relate to a method, further including attaching an attachment member 1105 to the fixed jaw 5 or the movable jaw 6, the attachment member 1105 including the needle 201.

In some aspects, the techniques described herein relate to a method, wherein actuating the needle transfer mechanism 4 includes: retracting a first control bar 505A from a first notch 207A of the needle 201 disposed in a first grasping slot 103 of the fixed jaw 5 to release the needle 201 from the first grasping slot 103 of the fixed jaw 5; and advancing a second control bar 505B towards a second notch 207B of the needle 201 disposed in a second grasping slot 104 of the movable jaw 6 to grasp the needle 201 in the second grasping slot 104 of the movable jaw 6.

In some aspects, the techniques described herein relate to a method, wherein subsequent to the needle 201 secured in the movable jaw 6 moving through the target tissue, further including: advancing a first control bar 505A towards a first notch 207A of the needle 201 disposed in a first grasping slot 103 of the fixed jaw 5 to grasp the needle 201 in the first grasping slot 103 of the fixed jaw 5; and retracting a second control bar 505B from a second notch 207B of the needle 201 disposed in a second grasping slot 104 of the movable jaw 6 to release the needle 201 from the second grasping slot 104 of the movable jaw 6.

In some aspects, the techniques described herein relate to a method, further including: moving a lever 3 of the suturing device to a first position 110A to advance a first control bar 505A from a first notch 207A of the needle 201 disposed in a first grasping slot 103 of the fixed jaw 5 to grasp the needle 201 in the first grasping slot 103 and retract a second control bar 505B from a second notch 207B of the needle 201 disposed in a second grasping slot 104 of the movable jaw 6 to release the needle 201 from the second grasping slot 104; moving the lever 3 of the suturing device to a second position 1101B to retract the first control bar 505A from the first notch 207A of the needle 201 disposed in the first grasping slot 103 of the fixed jaw 5 to release the needle 201 from the first grasping slot 103 and retract the second control bar 505B from the second notch 207B of the needle 201 disposed in the second grasping slot 104 of the movable jaw 6 to release the needle 201 from the second grasping slot 104; and moving the lever 3 of the suturing device to a third position 110C to retract the first control bar 505A from the first notch 207A of the needle 201 disposed in the first grasping slot 103 of the fixed jaw 5 to release the needle 201 from the first grasping slot 103 and retract the second control bar 505B from the second notch 207B of the needle 201 disposed in the second grasping slot 104 of the movable jaw 6 to release the needle 201 from the second grasping slot 104.

In some aspects, the techniques described herein relate to a method, further including a switching joint 106 coupled to the first control bar 505A and the second control bar 505B, wherein the lever 3 is coupled to the switching joint 106, and wherein the lever 3 is configured to rotate the switching joint 106 to pull or advance the first control bar 505A and the second control bar 505B.

In some aspects, the techniques described herein relate to a method, further including sliding a stopper 605 on the movable arm 8 into an activated position on the movable arm 8 to secure the stopper 605 adjacent to a safety member 610 of the second control bar 505B configured to interlock with the stopper 605 when the lever 3 is in the second position 110B to prevent the movable arm 8 from moving to prevent the needle 201 from falling out.

In some aspects, the techniques described herein relate to a method, further including sliding the stopper 605 into a deactivated position on the movable arm 8 to secure the stopper 605 away from the safety member 610 to prevent the stopper 605 and the safety member 610 from interlocking.

In some aspects, the techniques described herein relate to a method, wherein actuating the needle transfer mechanism 4 includes: retracting a first control bar 505A to retract a first grasping member 510A from a first notch 207A of the needle 201 disposed in a first grasping slot 103 of the fixed jaw 5 to release the needle 201 from the first grasping slot 103 of the fixed jaw 5; and advancing a second control bar 505B to advance a second grasping member 510B towards a second notch 207B of the needle 201 disposed in a second grasping slot 104 of the movable jaw 6 to grasp the needle 201 in the second grasping slot 104 of the movable jaw 6.

In some aspects, the techniques described herein relate to a method, wherein actuating the needle transfer mechanism 4 includes: pulling a first cable 3001A to pull a first piston 3003A to compress a first spring 3002A to retract the first piston 3003A from a first notch 207A of the needle 201 disposed in a first grasping slot 103 of the fixed jaw 5 to release the needle 201 from the first grasping slot 103 of the fixed jaw 5; and advancing a second cable 3001B to release a second spring 3002B to advance a second piston 3003B towards a second notch 207B of the needle 201 disposed in a second grasping slot 104 of the movable jaw 6 to grasp the needle 201 in the second grasping slot 104 of the movable jaw 6.

In some aspects, the techniques described herein relate to a method, further including: moving a lever 3 of the suturing device to a first position 110A to advance a first cable 3001A to release a first spring 3002A to advance a first piston 3003A to grasp the needle 201 in a first grasping slot 103 of the fixed jaw 5 and to pull a second cable 3001B to pull a second piston 3003B to compress a second spring 3002B to retract the second piston 3003B to release the needle 201 from a second grasping slot 104 of the movable jaw 6; moving the lever 3 of the suturing device to a second position 110B to pull the first cable 3001A to pull the first piston 3003A to semi-compress the first spring 3002A to semi-retract the first piston 3003A to release the needle 201 from the first grasping slot 103 and to pull the second cable 3001B to pull the second piston 3003B to semi-compress the second spring 3002B to semi-retract the second piston 3003B to release the needle 201 from the second grasping slot 104; and moving the lever 3 of the suturing device to a third position 110C to pull the first cable 3001A to pull the first piston 3003A to compress the first spring 3002A to retract the first piston 3003A to release the needle 201 from the first grasping slot 103 and to advance the second cable 3001B to release the second spring 3002B to advance the second piston 3003B to grasp the needle 201 in the second grasping slot 104.

In some aspects, the techniques described herein relate to a method, further including a switching joint 106 coupled to the first cable 3001A and the second cable 3001B, wherein the lever 3 is coupled to the switching joint 106, and wherein the lever 3 is configured to rotate the switching joint 106 to pull or advance the first cable 3001A and the second cable 3001B.

In some aspects, the techniques described herein relate to a method, further including: moving a lever 3 of the suturing device to a first position 110A to advance a first cable 3001A to release a first spring 3002A to advance a first piston 3003A to grasp the needle 201 in a first grasping slot 103 of the fixed jaw 5 and to pull a second cable 3001B to pull a second piston 3003B to compress a second spring 3002B to retract the second piston 3003B to release the needle 201 from a second grasping slot 104 of the movable jaw 6; moving the lever 3 of the suturing device to a second position 1101B to semi-pull the first cable 3001A to pull the first piston 3003A to semi-compress the first spring 3002A to semi-retract the first piston 3003A to grasp the needle 201 in the first grasping slot 103 and to semi-pull the second cable 3001B to pull the second piston 3003B to semi-compress the second spring 3002B to semi-retract the second piston 3003B to grasp the needle 201 in the second grasping slot 104; and moving the lever 3 of the suturing device to a third position 110C to pull the first cable 3001A to pull the first piston 3003A to compress the first spring 3002A to retract the first piston 3003A to release the needle 201 from the first grasping slot 103 and to advance the second cable 3001B to release the second spring 3002B to advance the second piston 3003B to grasp the needle 201 in the second grasping slot 104.

In some aspects, the techniques described herein relate to a method, further including a switching joint 106 coupled to the first cable 3001A and the second cable 3001B, wherein the lever 3 is coupled to the switching joint 106, and wherein the lever 3 is configured to rotate the switching joint 106 to pull or advance the first cable 3001A and the second cable 3001B.

In some aspects, the techniques described herein relate to a method, further including: inserting the fixed jaw 5 of the suturing device into a first loading slot 13 disposed in a loading apparatus 10; and moving a slider 12 including a slot 15 configured to hold the needle 201 within a loading channel 320 of the loading apparatus 10 to move the slot 15 holding the needle 201 towards the first loading slot 13 and into a first grasping slot 103 of the fixed jaw 5.

In some aspects, the techniques described herein relate to a method, further including upon actuating the needle transfer mechanism 4, removing the suturing device and pulling on a curved needle 18 attached to a first end of a thread 16 that is opposite a second end of the thread 16 attached to the needle 201.

In some aspects, the techniques described herein relate to a method, wherein subsequent to moving the movable arm 8 away from the fixed arm 7 to pivot the movable jaw 6 away from the fixed jaw 5 to move the needle 201 through the target tissue, the method further includes: moving the movable arm 8 about the reference location and towards the fixed arm 7 to pivot the movable jaw 6 about the reference location and towards the fixed jaw 5 until the needle 201 secured in the movable jaw 6 pierces through a different section of the target tissue until the needle 201 is disposed in the fixed jaw 5; and actuating the needle transfer mechanism 4 to transfer the needle 201 from the movable jaw 6 to the fixed jaw 5.

In some aspects, the techniques described herein relate to a system including: a mesh 2302 extending between a first positioning thread 16A and a second positioning thread 16B, the first positioning thread 16A attached to a first positioning needle 201A and the second positioning thread 16B attached to a second positioning needle 201B; a first loading slot 13A and a second loading slot 13B disposed in a sling loader 2315, the first loading slot 13A and the second loading slot 13B configured to receive a fixed jaw 5 of a suturing device; a first slider 12A attached to the sling loader 2315, the first slider 12A including a first slot 15A configured to hold the first positioning needle 201A, the first slider 12A configured to move within a first loading channel 320A of the sling loader 2315 to move the first slot 15A holding the first positioning needle 201A towards the first loading slot 13A and into a first grasping slot 103 of the fixed jaw 5; and a second slider 12B attached to the sling loader 2315, the second slider 12B including a second slot 15B configured to hold the second positioning needle 201B, the second slider 12B configured to move within a second loading channel 320B of the sling loader 2315 to move the second slot 15B holding the second positioning needle 201B towards the second loading slot 13B and into the first grasping slot 103 of the fixed jaw 5.

In some aspects, the techniques described herein relate to a system, further including a first adjustment thread 2308A, a second adjustment thread 2308B, and a third adjustment thread 2308C each extending from the mesh 2302, the second adjustment thread 2308B extending between the first adjustment thread 2308A and the third adjustment thread 2308C.

In some aspects, the techniques described herein relate to a system, wherein each end of the first adjustment thread 2308A includes a first curved needle 2310A and a second curved needle 2310B, each end of the second adjustment thread 2308B includes a third curved needle 2310C and a fourth curved needle 2310D, and each end of the third adjustment thread 2308C includes a fifth curved needle 2310E and a sixth curved needle 2310F.

In some aspects, the techniques described herein relate to a method including: moving a first slider 12A of a loading apparatus 2315 within a first sliding channel 320A of a first loading slot 13A to move a first needle 201A disposed in a first slot 15A of the first slider 12A into a first grasping slot 103 of a fixed jaw 5 extending from a fixed arm 7 of a suturing device loaded in the first loading slot 13A, the first needle 201A attached to a first thread 16A attached to a mesh 2302; actuating a lever 3 of the suturing device to secure the first needle 201A in the first grasping slot 103; moving a movable arm 8 of the suturing device away from the fixed arm 7 and about a reference location on the fixed arm 7 while the fixed arm 7 remains immovable, moving the movable arm 8 away causes a movable jaw 6 of the suturing device to pivot about the reference location and move away from the fixed jaw 5 while the fixed jaw 5 remains immovable; moving the movable arm 8 about the reference location and towards the fixed arm 7 to pivot the movable jaw 6 about the reference location and towards the fixed jaw 5 until the first needle 201A secured in the first grasping slot 103 pierces through a first portion of a palpated tissue between the fixed jaw 5 and the movable jaw 6 and the first needle 201A is received in a second grasping slot 104 of the movable jaw 6; removing the suturing device from a pelvic cavity 2208 and actuating a needle transfer mechanism 4 of the suturing device to release the first needle 201A from the second grasping slot 104; moving a second slider 12B of the loading apparatus 2315 within a second sliding channel 320B of a second loading slot 13B of the loading apparatus 2315 to move a second needle 201B disposed in a second slot 15B of the second slider 12B into the first grasping slot 103 of the fixed jaw 5 loaded in the second loading slot 13B, the second needle 201B attached to a second thread 16B attached to the mesh 2302; actuating the lever 3 of the suturing device to secure the second needle 201B in the first grasping slot 103; moving the movable arm 8 about the reference location and towards the fixed arm 7 to pivot the movable jaw 6 about the reference location and towards the fixed jaw 5 until the second needle 201B secured in the first grasping slot 103 pierces through a second portion of the palpated tissue on an other side of the first portion of the palpated tissue between the fixed jaw 5 and the movable jaw 6 and is received in the second grasping slot 104 to place the mesh 2302 in the pelvic cavity 2208; removing the suturing device from the pelvic cavity 2208 and cutting off the first thread 16A, the second thread 16B, and a portion of the mesh 2302; attaching a first adjustment suture 2305A, a second adjustment suture 2305B, and a third adjustment suture 2305C to the mesh 2302, the first adjustment suture 2305A and the third adjustment suture 2305C attached to each end of the mesh 2302 for tensioning, the second adjustment suture 2305B attached to a middle of the mesh 2302 for loosening the mesh 2302; cutting off curved needles 2310 coupled to each of the adjustment sutures 2305 to make knots 2720 of threads 2308 of the adjustment sutures 2305 to form loops and place the knots 2720 into a housing 2725 and leaving the knots 2720 secured in the housing 2725 inside a vaginal cavity 2205 of a patient and closing an incision 2206 in the vaginal cavity 2205; and pulling on adjustment sutures 2305 coupled to the mesh 2302 to adjust a tension of the mesh 2302 during early post-operative check-up of the patient in an office set up without needing a new operation.

In some aspects, the techniques described herein relate to a method, wherein pulling the adjustment sutures 2305 includes pulling the knots 2720 disposed in the housing 2725 attached to the adjustment sutures 2305 to adjust the tension of the mesh 2302, and once the tensioning is finished, cut the loops and take away the housing 2725 and the adjustment sutures 2305.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 4A, FIG. 4B, FIG. 4C depict an embodiment of the suturing device including joints for facilitating movement of the movable arm and the movable jaw.

FIG. 5F, FIG. 5G, FIG. 5H, FIG. 5I depict an embodiment of a needle having an open channel feature-based joining of needle and thread.

FIG. 5N, FIG. 5O, and FIG. 5P depicts an embodiment of the suturing device including mechanisms for securing and releasing the needle.

FIG. 9A depicts an embodiment of the suturing device including the stopper transitioning from an active position to a deactivated position.

FIG. 9B, and FIG. 9C depict exploded views of the stopper and the movable arm.

FIG. 10A and FIG. 10B depict an embodiment of the suturing device including the stopper in the deactivated position to allow the movable arm to move even when the needle is unsecured.

FIG. 11B and FIG. 11C depict an embodiment of the suturing device with an attachment member.

FIG. 14A, FIG. 14B, and FIG. 14C depict an embodiment of the loading apparatus and the needle.

FIGS. 20A-20I depict use of the loading apparatus to load a suture into the suturing device.

FIG. 22DD depicts an embodiment of an operator holding the suturing device for palpating during suturing operations.

FIG. 27A-27J depicts an embodiment of inserting the mini sling.

Figure 1A:
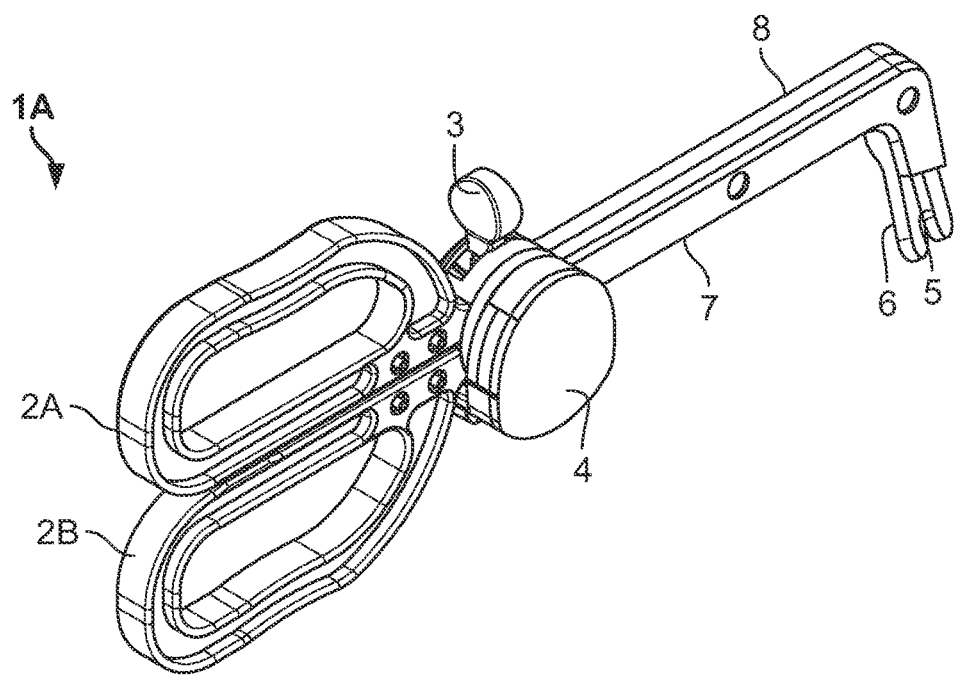
FIG. 1A and FIG. 1B depict an embodiment of the suturing device.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

REFERENCE LIST

1A-B Suturing device
2A First Handle
2B Second Handle
3 Lever
4 Needle transfer mechanism
5 Fixed jaw
6 Movable jaw
7 Fixed arm
8 Movable arm
9 Reference location
10 Loading apparatus
11 Pulley
12 Slider
12A First Slider
12B Second Slider
13 First loading slot
14 Second loading slot
15 Slot
15A First slot
15B Second slot
16 Thread
16A First Thread
16B Second Thread
17 Fixing wall
18 Curved needle
100 Jaw joint
101 Arm joint
102 Connecting joint
103 First grasping slot
104 Second grasping slot
105 Arm movement
106 Switching joint
107 Jaw movement
108 Cover
110A First position
110B Second position
110C Third position
112A-B-C Safety positions
121A-B Safety notches
122A-B Notches
123A-B Protrusions
201 Needle
201A First needle
201B Second needle
201C-D-E Embodiments of the needle 201
207A First notch
207B Second notch
208 Hole
209 Channel
301A-B First Fasteners
302A-B Second Fasteners
320 Loading channel
505A First Control bar
505B Second control bar
510A First grasping member
510B Second grasping member
515A-B-C Security notches
605 Stopper
606 Lid
607 Flap
608 Protrusion
610 Safety member
615 Base region
616A-B Notches
617 Sliding channel
1105A-B Attachment members
1205A-B Lengths
1800 Method
1802 Step of Method 1800
1804 Step of Method 1800
1806 Step of Method 1800
1808 Step of Method 1800
1810 Step of Method 1800
1812 Step of Method 1800
1814 Step of Method 1800
2205 Vaginal cavity
2206 Incision
2207 Vaginal wall
2208 Pelvic cavity
2208A Pelvic cavity
2208B Pelvic cavity
2209A-B-C-D-E-F Pierce points
2210 Stop area
2211 Index finger
2300 Mini sling
2302 Mesh 2305A-B-C Adjustment sutures
2308A-B-C Threads of Adjustment Sutures
2310A-B-C-D-E-F Curved needles
2315 Sling loader
2705 Urethra
2710 Excess portion
2720A-B-C Knots
2725A-B-C Housing
3001A-B Cables
3002A-B Springs
3003A-B Pistons
3004A-B Stubs
3005A-B Geometric features
3006A-B Geometric features
3007A-B Geometric features
3008A-B Machine elements

DETAILED DESCRIPTION

The present disclosure includes an improved suturing device, suture loader, tension-free mid-urethral sling, and methods of their use. The suture loader can load the threaded needle into the suturing device. The suturing device can be inserted into a cavity to reach a tissue to be sutured. The suturing device can include a fixed jaw and a movable jaw between which the tissue is placed for suturing. The fixed jaw stays in position while the movable jaw moves the threaded needle to suture the tissue. The suturing device includes a needle transfer mechanism that passes the needle between the jaws while suturing the tissue. A stopper and a safety member can control the movement of the movable jaw to prevent the needle from falling out when the needle is transferred between the jaws. When the suturing is complete, the suturing device can be removed from the cavity with the needle.

Section A: Suturing Devices

Figure 1B:
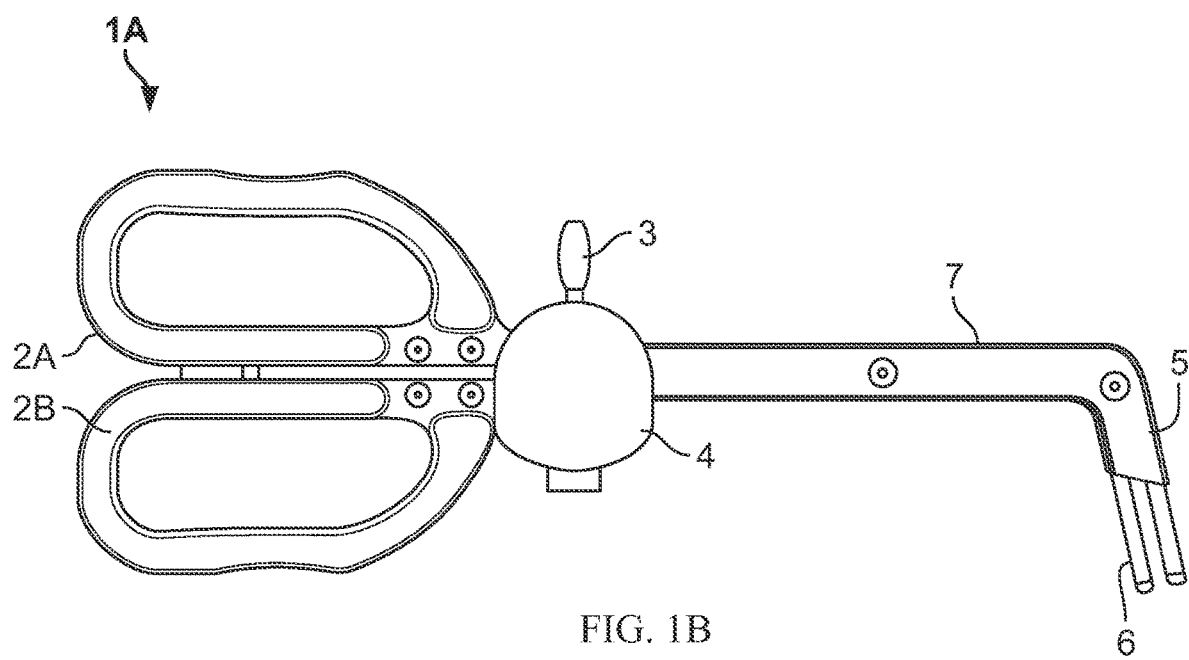

Now referring generally to FIG. 1A and FIG. 1B, the suturing device 1A can be scissor-shaped and ergonomically sized to reach target tissues in a tight space. The suturing device 1A can include a fixed arm 7 integral with a fixed jaw 5. In some embodiments, a distal end of the fixed arm 7 includes the fixed jaw 5. The suturing device 1A can include a movable arm 8 coupled to a movable jaw 6.

The fixed jaw 5 and the moveable jaw 6 can both receive and grasp a needle, and the suturing device 1A can also include a needle transfer mechanism 4 to transfer the needle between the fixed jaw 5 and the movable jaw 6. The needle transfer mechanism 4 may include a lever 3 for controlling the transfer of the needle between the fixed jaw 5 and the moveable jaw 6. In some embodiments, the lever 3 extends from the fixed arm 7.

In some embodiments, the suturing device 1A can include a first handle 2A coupled to the fixed arm 7 and a second handle 2B coupled to the movable arm 8. The handle 2A and the handle 2B can aid the user in moving the moveable arm 8 relative to the fixed arm 7. The handle 2A and the handle 2B can be disposed at the end of the suturing device 1A that remains outside of the cavity during the operation such that the operator can control the suturing device 1A.

Figure 2A:
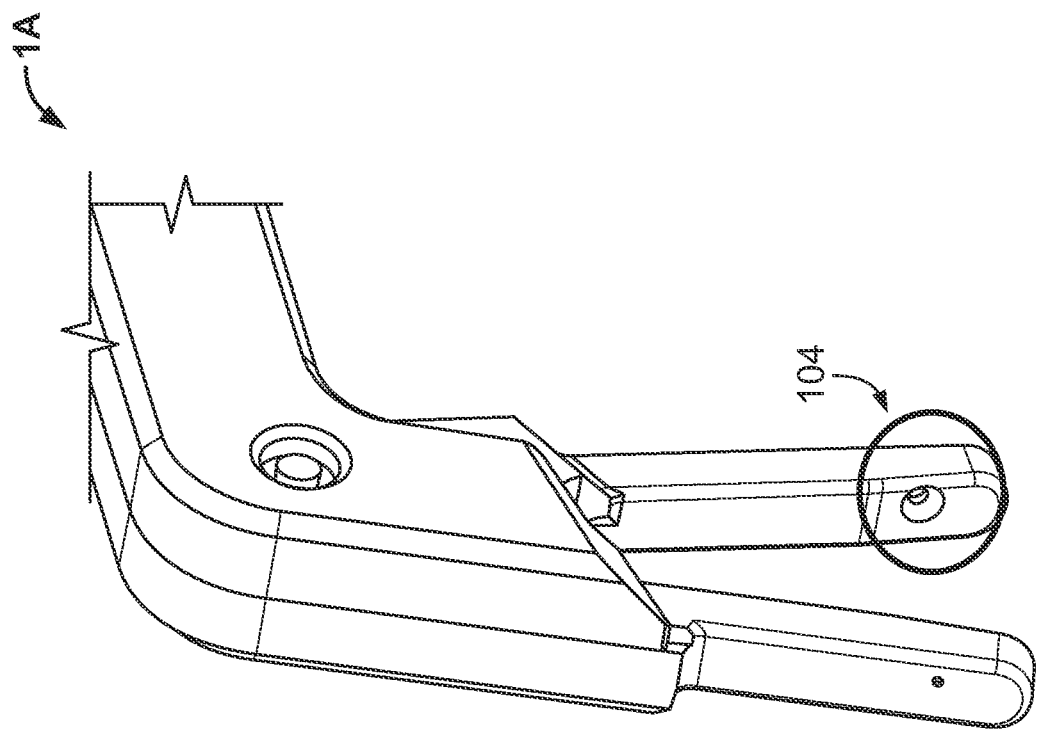
FIG. 2A and FIG. 2B depict an embodiment of the grasping slots of the suturing device.
Figure 2B:
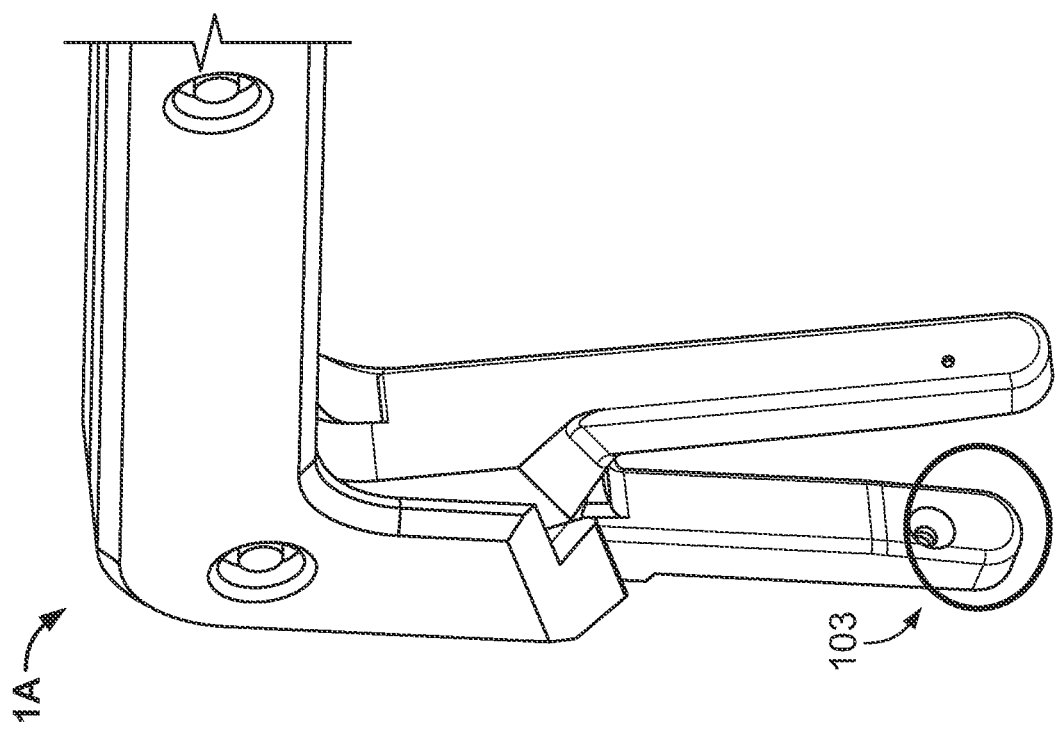

FIG. 2A and FIG. 2B depict an embodiment of the suturing device 1A. In some embodiments, the fixed jaw 5 includes a first grasping slot 103 that can receive the needle 201 (further described in reference to FIG. 5B). In some embodiments, the movable jaw 6 includes a second grasping slot 104 that can receive the needle 201. In some embodiments, the grasping slots are channel sized and shaped to receive the needle. For example, the grasping slots can define a round channel or a round hole for receiving and grasping the needle.

In some embodiments, the needle transfer mechanism 4 can transfer the needle between the first grasping slot 103 and the second grasping slot 104. To that end, the needle transfer mechanism can secure the needle in the first grasping slot 103 or the second grasping slot 104, or to release the needle from the first grasping slot 103 or the second grasping slot 104.

Figure 3B:
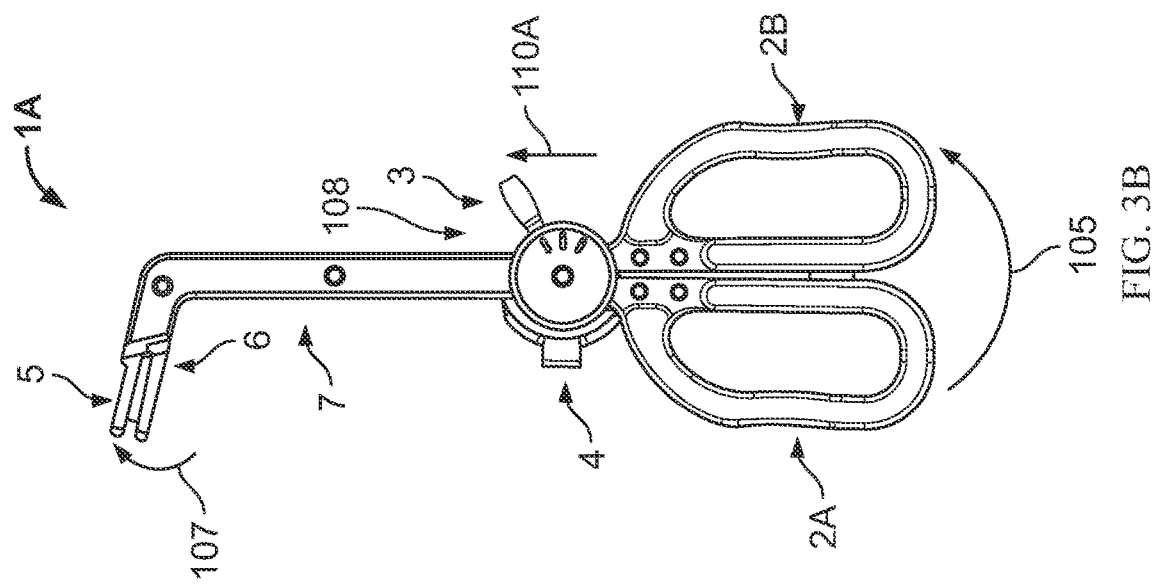
FIG. 3A and FIG. 3B depict an embodiment of the suturing device including movement of the movable arm and the movable jaw while the needle is secured in the fixed jaw.
Figure 3A:
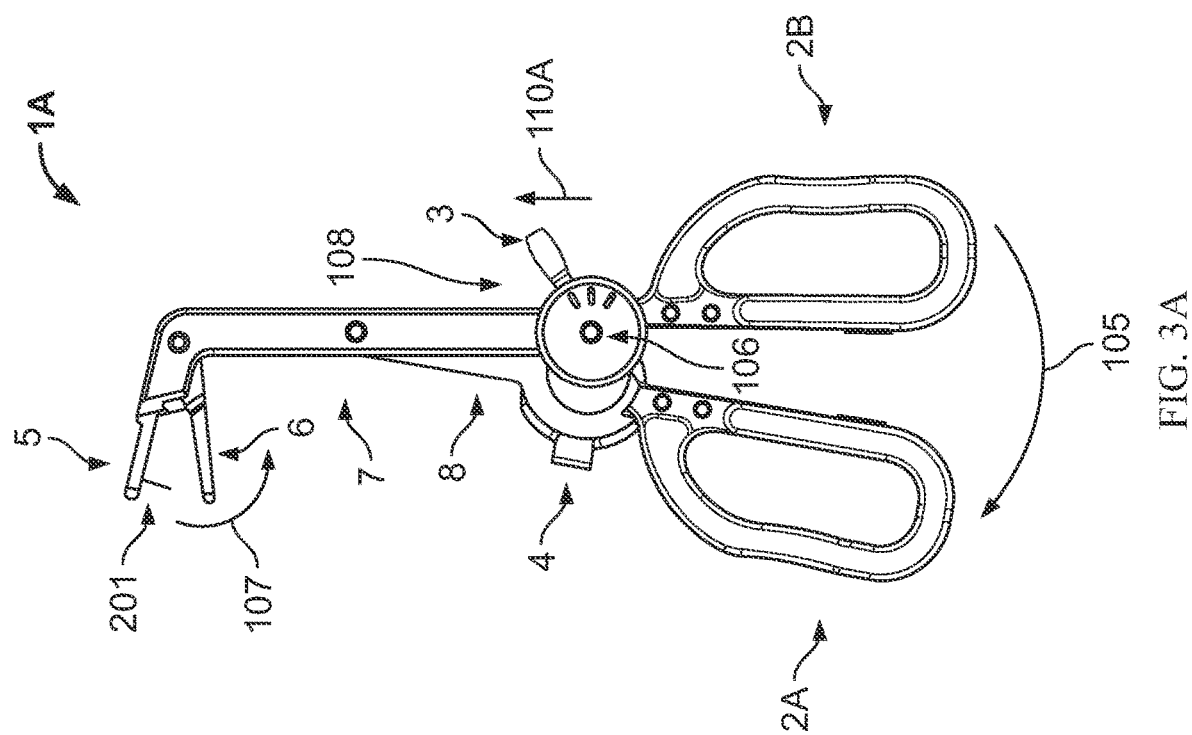

FIGS. 3A-3E show an embodiment of a mechanism for moving the movable arm 8 to pivot relative to the fixed arm 7 to pivot the movable jaw 6 relative to the fixed jaw 5. As shown in FIG. 3A, the movable arm 8 can have an arm movement 105 along which the movable arm 8 pivots away or towards the fixed arm 7. For example, the arm movement 105 can be caused by a surgeon's manual movement of handle 2A to open and close the device 1A. This control can be advantageous while operating in invisible areas to make sure that movement of the device 1A can be under the operator's control. In some embodiments, the arm movement 105 can be caused by additional mechanical force elements such as a spring.

The fixed arm 7 can remain immovable relative to the movable arm 8 while the movable arm 8 moves. The movable arm 8 can pivot relative to the fixed arm 7 to pivot the movable jaw 6 relative to the fixed jaw 5. The movement of the moveable arm 8 relative to the fixed arm 7 can enable the movable jaw 6 to have a jaw movement 107 along which the movable jaw 6 can pivot away or towards the fixed jaw 5. The fixed jaw 5 can remain immovable relative to the movable jaw 6 while the movable jaw 6 moves. In some embodiments, the movable arm 8 and the movable jaw 6 move relative to the fixed arm 7. In some embodiments, the movable arm 8 and the movable jaw 6 move relative to the fixed jaw 5. In some embodiments, the movable arm 8 and the movable jaw 6 move relative to each other. In some embodiments, the fixed arm 7 and the fixed jaw 5 do not move. In some embodiments, the fixed jaw 5 cannot move independently of the fixed arm 7 because the fixed arm 7 is integral with the fixed jaw 5.

The fixed jaw 5 can make it easier to work safely in narrow spaces because having the fixed jaw 5 remain stationary with respect to the target tissue allows the sutures to be placed while staying in a safe area. For example, when an operator moves the movable jaw 6 relative to the fixed jaw 5, the operator would know the location of the fixed jaw 5. When the target tissue is referenced with the fixed jaw 5 at an operating place that is difficult to see or not visible at all, the fixed jaw 7 enables the suture to pass through the targeted tissue. The fixed jaw 5 and the movable jaw 6 can come together at a constant or predictable location with respect to the tissue such that the location and distance does not need to be predicted continuously to center the tissue. Thus, the fixed jaw 5 enables suturing in areas that are difficult to see.

As shown in FIG. 3B, in some embodiments, the movable arm 8 can be pivoted relative to the fixed arm 7 to pivot the movable jaw 6 relative to the fixed jaw 5. The movable arm 8 can pivot the movable jaw 6 relative to the fixed jaw 5 until the needle 201 is received in both the first grasping slot 103 and the second grasping slot 104 to exchange the needle between the slots.

As shown in FIGS. 3A-3E, in some embodiments, the lever 3 can move among a first position 110A, a second position 110B, or a third position 110C to control the securing and releasing of both the first grasping slot 103 and the second grasping slot 104. For example, the lever 3 can be a shifter, grip, or switch that can be moved by the operator. In the first position 110A, the needle 201 is secured in the first grasping slot 103 of the fixed jaw 5. As shown in FIG. 3A, when the movable arm 8 is moving or open, the needle transfer mechanism 4 can grasp of the needle 201 in the fixed jaw 5 while keeping the grasping inactive in the movable jaw 6. As shown in FIG. 3B, when the movable arm 8 is adjacent to the fixed arm 7, the needle transfer mechanism 4 can grasp the needle 201 in the fixed jaw 5 while keeping the grasping inactive in the movable jaw 6 by keeping the lever 3 in the first position 110A.

Figure 3D:
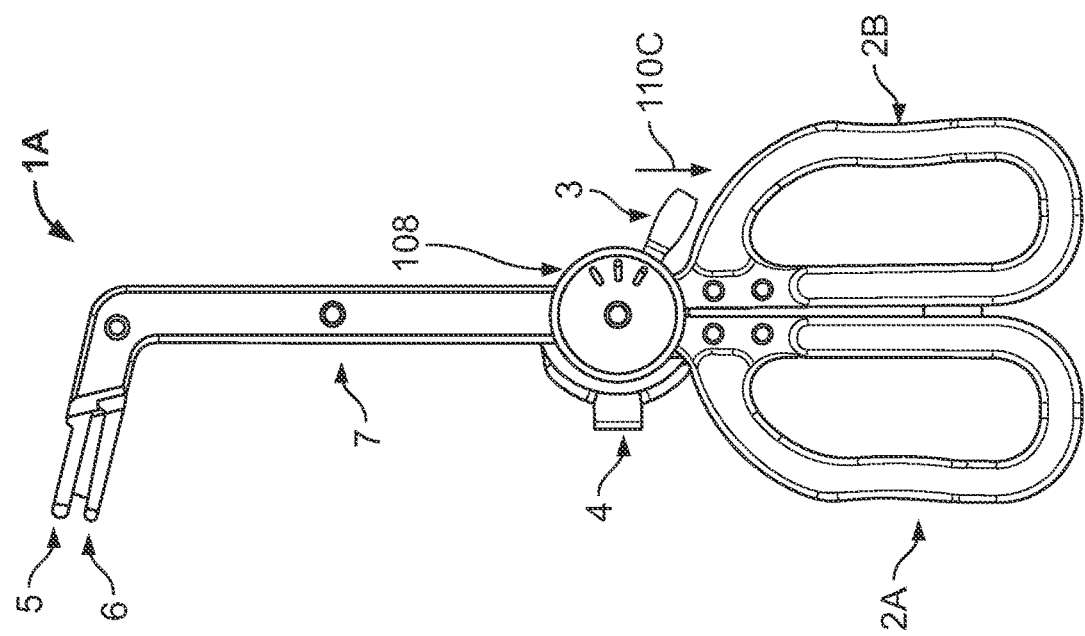
FIG. 3C and FIG. 3D depict an embodiment of the suturing device including the needle transfer mechanism transferring the needle.
Figure 3C:
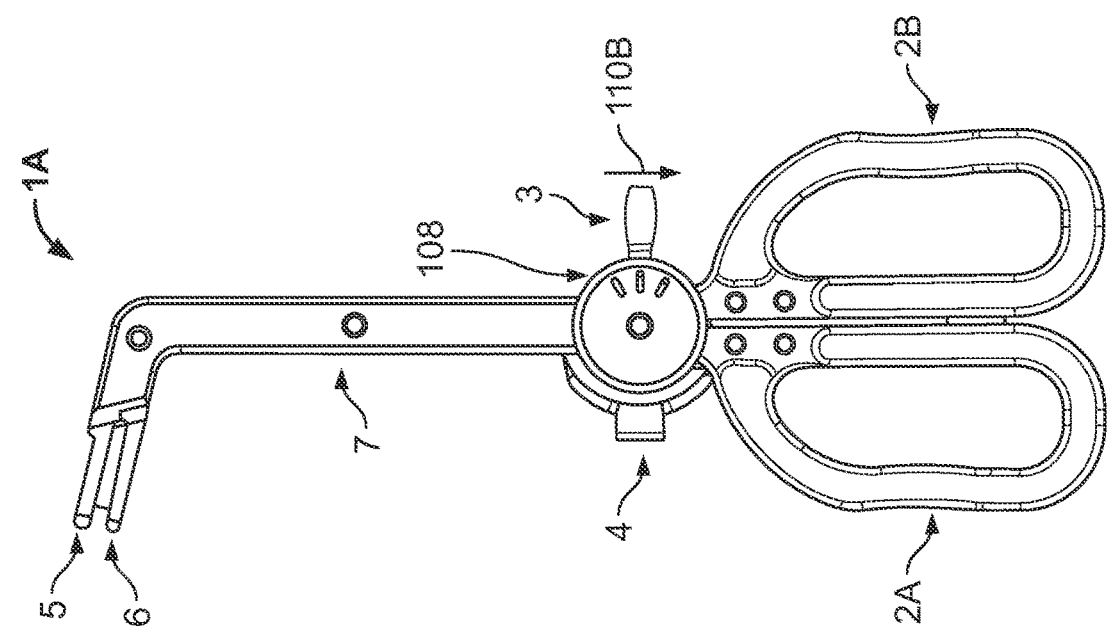

As shown in FIG. 3C, the lever 3 can then be moved to the second position 110B, so the needle 201 is released from the first grasping slot 103, while still unsecure in the second grasping slot 104. As shown in FIG. 3C, the needle transfer mechanism 4 can be inactive in both the fixed jaw 5 and the movable jaw 6 to release the needle 201.

Figure 3E:
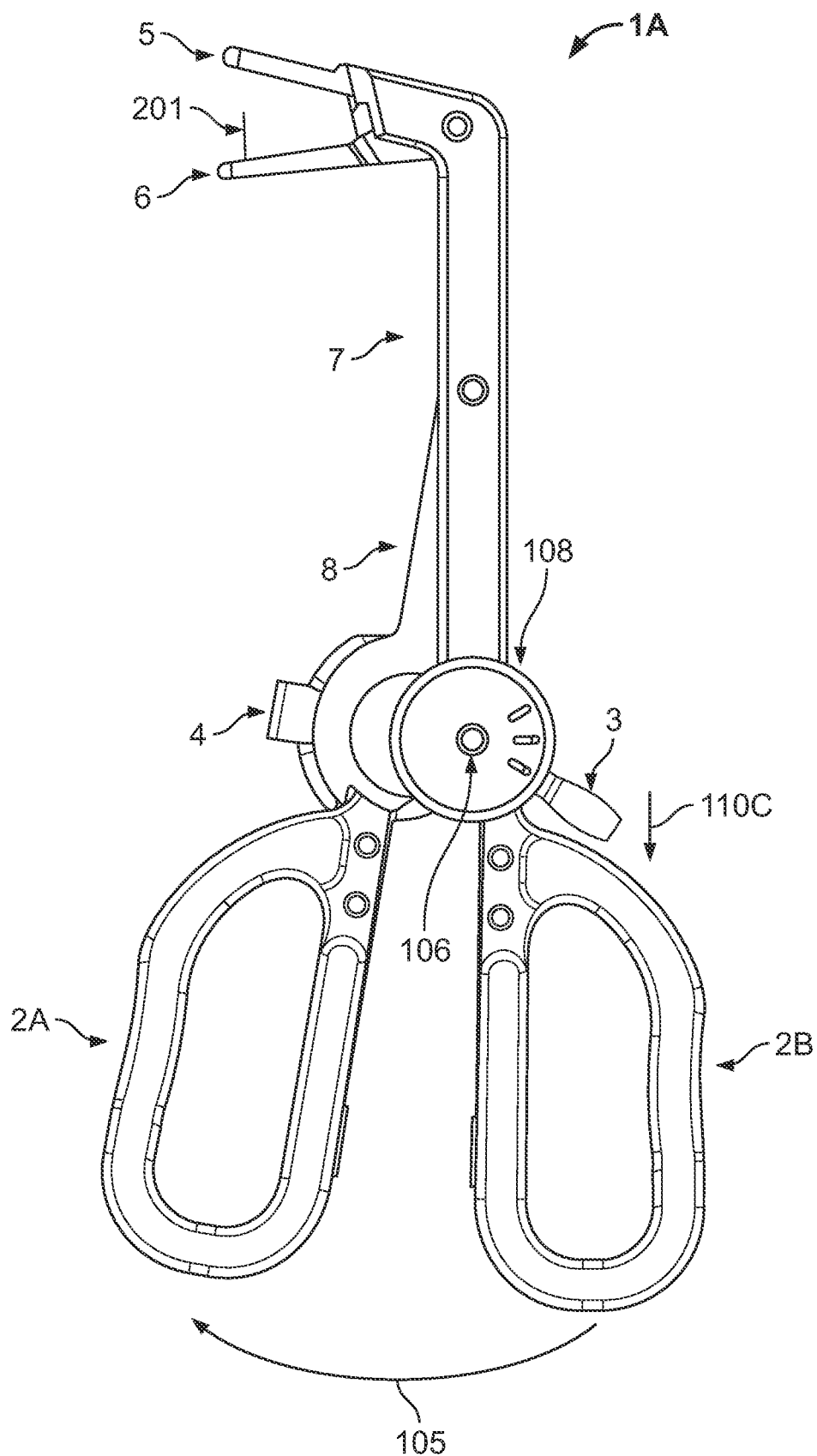
FIG. 3E depict an embodiment of the suturing device including movement of the movable arm and the movable jaw while the needle is secured in the movable jaw.

As shown in FIG. 3D, in the third position 110C, the needle 201 is secured in the second grasping slot 104. As shown in FIG. 3D, the needle transfer mechanism 4 can grasp of the needle 201 in the movable jaw 6 while keeping the grasping inactive in the fixed jaw 5. As shown in FIG. 3E, when the moveable jaw 6 pivots away from the fixed jaw 5 by the movement of the moveable arm 8, the needle is secured in the moveable jaw 6, thus completing the transfer of the needle between the fixed jaw 5 and the moveable jaw 6. As shown in FIG. 3E, when the movable arm 8 is moving or open, the needle transfer mechanism 4 can grasp of the needle 201 in the movable jaw 6 while keeping the grasping inactive in the fixed jaw 5.

Referring generally to FIGS. 3A-3E, in some embodiments, the suturing device 1A further includes a cover 108 partially disposed over the lever 3. The lever 3 can move among the positions to set the first position 110A, the second position 110B, or the third position 110C. In some embodiments, the cover 108 includes ticks, indents, or indicators corresponding to movements of the lever 3 to the first position 110A, the second position 110B, or the third position 110C.

FIGS. 4A-4C depict an embodiment mechanism of the suturing device 1A for the movement of the moveable arm 8 relative to the fixed arm 7 to enable the movable jaw 6 to have the jaw movement 107 along which the movable jaw 6 pivots away or towards the fixed jaw 5. In some embodiments, the fixed arm 7 can include an arm joint 101 to couple the fixed arm 7 to the movable arm 8. For example, the arm joint 101 can be a mechanical joint for connecting two components and allowing them to move relative to each other. In some embodiments, the arm joint 101 enables the movement of the moveable arm 8 relative to the fixed arm 7. For example, the movable arm 8 can pivot about the arm joint 101 and relative to the fixed arm 7. In another example, the arm joint 101 can allow the movable arm 8 to pivot relative to the fixed arm 7 in one degree of freedom. In yet another example, the arm joint 101 can restrict some movement of the movable arm 8, such as to prevent the movable arm 8 from breaking or exerting excessive force on the movable jaw 6, the slots, or any other component described herein.

In some embodiments, the fixed arm 7 includes a jaw joint 100. In some embodiments, the fixed jaw 5 includes the jaw joint 100. The jaw joint 100 is coupled to the movable jaw 6 so that the movable jaw 6 can pivot relative to the fixed jaw 5. For example, the jaw joint 100 can be a mechanical joint for connecting two components and allowing them to move relative to each other. In some embodiments, the movable jaw 6 can pivot about the jaw joint 100 and relative to the fixed jaw 5. For example, the jaw joint 100 can allow the movable jaw 6 to pivot relative to the fixed jaw 5 in one degree of freedom. In another example, the jaw joint 100 can restrict some movement of the movable jaw 6, such as to prevent the movable jaw 6 from breaking or exerting excessive force on the fixed jaw 5, the slots, or any other component described herein.

In some embodiments, the suturing device 1A further includes a connecting joint 102 coupled to the movable arm 8 and the movable jaw 6. The connecting joint 102 can be positioned between the jaw joint 100 and the arm joint 101 such that the jaw joint 100 and the arm joint 101 are decoupled and mechanically independent from each other. The connecting joint 102 can allow movement of the movable arm 8 to pivot the movable jaw 6. For example, the connecting joint 102 can be a mechanical joint for connecting two components and allowing them to move relative to each other. In some embodiments, the movable arm 8 can physically move the connecting joint 102 to cause the movable jaw 6 to pivot about the jaw joint 100. Movement of the movable arm 8 can move the connecting joint 102 to pivot the movable jaw 6 about the jaw joint 100. For example, as shown in FIG. 4B and FIG. 4C, movement of the movable arm 8 away from the fixed arm 7 causes the connecting joint 102 to move across the width of the fixed arm 7. The connecting joint 102 pulls on the movable jaw 6, which causes the movable jaw 6 to pivot about the jaw joint 100 and away from the fixed jaw 5.

In some embodiments, the connecting joint 102 can restrict some movement of the movable jaw 6 and the movable arm 8, such as to prevent them from disconnecting or exerting excessive force on the slots or any other component described herein. For example, the connecting joint 102 can be restricted to movements along the width of the fixed arm 7, which would prevent from excessive movements of the movable jaw 6 and the movable arm 8. In some embodiments, the part of the fixed arm 7 between the jaw joint 100 and the arm joint 101 can remain in a fixed position while the movable jaw 6 moves inside the pelvic cavity and the movable arm 8 moves outside the vaginal cavity. Such movements can advantageously reduce the profile of the movable jaw 6 and the movable arm 8.

In some embodiments, the fixed arm 7 includes a reference location 9 comprising the jaw joint 100, the arm joint 101, and the connecting joint 102. The pivoting movements of the movable arm 8 and the movable jaw 6 about the reference location 9 enable the suturing device 1A to move like a scissors-type mechanism. For example, the suturing device 1A can be comprised of 3 rigid metal parts (e.g., (1) fixed jaw 7 integral with the fixed jaw 5, (2) the movable arm 8, and (3) the movable jaw 6) that are attached to each other with the three joints 100-102. The movable jaw 6 and the movable arm 8 can move with respect to each other and the fixed arm 7 and fixed jaw 5 about the reference location 9 in 2D space as described above. In some embodiments, the movable arm 8 pivots about the reference location 9 and relative to the fixed arm 7. In some embodiments, the movable jaw 6 pivots about the reference location 9 and relative to the fixed arm 5.

For example, during the operation of the suturing device 1A inside the pelvic cavity, in order to perform the stitching at the correct location, the fixed arm 7, whose outer contour can be designed accordingly, can be aligned with the specific area of the pelvic cavity and becomes fixed with respect to this specific area of the pelvic cavity while the jaw joint 100, the arm joint 101, and the connecting joint 102 enable the operator to move the handle 2A to move the movable arm 8 to move the movable jaw 6. By keeping the fixed arm 7 fixed in position, the jaws 5 and 6 can be correctly positioned for suturing.

FIGS. 5A-5I depict embodiments of the needle 201. The needle 201C, the needle 201D, and the needle 201E (generally referred to as needle 201) can include a first notch 207A and a second notch 207B. The position of the first notch 207A and the second notch 207B on the needle 201 enable the needle 201 to be grasped within the first grasping slot 103 or the second grasping slot 104, or both. For example, the first notch 207A can be attached to the fixed jaw 5 and the second notch 207B can be attached to the movable jaw 6.

Figure 5A:
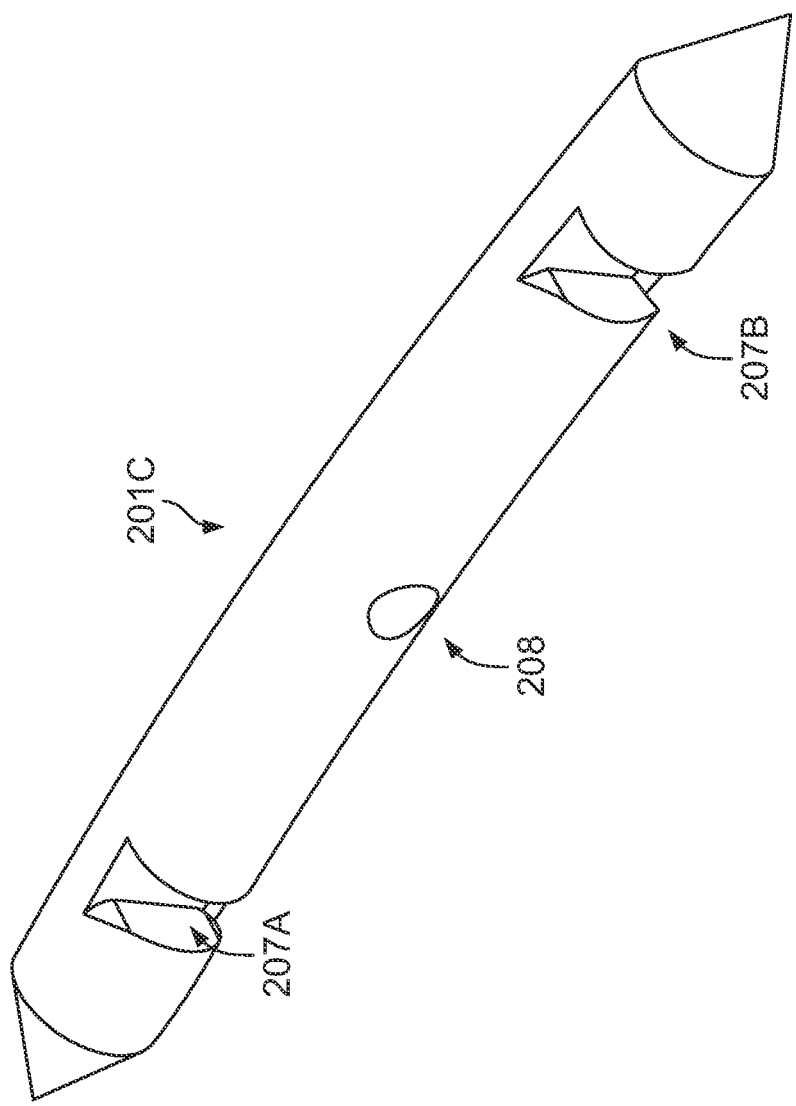
FIG. 5A depicts an embodiment of a concave needle for the suturing device.
Figures 5B, 5C, 5D, 5E:
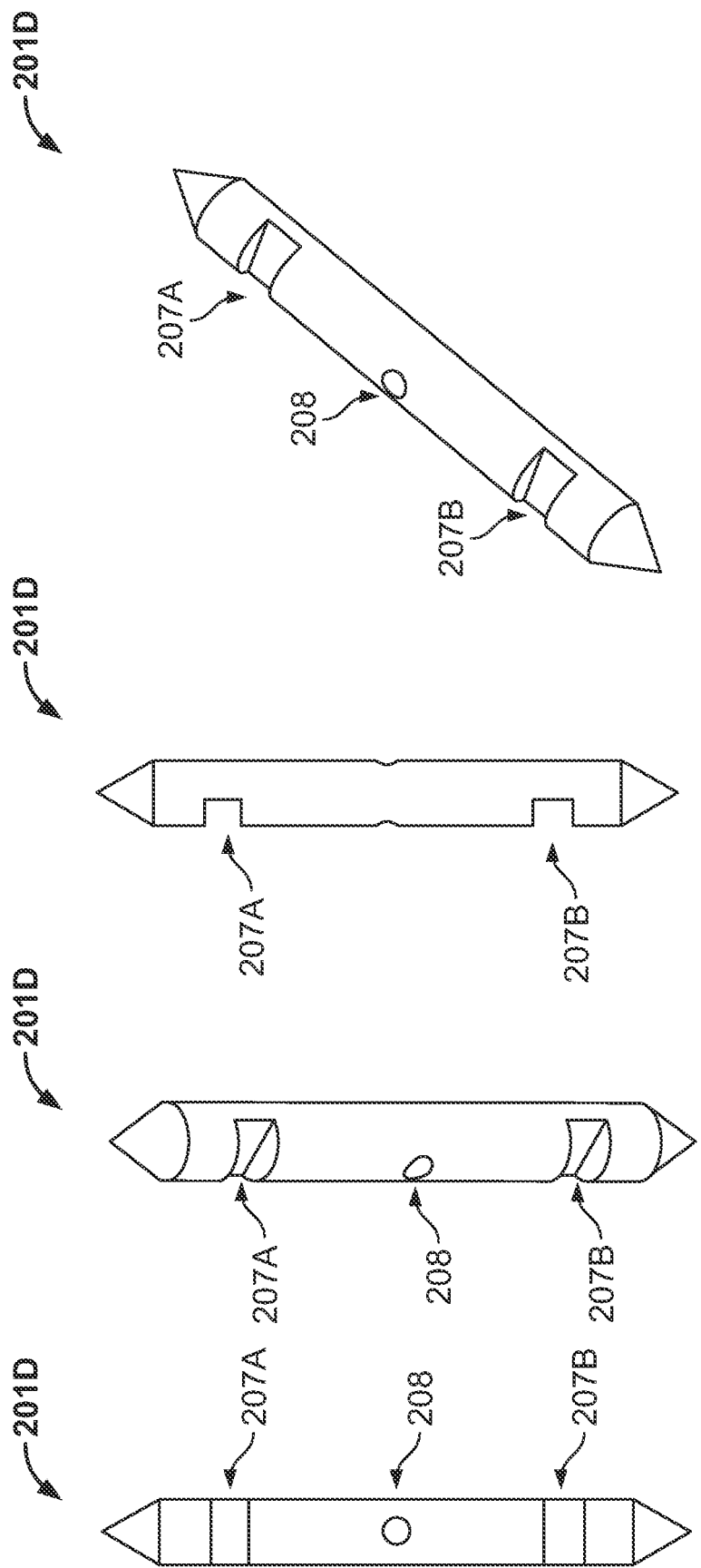
FIG. 5B, FIG. 5C, FIG. 5D, and FIG. 5E depict an embodiment of a straight needle for the suturing device.

As shown in FIG. 5A, the needle 201 can be a needle 201C that has a concave shape. FIG. 5B, FIG. 5C, FIG. 5D, and FIG. 5E depict an embodiment of a needle 201D that has a straight shape. In some embodiments, the needle 201C and the needle 201D can include a hole 208. In some embodiments, the hole 208 can be used for needle-thread joining by drilling a hole in the middle of the needle 201C or the needle 201D, inserting the thread (e.g., thread 16) into the hole 208, and deforming the hole 208 with the help of a suitable die geometry attached to a press. In some embodiments, the needle 201 and the thread 16 can be joined by using a proper adhesive instead of deforming the hole 208.

FIG. 5F, FIG. 5G, FIG. 5H, and FIG. 5I depict an embodiment of a needle 201E that includes a channel 209. The channel 209 can be an open channel feature-based joining of the needle 201 and thread 16. The channel 209 can be opened in the middle region of the needle 201E. A thread can be placed within the channel 209, and the channel 209 can be deformed onto the thread with the help of a suitable die geometry attached to a press. In some embodiments, the needle 201 and the thread 16 can be joined by using a proper adhesive instead of deforming the channel 209.

Figure 5J:
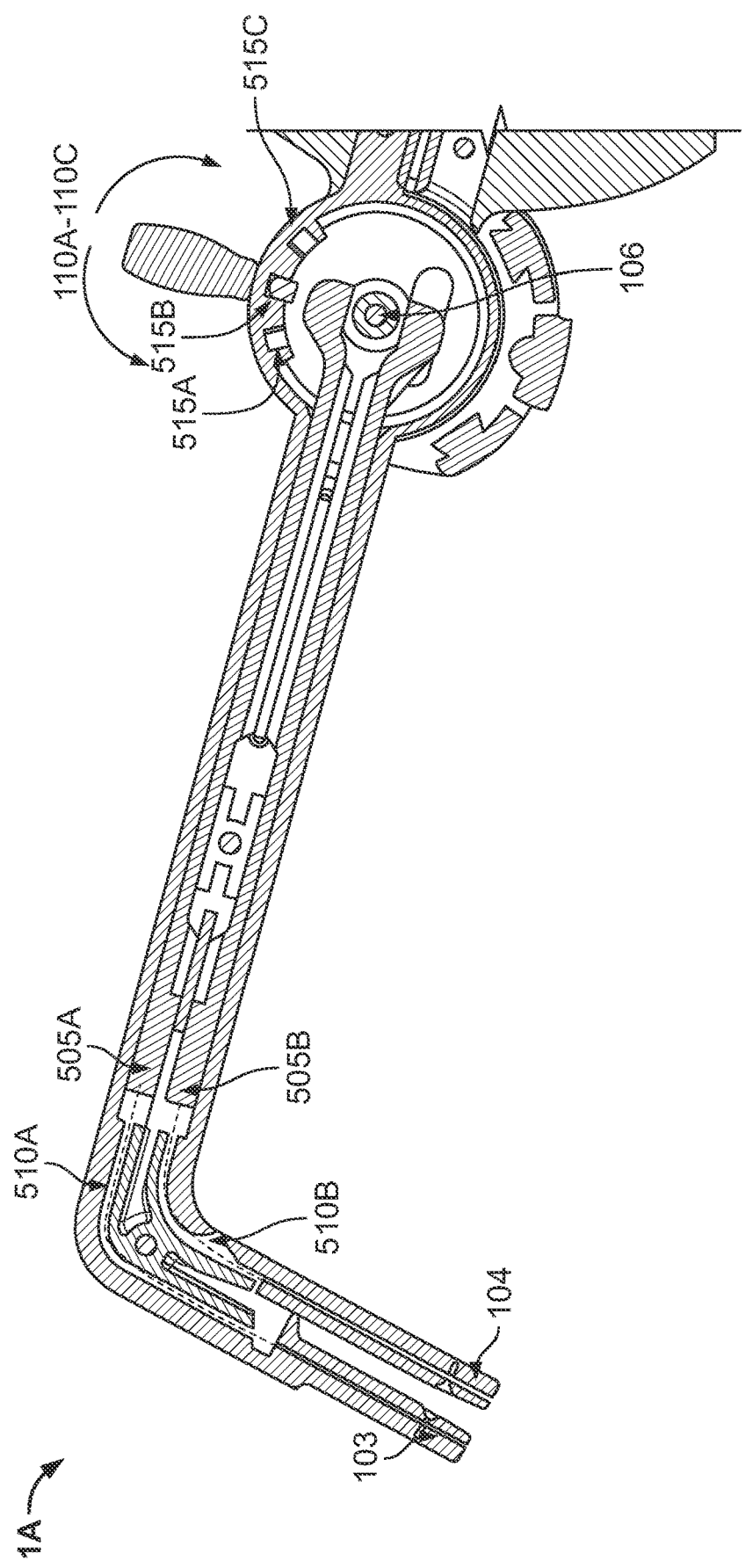
FIG. 5J depicts an embodiment of the suturing device including mechanisms for securing and releasing the needle.

FIG. 5J depicts an embodiment of the needle transfer mechanism 4 of the suturing device 1A. The needle transfer mechanism 4 can enable the needle 201 to be retained in or released from the jaws 5 and 6 with the help of back and forth moving flexible plates (e.g., the first control bar 505A and the second control bar 505B and/or the first grasping member 510A and the second grasping member 510B). These plates can be pulled or pushed by a control lever (e.g., lever 3) attached to the plates. In some embodiments, the first control bar 505A, the second control bar 505B, the first grasping member 510A, and the second grasping member 510B can be located in the fixed arm 7. In some embodiments, the first control bar 505A, the second control bar 505B, the first grasping member 510A, and the second grasping member 510B can be located in the fixed jaw 5 and the fixed arm 7.

In reference to FIG. 5J, the needle transfer mechanism 4 includes the first control bar 505A and the second control bar 505B. In some embodiments, the first control bar 505A and the second control bar 505B extend within respective channels in the fixed arm 7. In some embodiments, the first control bar 505A extends within a channel through the fixed jaw 5. In some embodiments, the second control bar 505B extends within a channel through the movable jaw 6.

The control bars can advance or retract independently within their respective channels. In some embodiments, the first control bar 505A can advance towards the first grasping slot 103 and towards the first notch 207A or the second notch 207B of the needle 201 disposed in the first grasping slot 103 to secure the needle 201 in the first grasping slot 103. In some embodiments, the first control bar 505A can retract from the first grasping slot 103 and the first notch 207A or the second notch 207B to release the needle 201 from the first grasping slot 103. In some embodiments, the second control bar 505B can advance towards the second grasping slot 104 and towards the first notch 207A or the second notch 207B of the needle 201 disposed in the second grasping slot 104 to secure the needle 201 in the second grasping slot 104. In some embodiments, the second control bar 505B can retract from the second grasping slot 104 and the first notch 207A or the second notch 207B to release the needle 201 from the second grasping slot 104. For example, the control bars can be pulled within their respective channels.

The needle transfer mechanism 4 can include a switching joint 106 that is coupled to the lever 3, the first control bar 505A, and the second control bar 505B. In some embodiments, the switching joint 106 is disposed on the fixed arm 7. Movement of the lever 3 can cause movement of the switching joint 106, which can cause movement of the first control bar 505A and the second control bar 505B to secure or release the needle 201 in the first grasping slot 103 or the second grasping slot 104. For example, the switching joint 106 can be a mechanical joint for connecting two components and allowing them to move relative to each other.

In some embodiments, the lever 3 can rotate or move the switching joint 106 to move the first control bar 505A and the second control bar 505B. For example, the lever 3 can spin the switching joint 106 and thus push or pull the control bars connected to the switching joint 106. In this manner, the movement of the lever 3 can advance the first control bar 505A towards the first grasping slot 103 while retracting the second control bar 505B from the second grasping slot 104 or retract the first control bar 505A away from the first grasping slot 103 while advancing the second control bar 505B towards the second grasping slot 104. For example, the switching joint 106 is rotated clockwise by the lever 3 such that the first control bar 505A is retracted away from the first grasping slot 103 and the second control bar 505B is advanced towards the second grasping slot 104. In another example, the switching joint 106 is rotated counterclockwise by the lever 3 such that the first control bar 505A is advanced towards the first grasping slot 103 and the second control bar 505B is retracted away from the second grasping slot 104.

Figure 5K:
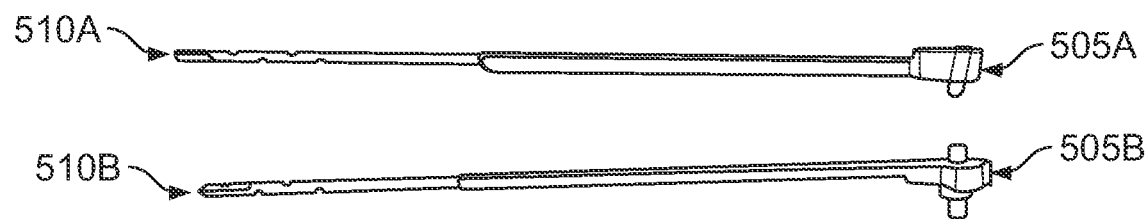
FIG. 5K, FIG. 5L, and FIG. 5M depict an exploded view of an embodiment of the control bars and the grasping members.
Figure 5L:
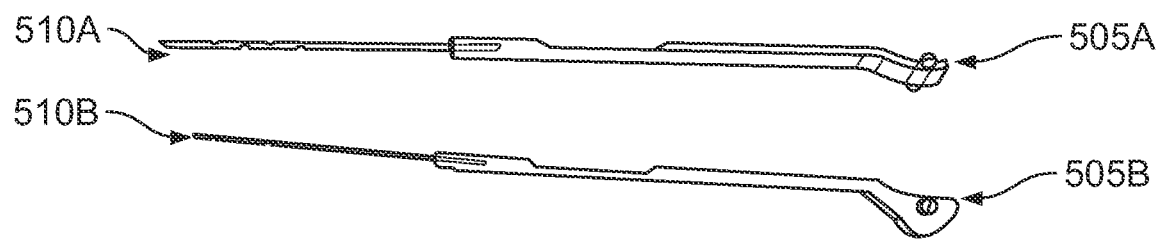
Figure 5M:
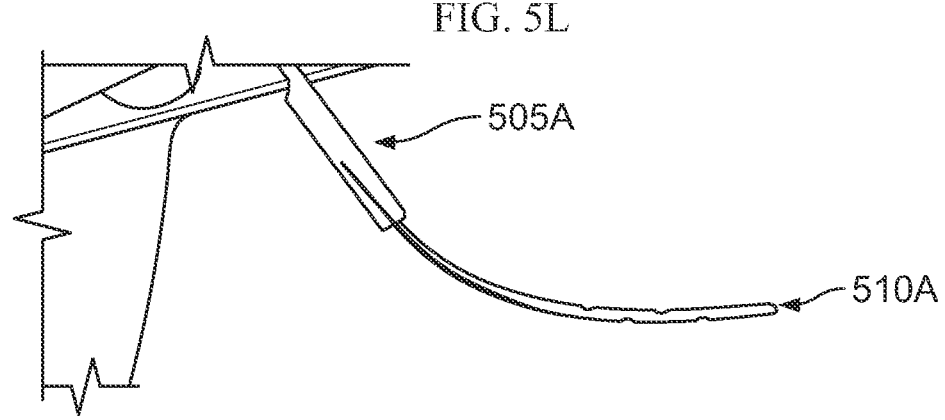

FIG. 5K, FIG. 5L, and FIG. 5M depict an exploded view of an embodiment of the first control bar 505A and the second control bar 505B, and the first grasping member 510A and the second grasping member 510B. In some embodiments, the first grasping member 510A and the second grasping member 510B extend within respective channels in the fixed arm 7. In some embodiments, the first grasping member 510A extends within a channel in the fixed jaw 5. In some embodiments, the first grasping member 510A extends within a channel in the movable jaw 6.

In some embodiments, the control bars are linked or over molded onto a respective grasping member. For example, the first control bar 505A and the first grasping member 510A can be one bar such that the first grasping member 510A is an extension of the first control bar 505A. While not shown, in another example, it is contemplated that the first control bar 505A and the first grasping member 510A can be separate bars such that the first grasping member 510A is coupled to the first control bar 505A. As shown in FIG. 5M, the first grasping member 510A (or the second grasping member 510B) can bend relative to the first control bar 505A (or the second control bar 505B). The highly elastic nature of the first grasping member 510A and the second grasping member 510B allows them to move and function in the angled channels of the jaws 5 and 6.

Referring back to FIG. 5J, in some embodiments, the first control bar 505A can advance the first grasping member 510A towards the first notch 207A or the second notch 207B of the needle 201 disposed in the first grasping slot 103 to secure the needle 201 in the first grasping slot 103. For example, the first control bar 505A can be pushed towards the first grasping slot 103. In this manner, the movement of the first control bar 505A can cause the first grasping member 510A to grasp the first notch 207A or the second notch 207B to grasp the needle 201 in the first grasping slot 103.

In some embodiments, the first control bar 505A can retract the first grasping member 510A from the first notch 207A or the second notch 207B to release the needle 201 from the first grasping slot 103. For example, the first control bar 505A can be pulled away from the first grasping slot 103. In this manner, the movement of the first control bar 505A can cause the first grasping member 510A to release the first notch 207A or the second notch 207B to release the needle 201 from the first grasping slot 103.

In some embodiments, the second control bar 505B can advance the second grasping member 510B towards the first notch 207A or the second notch 207B of the needle 201 disposed in the second grasping slot 104 to grasp the needle 201 in the second grasping slot 104. For example, the second control bar 505B can be pushed towards the second grasping slot 104. In this manner, the movement of the second control bar 505B can cause the second grasping member 510B to grasp the first notch 207A or the second notch 207B of the needle 201 to grasp the needle 201 in the second grasping slot 104.

In some embodiments, the second control bar 505B can retract the second grasping member 510B from the first notch 207A or the second notch 207B to release the needle 201 from the second grasping slot 104. For example, the second control bar 505B can be pulled away from the second grasping slot 104. In this manner, the movement of the second control bar 505B can cause the second grasping member 510B to release the first notch 207A or the second notch 207B to release the needle 201 from the second grasping slot 104. In some embodiments, the control bars or the grasping members have different lengths. For example, the first grasping member 510A or the first control bar 505A can be longer than the second grasping member 510B or the second control bar 505B because they must extend a greater distance to reach the first grasping slot 103. In another example, the second grasping member 510B or the second control bar 505B can be longer than the first grasping member 510A or the first control bar 505A because they must be able to bend with the movable jaw 6 that comprises the second grasping slot 104.

The lever 3 can move to the first position 110A to move the switching joint 106 to advance the first control bar 505A to advance the first grasping member 510A to grasp the needle 201 in the first grasping slot 103 and to retract the second control bar 505B to retract the second grasping member 510B to release the needle 201 from the second grasping slot 104. For example, as shown in FIG. 5J, the lever 3 can rotate the switching joint 106 counterclockwise to move into the first position 110A. In some embodiments, the lever 3 can move to the first position 110A to move the switching joint 106 to advance the first control bar 505A to advance the first grasping member 510A to grasp the needle 201 in the first grasping slot 103. For example, as shown in FIG. 5J, by moving the lever 3 to the first position 110A, the switching joint 106 can be rotated in the counterclockwise direction, which can advance the first control bar 505A to the left and retract the second control bar 505B to the right such that the first control bar 505A causes the first grasping member 510A to grasp the needle 201 in the first grasping slot 103 and the second control bar 505B causes the second grasping member 510B to release the needle 201 from the second grasping slot 104. The lever 3 can include the security notch 515A of the suturing device 1 to maintain the lever 3 in the first position 110A so that the lever 3 is not accidently moved to a different position during use (e.g., during surgery).

The lever 3 can move to the second position 110B to move the switching joint 106 to retract the first control bar 505A to retract the first grasping member 510A to release the needle 201 from the first grasping slot 103 and to retract the second control bar 505B to retract the second grasping member 510B to release the needle 201 from the second grasping slot 104. In some embodiments, the lever 3 can move to the second position 1101B to move the switching joint 106 to retract the first control bar 505A to retract the first grasping member 510A to release the needle 201 from the first grasping slot 103.

For example, as shown in FIG. 5J, if the lever 3 is moved to second position 110B from the first position 110A, the switching joint 106 can be rotated in the clockwise direction, which can partially retract the first control bar 505A to the right and partially advance the second control bar 505B to the left such that the first control bar 505A and the second control bar 505B are in an inactive position that prevents the first grasping slot 103 and the second grasping slot 104 from grasping the needle 201.

In another example, as shown in FIG. 5J, if the lever 3 is moved to the second position 1101B from the third position 110C, the switching joint 106 can be rotated in the counterclockwise direction, which can partially advance the first control bar 505A to the left and partially retract the second control bar 505B to the right such that the first control bar 505A and the second control bar 505B are in an inactive position that prevents the first grasping slot 103 and the second grasping slot 104 from grasping the needle 201. The lever 3 can include the security notch 515B of the suturing device 1 to maintain the lever 3 in second position 110B so that the lever 3 is not accidently moved to a different position during use (e.g., during surgery).

The lever 3 can move to the third position 110C to move the switching joint 106 to advance the second control bar 505B to advance the second grasping member 510B to grasp the needle 201 in the second grasping slot 104 and to retract the first control bar 505A to retract the first grasping member 510A to release the needle from the first grasping slot 103. In some embodiments, the lever 3 can move to the third position 110C to move the switching joint 106 to advance the second control bar 505B to advance the second grasping member 510B to grasp the needle in the second grasping slot 104. For example, as shown in FIG. 5J, by moving the lever 3 to the third position 110C from the second position 110B, the switching joint 106 can be rotated in the clockwise direction, which can retract the first control bar 505A to the right and advance the second control bar 505B to the left such that the first control bar 505A causes the first grasping member 510A to release the needle 201 from the first grasping slot 103 and the second control bar 505B causes the second grasping member 510B to grasp the needle 201 in the second grasping slot 104. The lever 3 can include the security notch 515C of the suturing device 1 to maintain the lever 3 in the third position 110C so that the lever 3 is not accidently moved to a different position during use (e.g., during surgery).

Figure 5N:
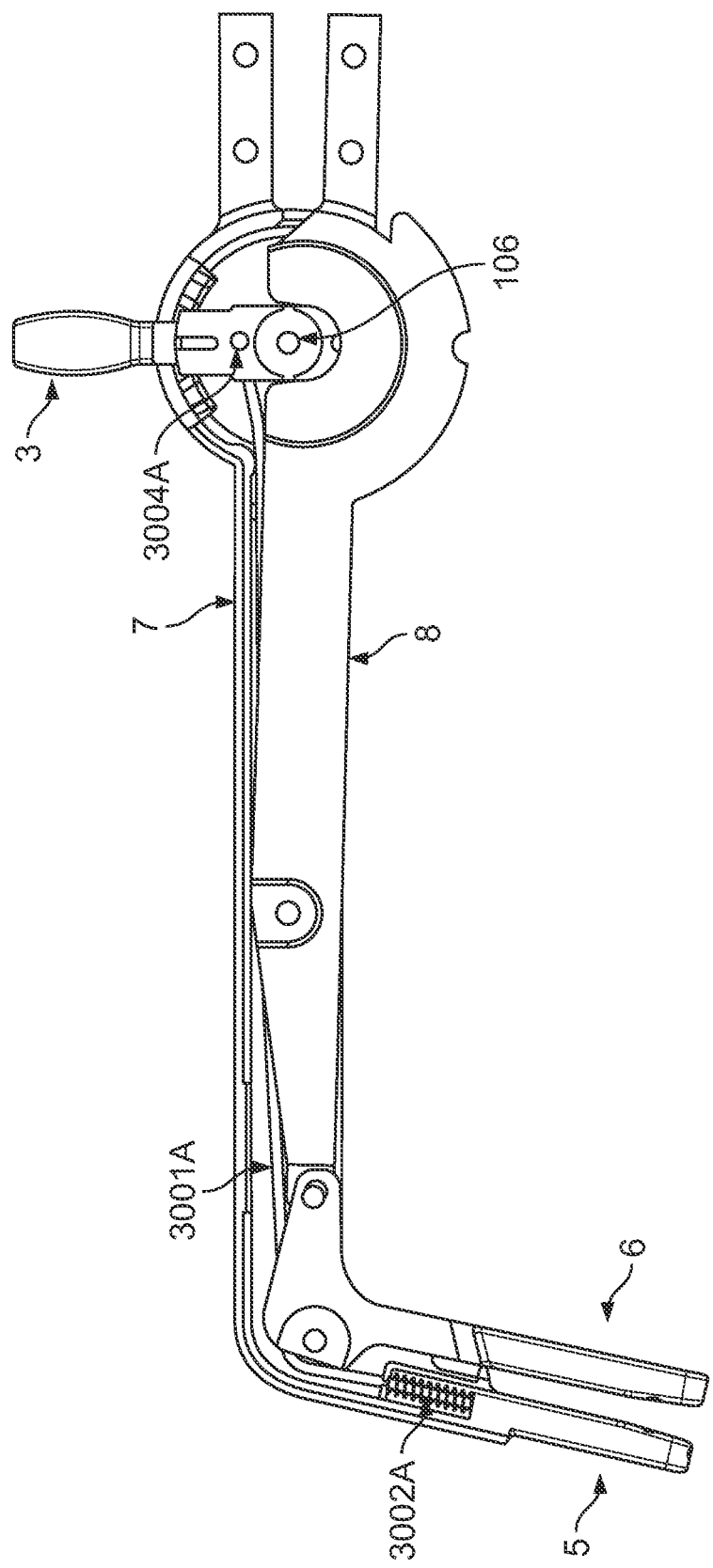

Now referring to FIG. 5N, FIG. 5O, and FIG. 5P, in some embodiments, the needle transfer mechanism 4 includes a cable 3001A, a cable 3001B, a spring 3002A, and a spring 3002B. The cable 3001A and the cable 3001B can be attached to the lever 3 with the stub 3004A and stub 3004B at the end of the cable 3001A and the cable 3001B. In some embodiments, the cable 3001A and the cable 3001B extend within respective channels in the fixed arm 7. In some embodiments, the cable 3001A extends within a channel in the fixed jaw 5. In some embodiments, the cable 3001B extends within a channel in the movable jaw 6. In some embodiments, the spring 3002A is located within the fixed jaw 5. In some embodiments, the spring 3002B is located within the movable jaw 6.

The lever 3 can be rotated along the switching joint 106. There can be 3 distinct positions in which the lever 3 can be rotated. The lever 3 can be designed so that a predetermined amount of user-applied force is needed to change positions of the lever 3. In some embodiments, the predetermined amount of user-applied force is based on the tension of the cable 3001A and the cable 3001B. The geometric features 3005A, 3005B, 3007A, 3007B, 3006A, and 3006B of the fixed arm 7 can be used to route the cable 3001A and the cable 3001B in an optimal path. The spring 3002A and the spring 3002B can be placed on the cylindrical piston 3003A and the cylindrical piston 3003B and retained by machine elements (e.g., machine element 3008B retains spring 3002B), which can include rings, pins, etc. or structural features such as protrusions. In some embodiments, the cylindrical piston 3003A is located within the fixed jaw 5. In some embodiments, the cylindrical piston 3003B is located within the movable jaw 6.

In some embodiments, a proximal end (e.g., proximal to the operator) of the pistons 3003A and 3003B are attached to the cables 3001A and 3001B, respectively. In some embodiments, a distal end of the pistons 3003A and 3003B can be designed and shaped to engage and grasp the needle 201. In some embodiments, the distal end of the piston 3003A can be advanced to engage and grasp the needle 201 in the fixed jaw 5. In some embodiments, the distal end of the piston 3003A can be retracted to disengage and release the needle 201 in the fixed jaw 5. In some embodiments, the distal end of the piston 3003B can be advanced to engage and grasp the needle 201 in the movable jaw 6. In some embodiments, the distal end of the piston 3003B can be retracted to disengage and release the needle 201 in the movable jaw 6.

In some embodiments, the lever 3 can be in a middle position (e.g., similar to the second position 110B) as shown in FIG. 5N and FIG. 5O. In the middle position, both cables 3001A and 3001B can be semi-pulled, both springs 3002A and 3002B can be semi-compressed and both pistons 3003A and 3003B can be semi-retracted. In some embodiments, when the pistons 3003A and 3003B are semi-retracted, the pistons 3003A and 3003B are disengaged from the needle 201 such that the needle 201 can be released from both the fixed jaw 5 and the movable jaw 6. In some embodiments, when the pistons 3003A and 3003B are semi-retracted, the pistons 3003A and 3003B engage the needle 201 such that the needle 201 is secured in both the fixed jaw 5 and the movable jaw 6. In some embodiments, with the jaws 5 and 6 in the closed position (e.g., moveable jaw 6 moved towards the fixed jaw 5), the needle 201 can be retained by both jaws 5 and 6 and the suturing device (e.g., device 1A or 1B) can be locked.

In some embodiments, the lever 3 can be in a forward position (e.g., similar to the first position 110A). In the forward position, the lever 3 can cause the spring 3002A corresponding to the fixed jaw 5 to be fully released by the cable 3001A, which can cause the piston 3003A to move forward from the spring force, and the needle 201 can be retained in the fixed jaw 5. At the same time, the lever 3 can cause the spring 3002B corresponding to the movable jaw 6 to be pulled by the cable 3001B and fully compress, which can cause the piston 3003B to be pulled by the cable 3001B, and the needle 201 to be released from the movable jaw 6.

In some embodiments, the lever 3 can be in a backward position (e.g., similar to the third position 110C). In the backward position, the lever 3 can cause the spring 3002B corresponding to the movable jaw 6 to be fully released by the cable 3001B, which can cause the piston 3003B to move forward from the spring force, and the needle 201 can be retained by the movable jaw 6. At the same time, the lever 3 can cause the spring 3002A corresponding to the fixed jaw 5 to be pulled by the cable 3001A and fully compressed, which can cause the piston 3003A to be pulled by the cable 3001A, and the needle 201 to be released from the fixed jaw 5.

Figure 6C:
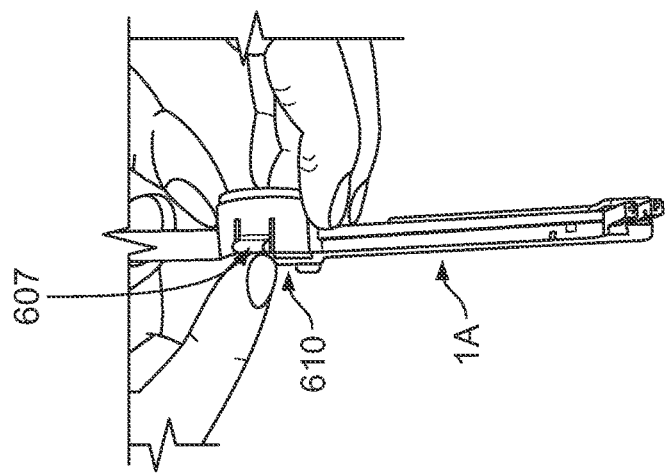
FIG. 6A, FIG. 6B, and FIG. 6C depict an embodiment of the suturing device including the stopper in an activated position.
Figure 6B:
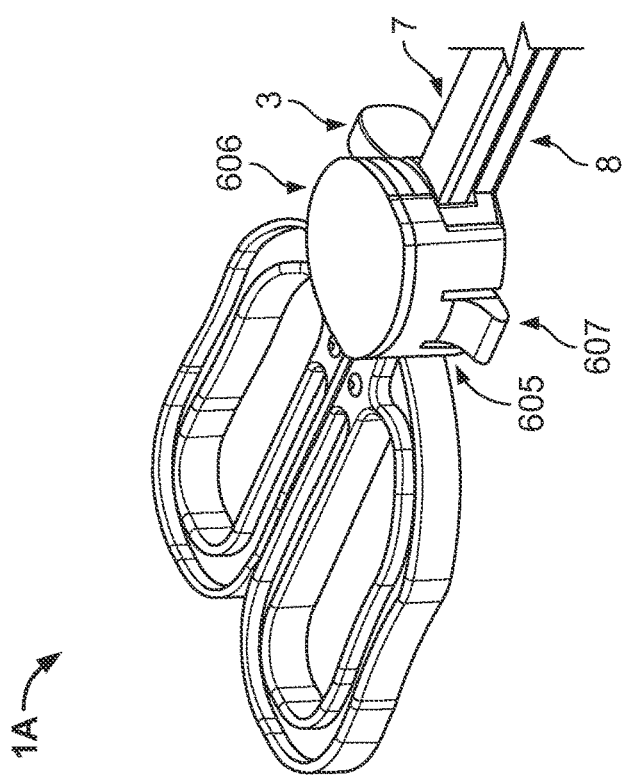
Figure 6A:
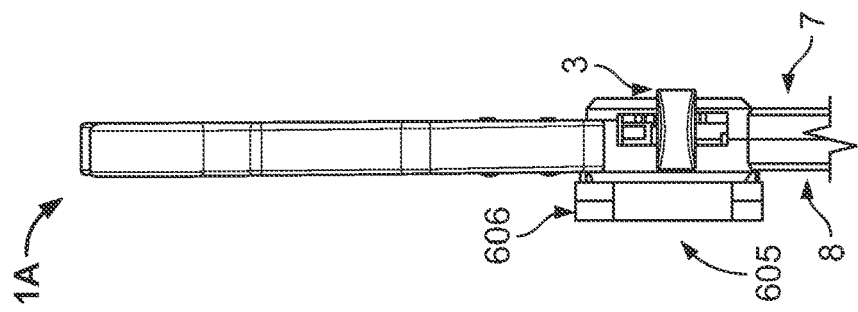

FIG. 6A, FIG. 6B, and FIG. 6C depict an embodiment of the suturing device 1A including a stopper 605 in an activated position. In terms of safety, if the movable jaw 6 moves when the lever 3 is in the second position 110B, the needle 201 might fall out because the needle 201 is not secured in either the first grasping slot 103 or the second grasping slot 104. To address this problem, the suturing device 1A includes the stopper 605 to control, based on the position of the lever 3, when the movable arm 8 can move and thus when the movable jaw 6 can move. For example, the stopper 605 can physically impede the movable arm 8 from moving to prevent the needle 201 from falling out.

As shown in FIG. 6A and FIG. 6B, the stopper 605 can be disposed on the movable arm 8 to control when the movable arm 8 can move relative to the fixed arm 7. For example, the stopper 605 can grasp or secure the fixed arm 7 to prevent the movable arm 8 from moving to prevent the needle 201 from falling out. The stopper 605 can be disposed on the movable arm 8 and adjacent to the lever 3 on the fixed arm 7 to control the movable arm 8 based on the position of the lever 3. In some embodiments, the stopper 605 is covered by a lid 606 to protect the stopper 605.

The stopper 605 can slide on the movable arm 8 between an activated position and a deactivated position. The stopper 605 can control the movement of movable arm 8 when the stopper 605 is in the activated position. In the activated position, the stopper 605 can be positioned closer to the movable arm 8 to be adjacent to the fixed arm 7 to grasp a portion of the fixed arm 7 to control the movement of the movable arm 8 relative to the fixed arm 7.

The stopper 605 can slide on the movable arm 8 from the activated position to the deactivated position in which the stopper 605 does not control the movement of the movable arm 8. For example, the stopper 605 can be a plastic or metal cap that slides on the movable arm 8. In the deactivated position, the stopper 605 can be positioned farther away from the movable arm 8 to avoid grasping the fixed arm 7 and thus avoid controlling the movement of the movable arm 8 relative to the fixed arm 7. The stopper 605 can slide on the movable arm 8 towards the fixed arm 7 and into the activated position to grasp the fixed arm 7 to control the movable arm 8.

As shown in FIG. 6B and FIG. 6C, the stopper 605 can include a flap 607 to secure the stopper 605 in the activated position. For example, the flap 607 can be a bendable extension of the stopper 605. The flap 607 can be snap onto and over an edge of the movable arm 8 to secure the stopper 605 in the activated position. The flap 607 can bend away from the movable arm 8 to release the stopper 605 from the activated position. As shown in FIG. 6C, the operator can bend the flap 607 to release the stopper 605 from the activated position.

Figure 7B:
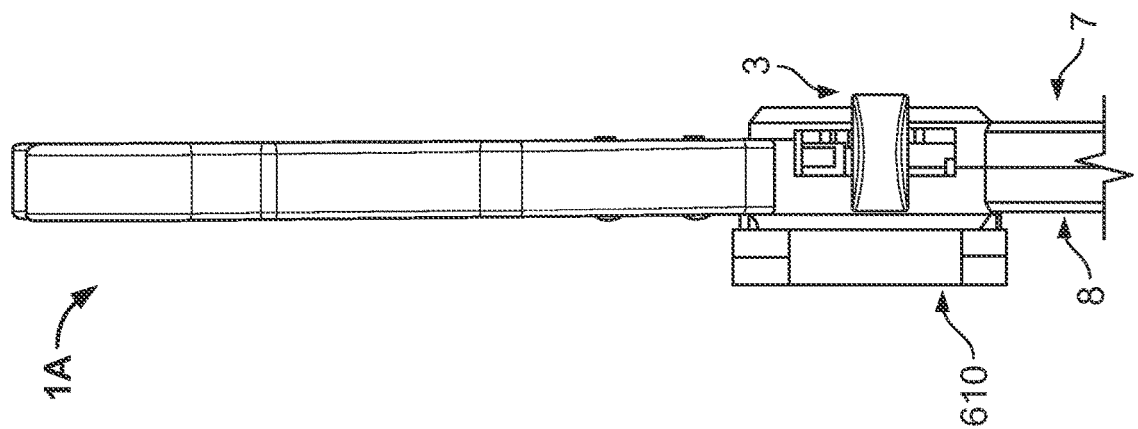
FIG. 7A and FIG. 7B depict an embodiment of the suturing device including the activated stopper and the safety member preventing movement of the movable arm and the movable jaw when the needle is unsecured.
Figure 7A:
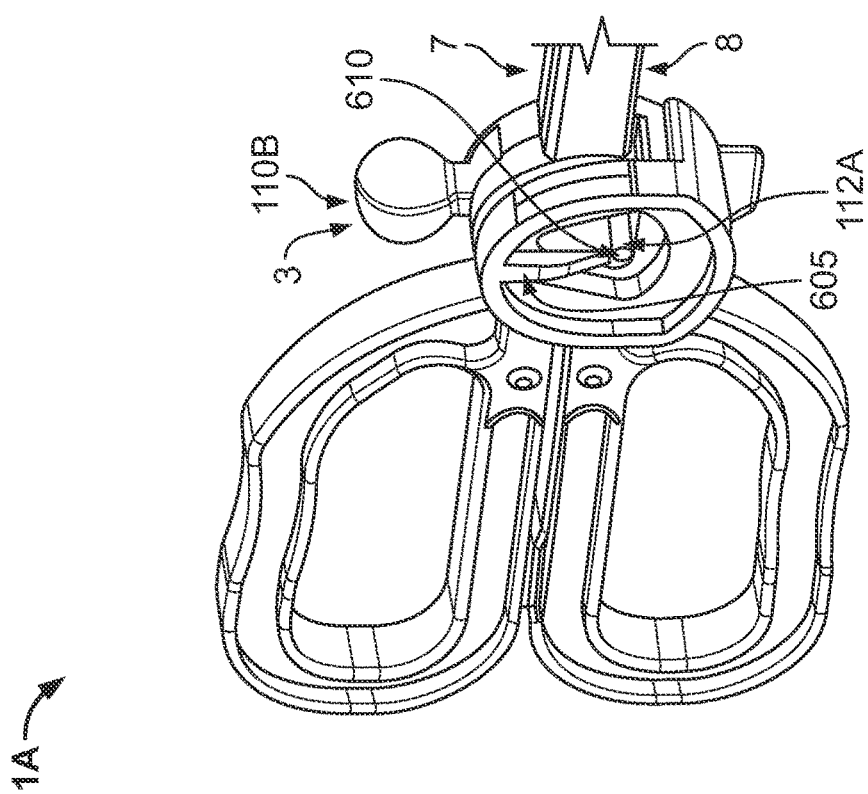

FIG. 7A and FIG. 7B depict an embodiment of the suturing device 1A including the stopper 605 in the activated position and a safety member 610 preventing movement of the movable arm 8 and the movable jaw 6 when the needle 201 is unsecured because the lever 3 is in the second position 110B. In some embodiments, FIG. 7A shows a cross sectional view of the stopper 605 without the lid 606. In some embodiments, the stopper 605 does not have the lid.

Because the stopper 605 is disposed on the movable arm 8, the stopper 605 would move when the movable arm 8 moves. Because the safety member 610 disposed on the fixed arm 7, the stopper 605 would move relative to the safety member 610 when the movable arm 8 moves. Interlocking of the safety member 610 and the stopper 605 would thus prevent the stopper 605 from moving and thus prevent the movable arm 8 from moving to prevent the needle 201 from falling out.

The safety member 610 and the stopper 605 can interlock if the stopper 605 protrudes against the safety member 610. In the activated position, the stopper 605 is positioned to interlock with the safety member 610. For example, the stopper 605 can block or grasp the safety member 610. In some embodiments, when the lever 3 is in the second position 110B (e.g., needle 201 unsecured) and the jaws are closed, the stopper 605 and the safety member 610 interlock to prevent the movable jaw 8 from opening. In some embodiments, when the lever 3 is in the first position 110A or the third position 110C (needle 201 is secured) and the jaws are open, the stopper 605 and the safety member 610 can interlock to prevent the lever 3 from moving to the second position 110B to release the needle 201.

By positioning the stopper 605 and the safety member 610 to interlock when the lever 3 is in the second position 110B and the jaws are closed, the needle 201 would not fall out when it is not secured in neither the first grasping slot 103 or the second grasping slot 104 but the movable arm 8 could move when the needle 201 is secured in either the first grasping slot 103 or the second grasping slot 104. The safety member 610 and the stopper 605 can interlock because the stopper 605 in the activated position protrudes against the safety member 610 when the lever 3 is in the second position 110B. By protruding against the stopper 605, the safety member 610 prevents the movable arm 8 and thus the movable jaw 6 from moving when the lever 3 is in the second position 110B to prevent the needle 201 from falling out.

To position the stopper 605 and the safety member 610 to interlock based on the position of the lever 3, the safety member 610 can be disposed on the second control bar 505B. Since the lever 3 moves the second control bar 505B, the position of the lever 3 determines the position of the safety member 610. The lever 3 in the second position 110B causes the safety member 610 to be in safety position 112A such that the safety member 610 interlocks with the stopper 605 to prevent the movable arm 8 from moving relative to the fixed arm 7 to prevent the needle 201 from falling out.

Figure 8B:
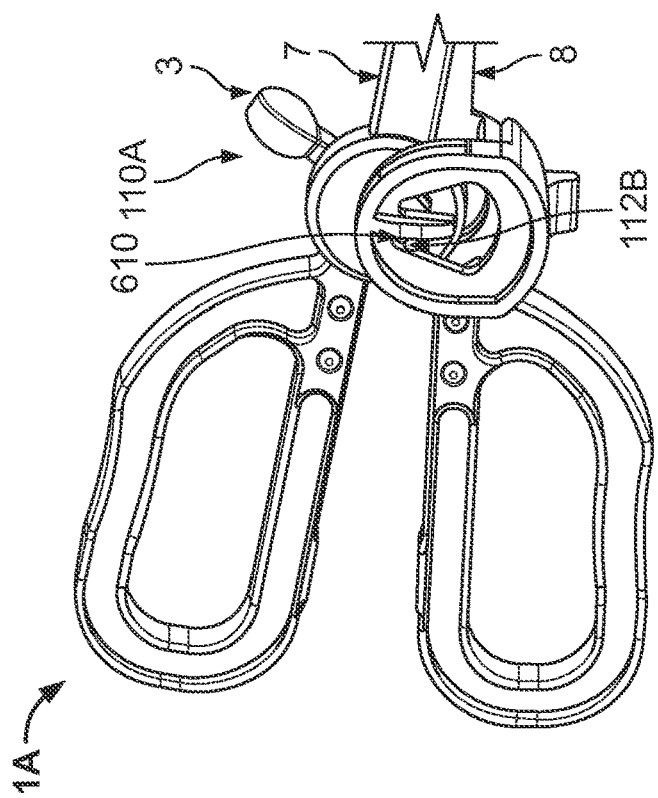
FIG. 8A and FIG. 8B depict an embodiment of the suturing device including the activated stopper allowing movement of the movable arm and the movable jaw when the needle is secured in the first grasping slot.
Figure 8A:
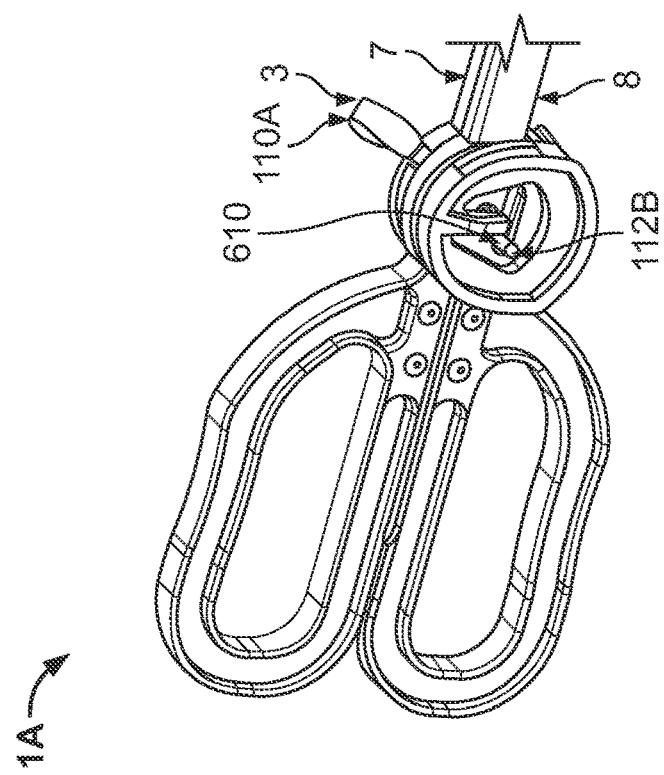

As shown in FIG. 8A and FIG. 8B depict an embodiment of the suturing device 1A including the stopper 605 in the activated position and the safety member 610 allowing movement of the movable arm 8 and the movable jaw 6 when the needle 201 is secured in the first grasping slot 103. The lever 3 in the first position 110A causes the safety member 610 to be in safety position 112B, which would enable the safety member 610 to bypass the stopper 605 so that the movable arm 8 can move.

FIG. 8B depicts the movable arm 8 moving when the lever 3 is in the first position 110A. In the activated position when the movable arm 8 and the movable jaw 6 are open, the stopper 605 can prevent the lever 3 from moving to second position 110B (in which the needle 201 is unsecured) from the first position 110A (in which the needle 201 is secured) to prevent the needle 201 from falling out.

Figure 8D:
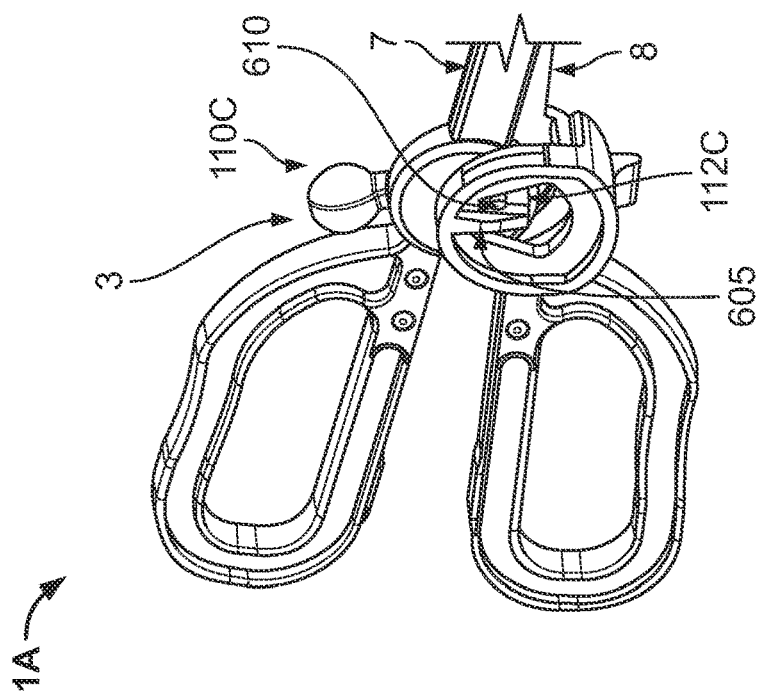
FIG. 8C and FIG. 8D depict an embodiment of the suturing device including the activated stopper allowing movement of the movable arm and the movable jaw when the needle is secured in the second grasping slot.
Figure 8C:
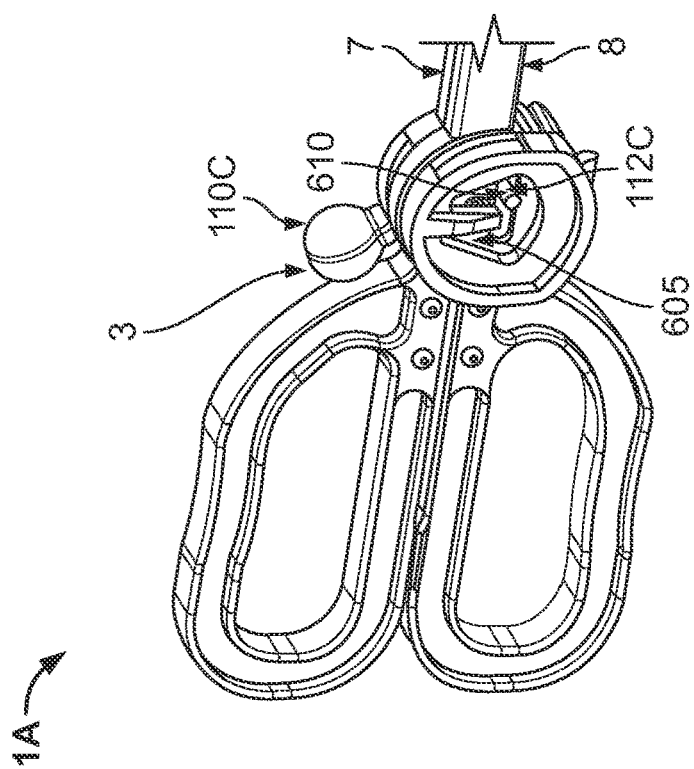

FIG. 8C and FIG. 8D depict an embodiment of the suturing device 1A including the stopper 605 in the activated position allowing movement of the movable arm 8 and the movable jaw 6 when the needle 201 is secured in the second grasping slot 104. The lever 3 in the third position 110C causes the safety member 610 to be in safety position 112C, which would enable the safety member 610 to bypass the stopper 605 so that the movable arm 8 can move.

FIG. 8D depicts the movable arm 8 moving when the lever 3 is in the third position 110C. In the activated position when the movable arm 8 and the movable jaw 6 are open, the stopper 605 can prevent the lever 3 from moving to second position 110B (in which the needle 201 is unsecured) from the third position 110C (in which the needle 201 is secured) to prevent the needle 201 from falling out.

As shown in FIG. 9A, the stopper 605 transitions from an active position to a deactivated position. The operator can bend the flap 607 to release the stopper 605 from the activated position. The operator can pull the stopper 605 away from the safety member 610. The stopper 605 can slide on the movable arm 8 and away from the fixed arm 7 and into the deactivated position. In some embodiments, the operator can keep sliding the stopper 605 until it is removed from the movable arm 8.

Figure 9C:
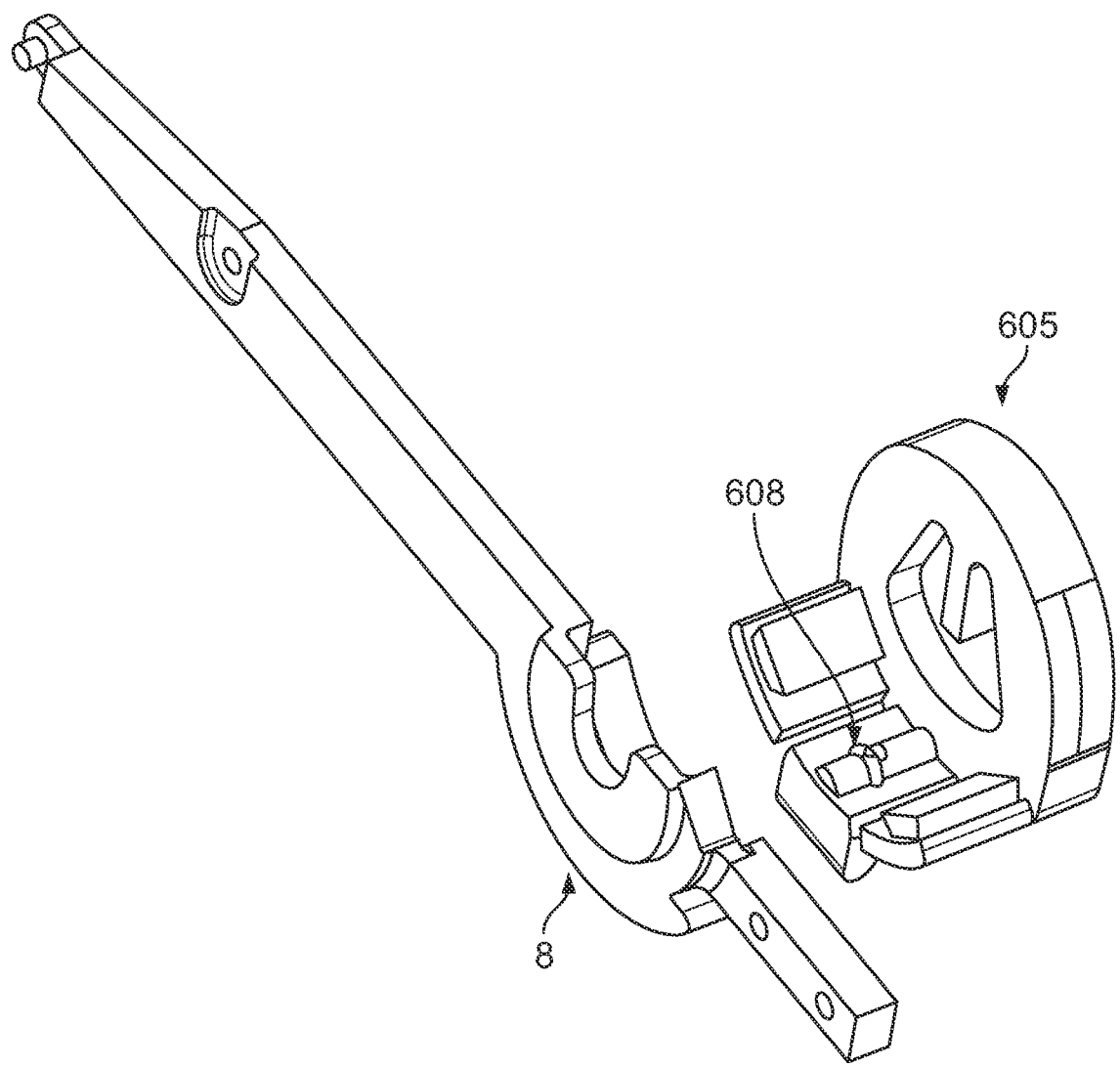

FIG. 9B and FIG. 9C depict exploded views of the stopper 605 and the movable arm 8. As shown in FIG. 9B, the movable arm 8 can include a base region 615. The base region 615 can be integral to the movable arm 8. The base region 615 can be aligned with the lever 3 or the switching joint 106. The position of the stopper 605 relative to the base region 615 can determine whether the stopper 605 is in the activated or deactivated position. In the activated position, the stopper 605 can be positioned closer to the movable arm 8 to be adjacent to the fixed arm 7 to grasp a portion of the fixed arm 7 or interlock with safety member 610 to control the movement of the movable arm 8 relative to the fixed arm 7. In the deactivated position, the stopper 605 can be positioned farther away from the movable arm 8 to avoid grasping the fixed arm 7 and thus avoid controlling the movement of the movable arm 8 relative to the fixed arm 7.

The base region 615 can include a notch 616A and a notch 616B positioned in a sliding channel 617 configured to receive the stopper 605. The notch 616A and the notch 616B can be indents or incisions on the base region 615. The notch 616A can secure the stopper 605 in the activated position and the notch 616B can secure the stopper 605 in the deactivated position. The notch 616A can be disposed away from the side edge of the movable arm 8 to secure the stopper 605 closer to the movable arm 8 in the activated position. The notch 616B can be disposed closer to the side edge of the movable arm 8 to secure the stopper 605 further away from the movable arm 8 in the deactivated position.

As shown in FIG. 9C, the stopper 605 can include a protrusion 608 that can be secured in the notch 616A or the notch 616B. For example, the protrusion 608 can be a bump or tube that protrudes from the stopper 605. The protrusion 608 can slide or snap into the notch 616A or the notch 616B to be secured. The protrusion 608 can slide into the notch 616A to secure the stopper 605 in the activated position. The protrusion 608 can slide into the notch 616B to secure the stopper 605 in the deactivated position.

Figure 9E:
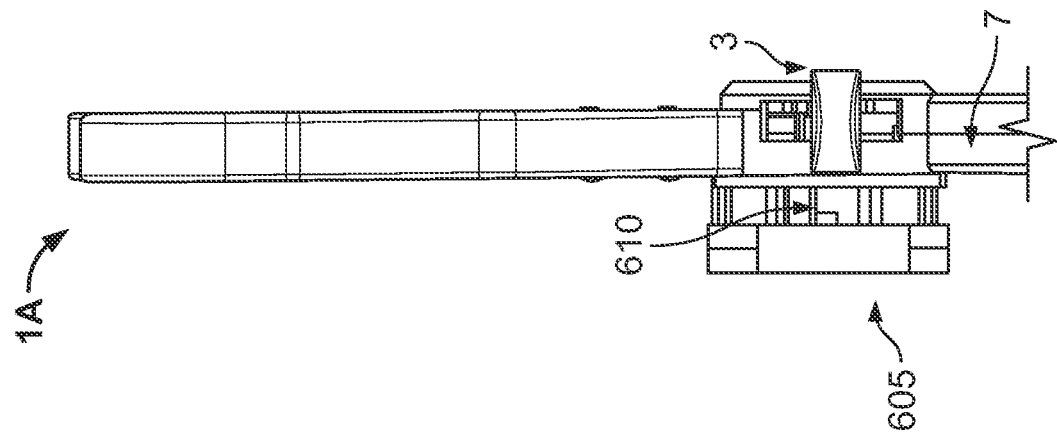
FIG. 9D and FIG. 9E depict an embodiment of the suturing device including the stopper in the deactivated position.
Figure 9D:
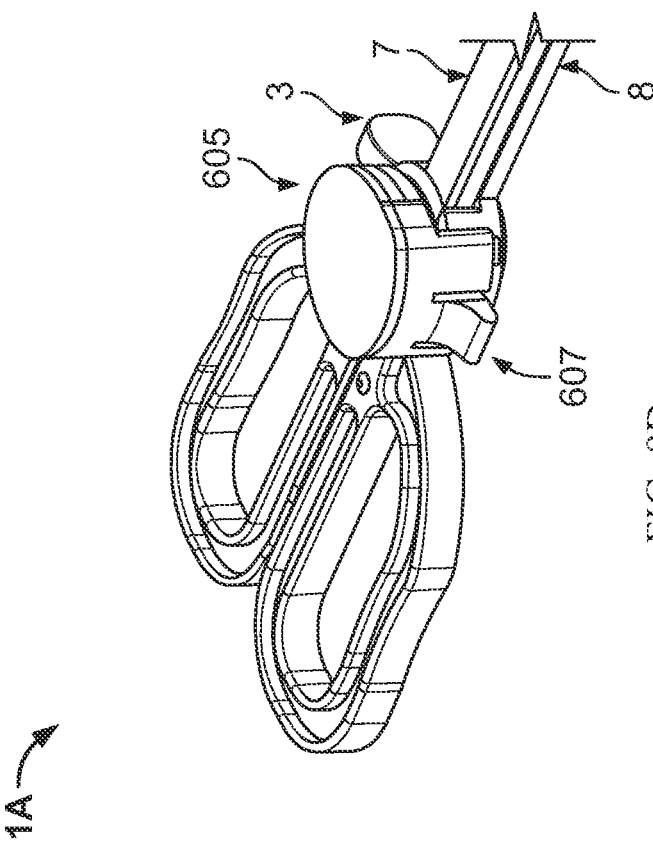

As shown in FIG. 9D and FIG. 9E, in the deactivated position, the stopper 605 is positioned away from the fixed arm 7 and the safety member 610 such that the stopper 605 and the safety member 610 cannot interlock. Regardless of the position of the lever 3 and thus the safety member 610, the safety member 610 can be positioned to not protrude against the stopper 605 when the stopper 605 is in the deactivated position.

FIG. 10A and FIG. 10B depict an embodiment of the suturing device 1A including the stopper 605 in the deactivated position to allow the movable arm 8 to move even when the needle 201 is unsecured. When the stopper 605 is in the deactivated position, the movable arm 8 can move when the lever 3 is in the second position 110B and the needle 201 is not secured in either the first grasping slot 103 or the second grasping slot 104. By allowing the movable arm 8 to move when the lever 3 is in the second position 110B, the needle 201 can be released, such as at the end of a suturing operation. In the deactivated position, the stopper 605 can allow the lever 3 to move to the second position 110B from the first position 110A or the third position 110C, such as to load, unload, and reload the needle 201 in the loading apparatus 10 described below.

Figure 11A:
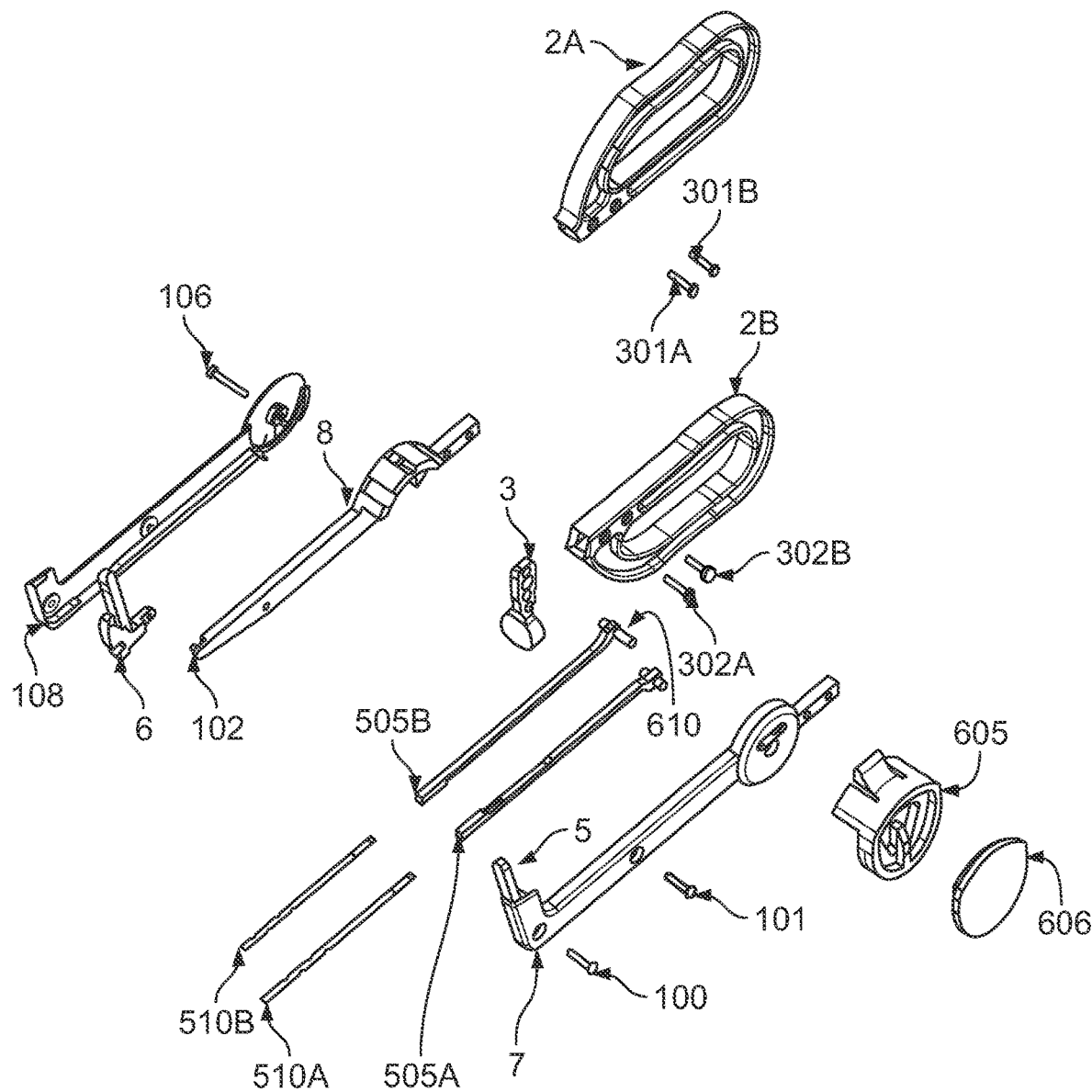
FIG. 11A depicts an exploded view of an embodiment of the suturing device.

FIG. 11A depicts an embodiment of the suturing device 1A. In some embodiments, the first handle 2A is coupled to the movable arm 8 with a set of first fasteners 301A and 301B. In some embodiments, the second handle 2B is coupled to the fixed arm 7 with a set of second fasteners 302A and 302B.

FIG. 11B and FIG. 11C depict an embodiment of the suturing device 1A with attachment member 1105A and attachment member 1105B. In some embodiments, the attachment member 1105A or 1105B has the needle 201 already preloaded. As shown in FIG. 11B, the attachment member 1105A can be configured to be attached to the movable jaw 6 that is configured to receive the attachment member 1105A. As shown in FIG. 11C, the attachment member 1105B can be configured to be attached to the fixed jaw 5 that is configured to receive the attachment member 1105B. For example, instead of having to load the needle 201 into the second grasping slot 104, the attachment member 1105A with the needle 201 can be attached to the movable jaw 6 of the suturing device 1A. In another example, instead of having to load the needle 201 into the first grasping slot 103, the attachment member 1105B with the needle 201 can be attached to the fixed jaw 5 of the suturing device 1A. In some embodiments, at the conclusion of a suturing operation, the attachment member 1105A or the attachment member 1105B can be removed with the needle 201, and another attachment member 1105A or the attachment member 1105B with a replacement needle 201 can be attached to the fixed jaw 5 or the movable jaw 6. In some embodiments, the operator can use the same needle 201 for suturing for more than one suture. For example, if the procedure requires so, the operator can also make suture after suture (sequential) with the same needle 201, which is called Z-suture or 8-figure suture.

Figure 12A:
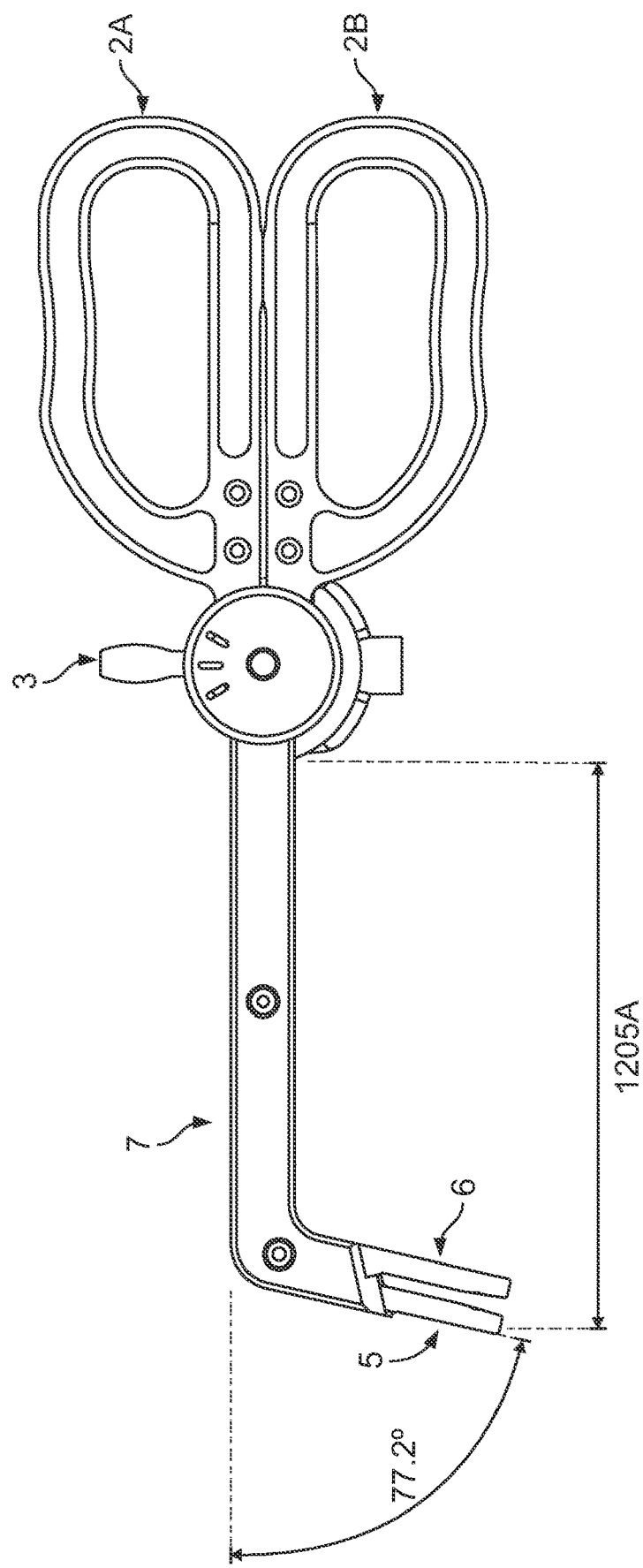
FIG. 12A and FIG. 12B depict embodiments of shapes of suturing devices.
Figure 12B:
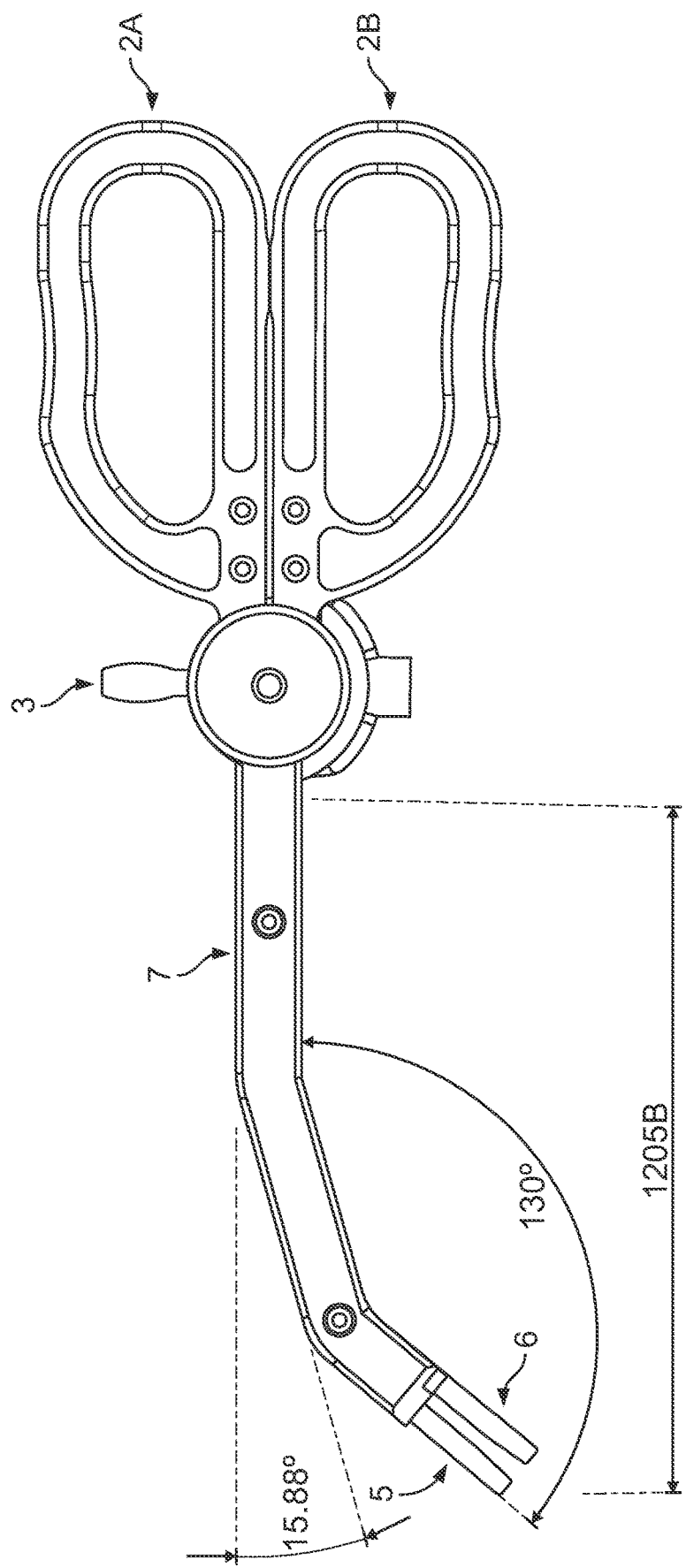

FIG. 12A and FIG. 12B depict embodiments of shapes of suturing devices (e.g., suturing device 1A or suturing device 1B). The suturing devices can be in various sizes, shapes, and angles that are optimized based on the anatomy for which the suturing devices are to be used. The suturing devices can have sizes and angles optimized for the repair of pelvic floor disorders safely due to positional accuracy and in a minimally invasive way.

The size and angles of the devices can be selected according to the target ligament each device is designed to reach for suturing and according to the pathway each device needs to travel in order to reach the target ligament. For example, the pathway can have obstacles such as hard-bony tissues and soft tissues. The sizes and angles can ensure that the surgical methods for using the suturing devices can maneuver the suturing devices through the pathway such that the devices are delivered to their target ligament in the least invasive way. For example, the area of the pathway can be in the pelvic cavity, which can be very similar from patient to patient with minimal standard deviation. As such, the calculation can be accurate across patients even though they might have different bodily parameters (e.g., height, weight, etc.). The sizes and angles can be selected according to the target ligament. For example, once the device is delivered to the target ligament, the outer contour of the fixed jaw 5 can be used for positional accuracy.

The suturing devices can have a length such that during operation of the suturing device, the handle 2A and 2B can be positioned outside the cavity while the length defines a portion of the suturing device that can be positioned inside the cavity. For example, the suturing devices can have a length and angles for transvaginal approaches or procedures. As shown in FIG. 12A, the fixed jaw 5 can extend relative to the fixed arm 7 at an angle of 77.2 degrees. A length 1205A can be measured from the tip of the fixed jaw 5 and the fixed arm 7. As shown in FIG. 12B, the fixed arm 7 can have a distal portion that extends relative a proximal portion at an angle of 15.88 degrees. The fixed jaw 5 can extend relative to the fixed arm 7 at angle of 130 degrees. The fixed jaw 5 and the fixed arm 7 can have a length 1205B. It is contemplated that the suturing devices can be modified to modify the sizes, shapes, and angles to optimize the suturing device for specific cavities and operations.

Figure 13A:
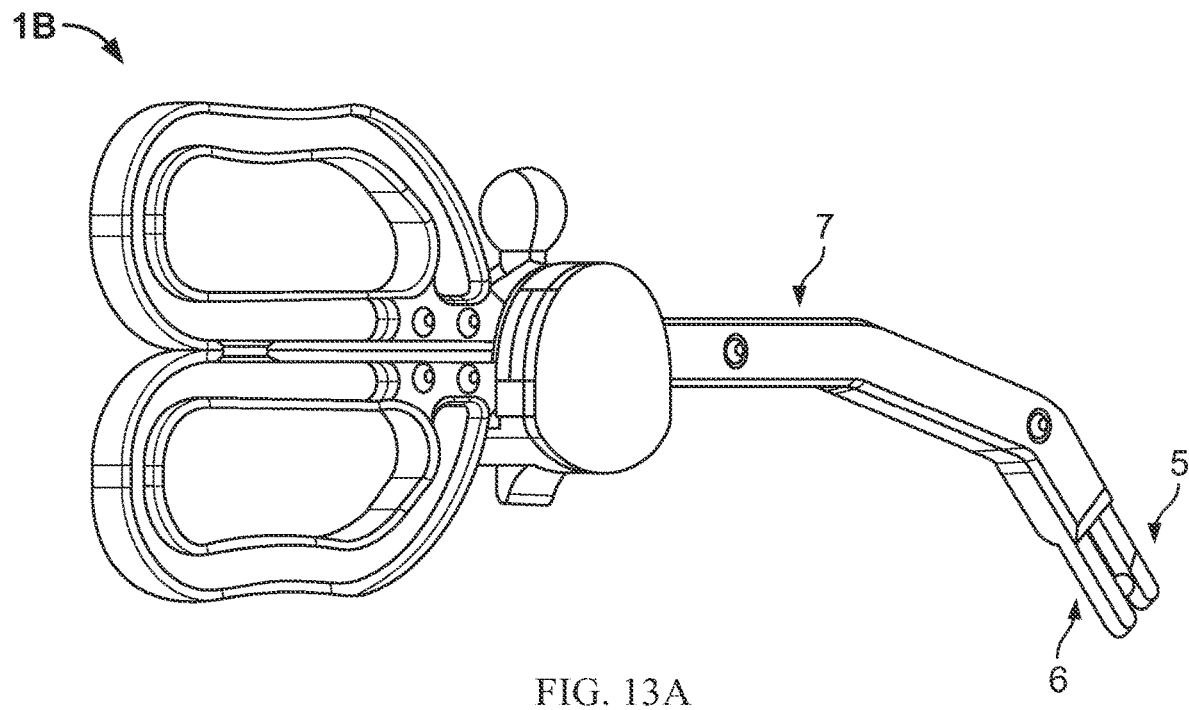
FIG. 13A and FIG. 13B depict an embodiment of the suturing device.
Figure 13B:
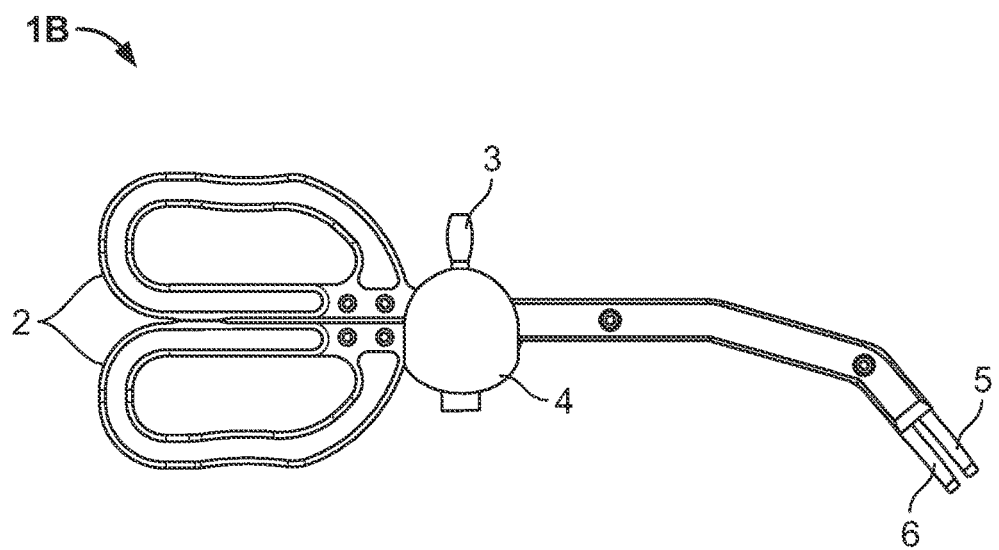
Figure 13C:
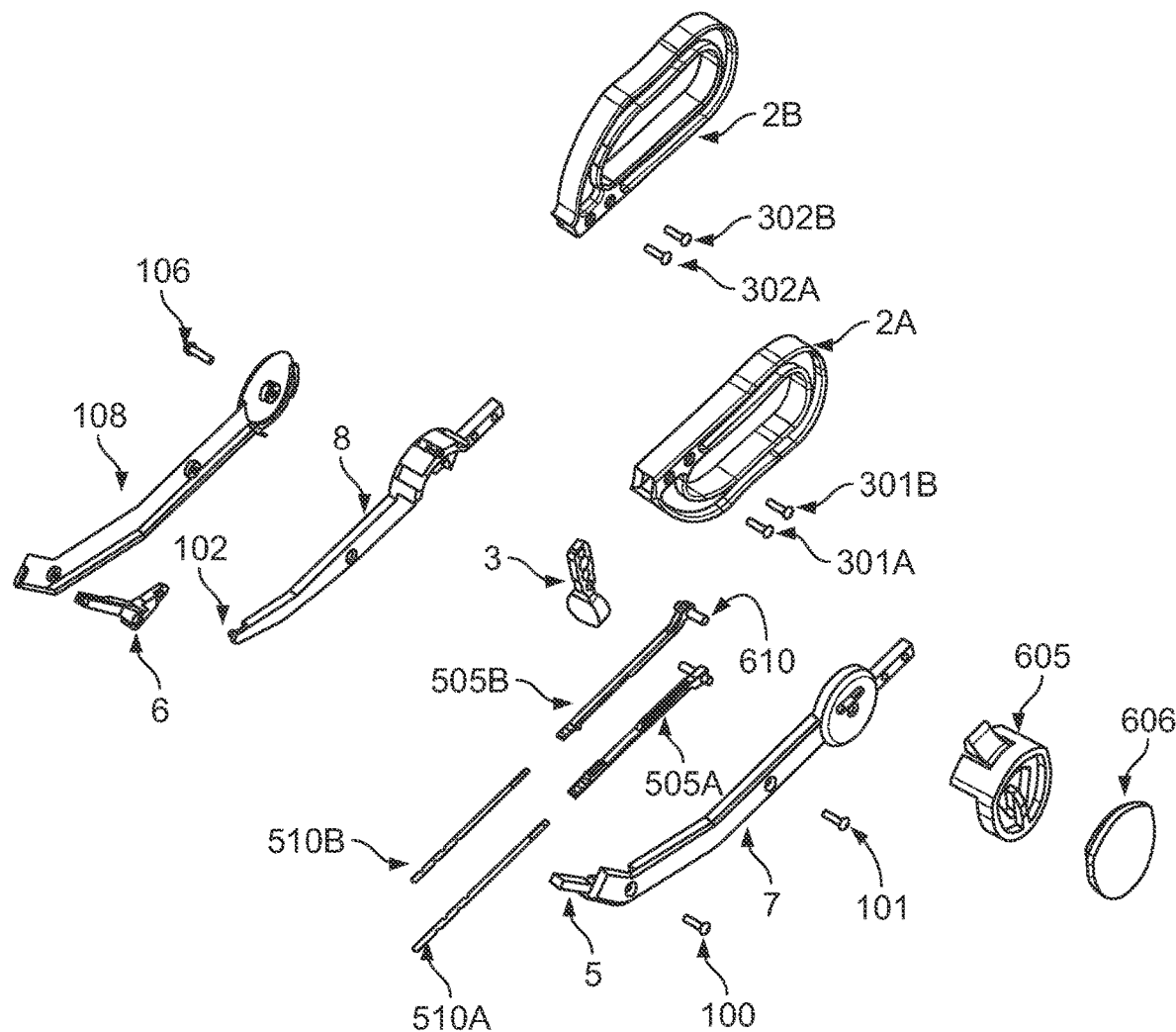
FIG. 13C depicts an exploded view of an embodiment of the suturing device.

FIG. 13A, FIG. 13B, and FIG. 13C depict an embodiment of the suturing device 1B. The suturing device 1B can be similar to the suturing device 1A but differs in that its components have a different angle, size, and shape to optimize the suturing device 1B for the anatomy for which the suturing device 1B is to be used. FIG. 13C depicts an exploded view of an embodiment of the suturing device 1B. In some embodiments, the first handle 2A is coupled to the fixed arm 7 with a set of first fasteners 301A-301B. In some embodiments, the second handle 2B is coupled to the movable arm 8 with a set of second fasteners 302A-302B. In some embodiments, the suturing device 1B can use the attachment member 1105A or the attachment member 1105B as described in reference to FIG. 11B and FIG. 11C. For example, the attachment member 1105A can be configured to be attached to the movable jaw 6 that is configured to receive the attachment member 1105A. In another example, the attachment member 1105B can be configured to be attached to the fixed jaw 5 that is configured to receive the attachment member 1105B.

Section B: Suture Loader

Figure 15:
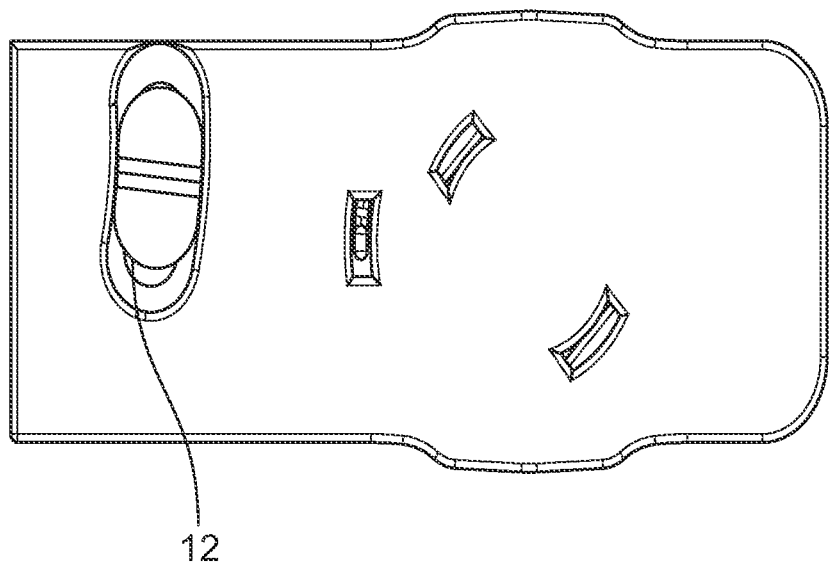
FIG. 15 depicts a back view of an embodiment of the loading apparatus.
Figure 16:
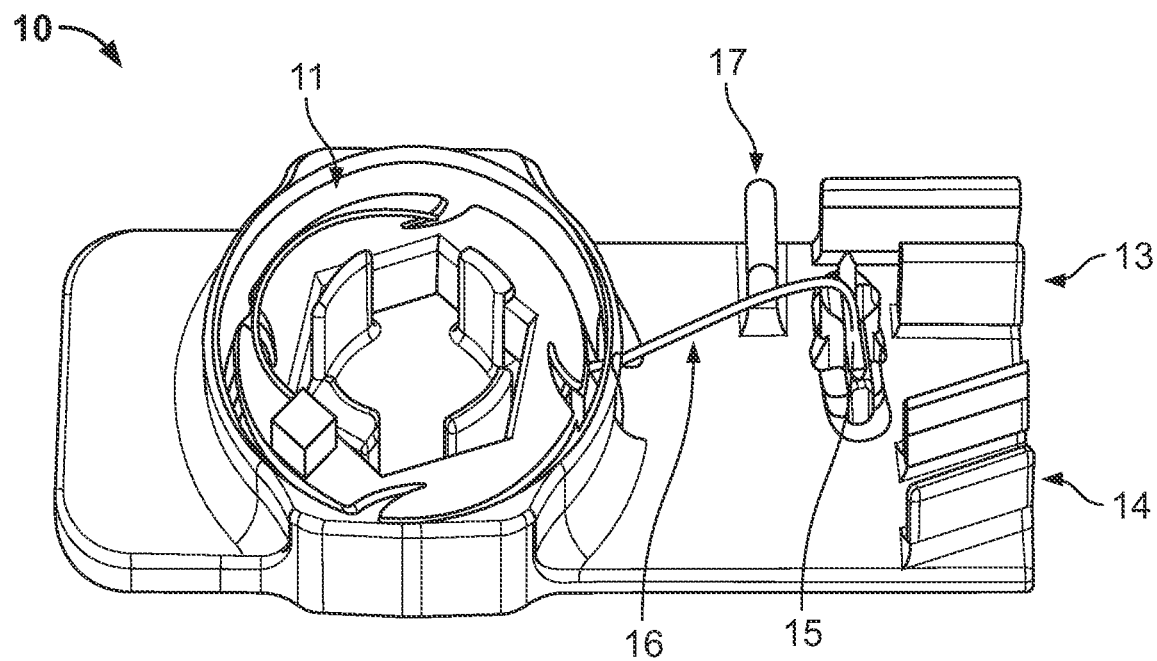
FIG. 16 depicts an embodiment of the loading apparatus with thread.

FIGS. 14A-14C, FIG. 15, and FIG. 16 depict embodiments of the loading apparatus 10 for loading the needle 201 into the suturing device 1A or 1B in a practical and standardized manner. FIG. 15 depicts a back side of an embodiment of the loading apparatus 10. In some embodiments, the loading apparatus 10 includes a first loading slot 13 disposed in the loading apparatus 10. In some embodiments, the first loading slot 13 can receive the fixed jaw 5. For example, the first loading slot 13 can form a channel in the loading apparatus 10. The channel can be sized and angled to receive the fixed jaw 5 such that the fixed jaw 5 can securely fit into the first loading slot 13 to receive the needle 201. The channel be defined by one or more side walls within which the fixed jaw 5 can be positioned. The fixing wall 17 can allow the fixed jaw 5 to maintain its position in the first loading slot 13 of the loading apparatus 10 while receiving the needle 201.

As shown in FIG. 14C, in some embodiments, the loading apparatus 10 includes a slider 12 that includes a slot 15 to hold the needle 201. The slot 15 can be sized and shaped to hold the needle 201. For example, the slot 15 can include a round hole or define a channel sized to receive the needle 201. The needle 201 can be placed into the slot 15 to secure the needle 201 in the slot 15. The slider 12 can move the needle 201 in the slot 15 while the needle 201 stays coupled to the thread 16.

The slider 12 can insert the needle 201 into the first grasping slot 103. In some embodiments, the slider 12 can move within a loading channel 320 to move the slot 15 holding the needle 201 towards the first loading slot 13 and into the first grasping slot 103 of the fixed jaw 5. For example, the loading channel 320 can define a space in which the slider 12 can move. The loading channel 320 and the slider 12 can be sized so that the slider 12 slides within the loading channel 320 but does not fall out of the channel. For example, the slider 12 can be moved to two separate positions for the needle 201 to engage the fixed jaw 5: one to advance the needle 201 into the first grasping slot 103 and another to retract the slider 12 after the needle 201 is secured in the first grasping slot 103.

In some embodiments, the loading apparatus 10 includes the pulley 11 that includes the thread 16 coupled to the needle 201. The thread 16 can be wound or wrapped around the pulley 11. In some embodiments, the pulley 11 can rotate such that the thread 16 moves when the first grasping slot of the fixed jaw 6 exits the first loading slot 13. For example, the pulley 11 can be shaped like a wheel with a grooved rim around which the thread 16 is wound. In some embodiments, the thread 16 can be wound about the pulley 11 for the needle 201 to be loaded back into the loading apparatus 10 after being loaded to the suturing device 1A or the suturing device 1B. For example, this feature may be useful at many instances during a procedure, such as, after passing the first suture, the operator might decide to make a Z-suture with the same needle 201, therefore being able to load it back to the loading apparatus 10 and from there load the needle 201 to the suturing device 1A or the suturing device 1B.

In some embodiments, the loading apparatus 10 includes the second loading slot 14 disposed in the loading apparatus 10. In some embodiments, the second loading slot 14 can receive the movable jaw 6. The second loading slot 14 can form a channel in the loading apparatus 10. The channel can be sized and angled to receive the movable jaw 6 such that the movable jaw 6 can securely fit into the second loading slot 14 while the fixed jaw 6 is in the first loading slot 13. For example, the loading channel 320 be defined by one or more side walls within which the fixed jaw 5 can be positioned. While not shown, in some embodiments, the slider 12 can move within the loading channel 320 to move the slot holding the needle 201 towards the second loading slot 14 and into the second grasping slot 104 of the movable jaw 6. For example, the slider 12 can be moved to two separate positions: one to advance the needle 201 into the second grasping slot 104 and another to retract the slider 12 after the needle 201 is secured in the second grasping slot 104. In another example, the slider 12 can be moved to three separate positions: one to advance the needle 201 into the second grasping slot 104, another to retract the slider 12 after the needle 201 is secured in the second grasping slot 104, and another to advance the needle 201 into the first grasping slot 103. In some embodiments, the pulley 11 can rotate such that the thread 16 moves through the second loading slot 14 when the second grasping slot 104 of the movable jaw 6 exits the second loading slot 14.

Figure 17:
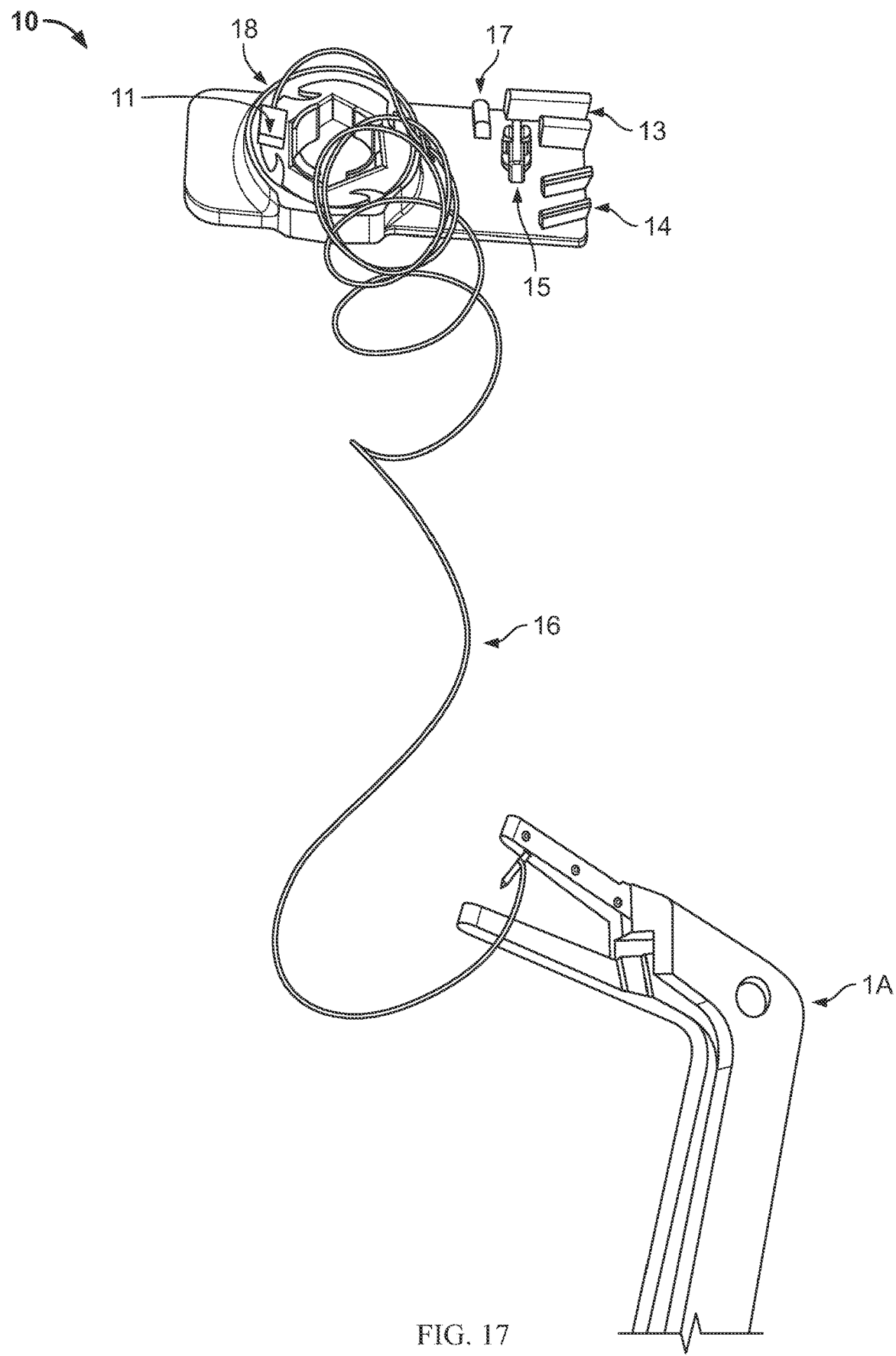
FIG. 17 depicts an embodiment of the suturing device loaded with thread from the loading apparatus.

FIG. 17 depicts an embodiment of the thread 16 with a curved needle 18 to secure the thread 16 into the loading apparatus 10. The thread 16 can be coupled to the needle 201 at one end, and the curved needle 18 can be at the other end of the thread 16. The curved needle 18 can be replaced, if necessary. For example, the thread 16 can be tied or untied from the curved needle 18. The curved needle 18 can have a sharp end to hook, attach, or wrap around the pulley 11 to secure the curved needle 18. The curved needle 18 can be mounted onto the pulley 11 such that the curved needle 18 enables the pulley 11 to wind the thread 16. The pulley 11 allows the thread 16 to be unwound in a controlled manner after the suturing device 1 is removed from the loading apparatus 10 to prevent the thread 16 from being loose and forming knots or clumps.

Section C: Method

Figure 18:
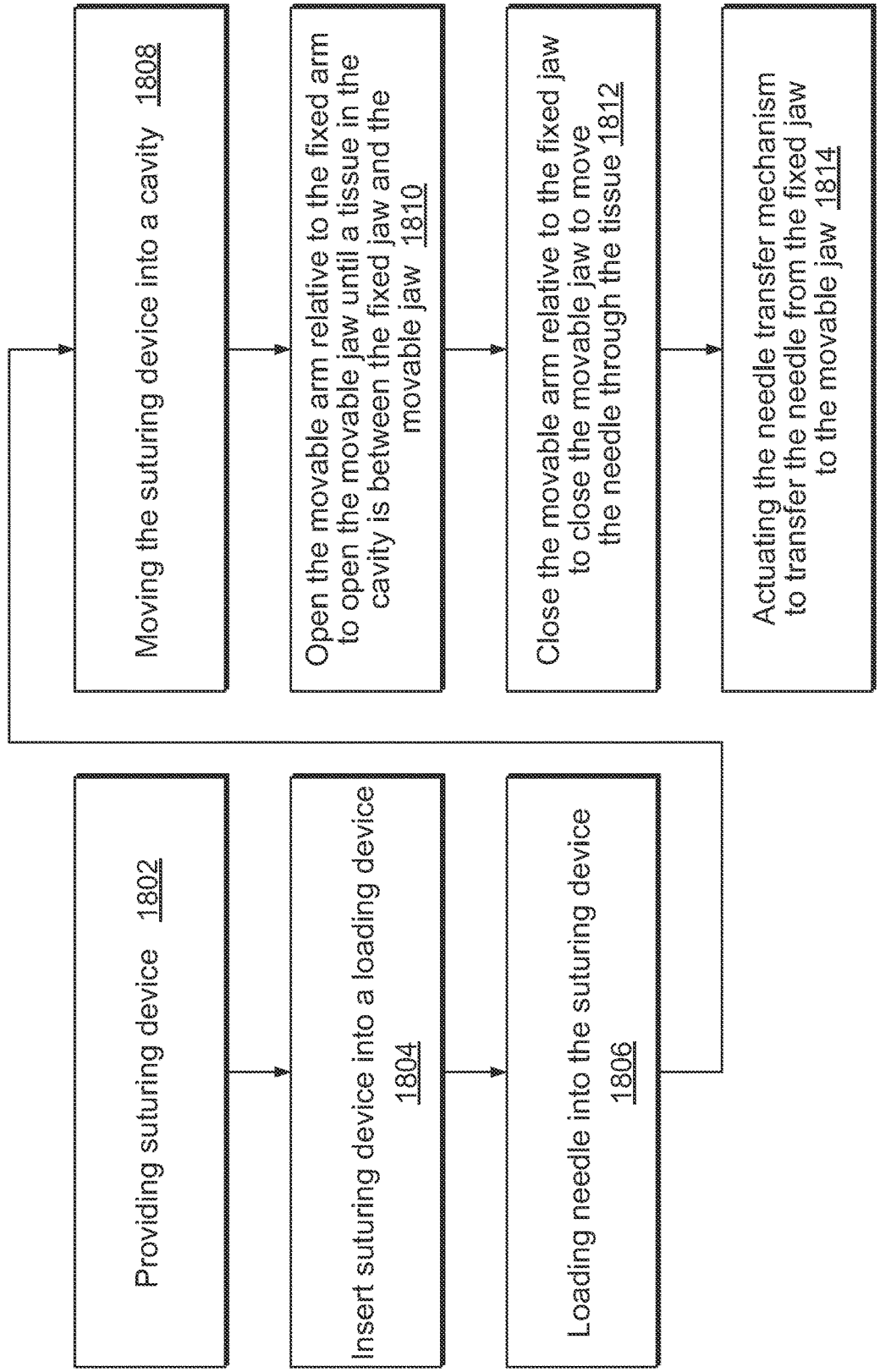
FIG. 18 depicts a flow chart of a method for using the suturing device and the loading apparatus.

FIG. 18 depicts a flow chart of a method 1800 for using the suturing device 1A and the loading apparatus 10 for suturing. The method 1800 can include providing the suturing device 1A or suturing device 1B (STEP 1802). It is contemplated that method 1800 can be performed with any other embodiment of the suturing devices. The shape of the suturing device and the angle between the jaws and arms can be optimal for certain procedures or ligaments. For example, the angles can be optimized for safety to prevent hurting other tissues such as bladder. The operator can select the suturing device 1A or the suturing device 1B based on the treatment site to be sutured. For example, the operator can select among suturing devices based on the ligament to be sutured.

Figure 19:
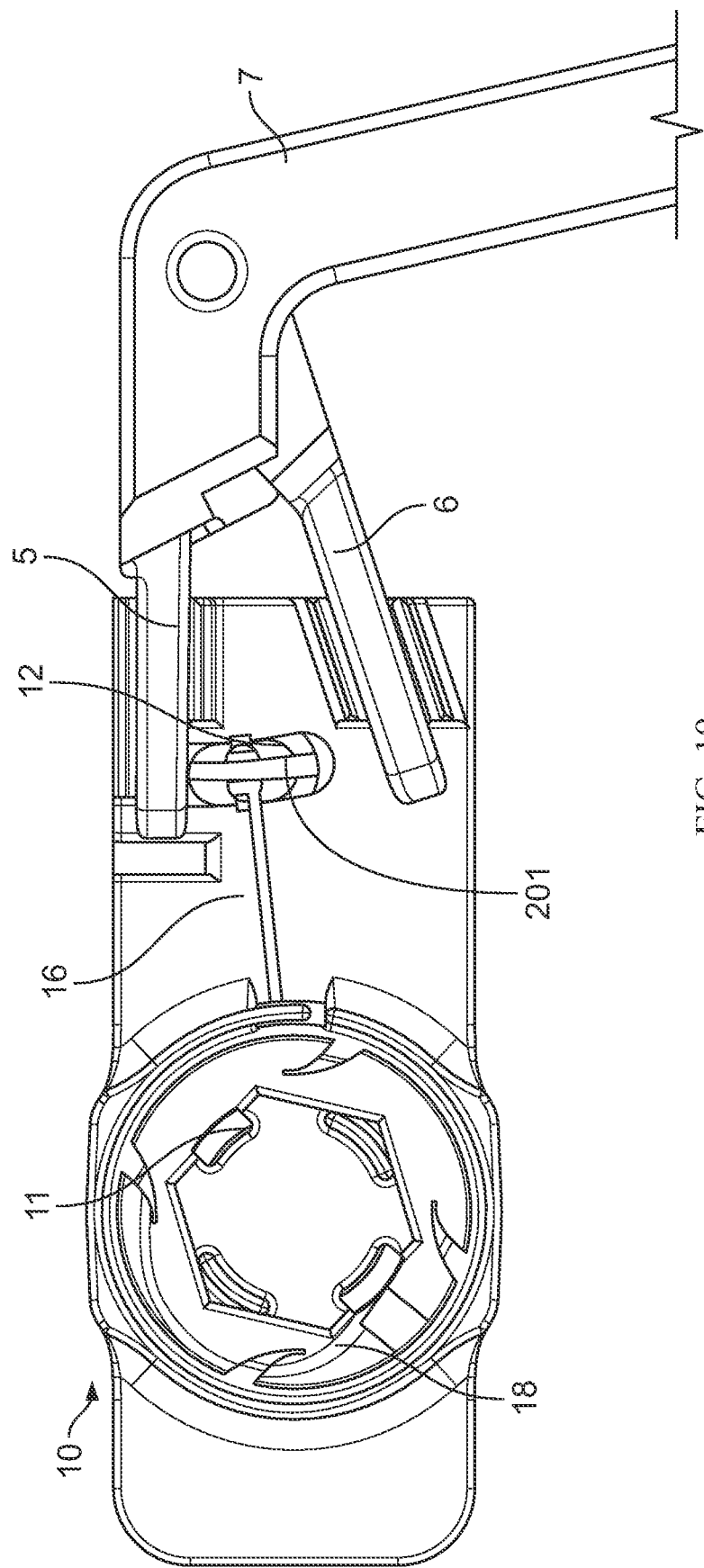
FIG. 19 depicts an embodiment of the suturing device loaded onto the loading apparatus.

The method 1800 can include inserting the suturing device 1A or 1B into the loading device 10 (STEP 1804). The lever 3 can be pulled towards the handle 2 to be in second position 110B to receive the needle 201 in the fixed jaw 5. Before placing the suturing device 1A into the loading apparatus 10, the stopper 605 can be moved to the deactivated position to be able to be move the lever 3 to second position 110B from the first position 110A or the third position 110C. As shown in FIG. 19, the movable jaw 6 of the suturing device 1A can be opened relative to the fixed jaw 5. The suturing device 1A can be placed on the suture loading apparatus 10 in such a way that the fixed jaw 5 fits into the first loading slot 13 and the movable jaw 6 fits into the second loading slot 14.

Figure 20A:
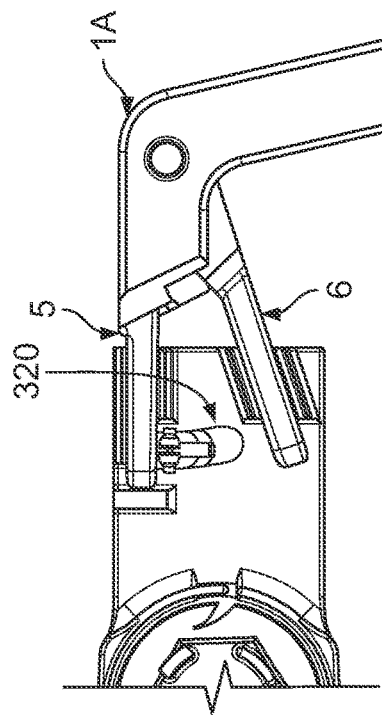
Figure 20B:
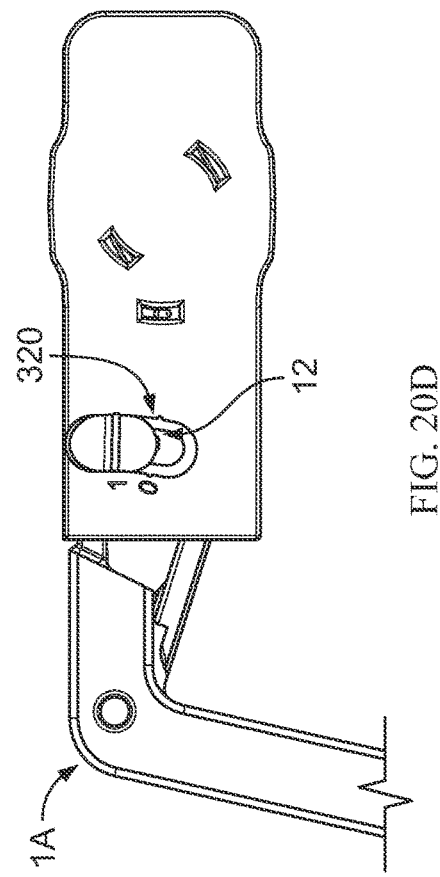
Figure 20C:
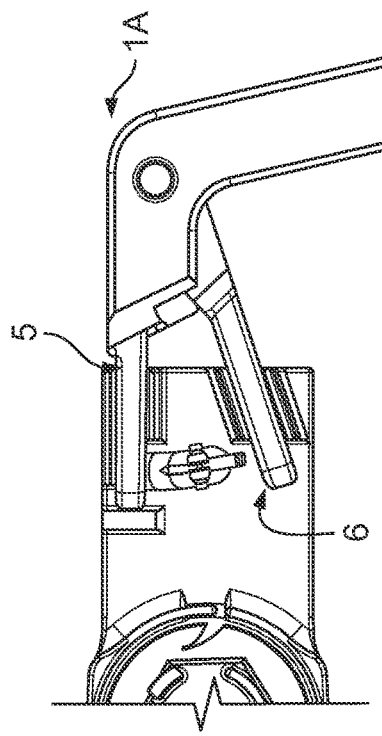
Figure 20D:
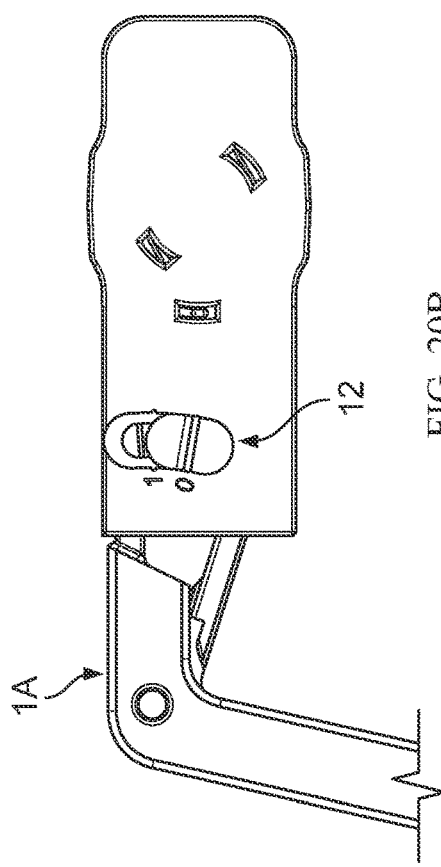

The method 1800 can include loading the needle 201 into the suturing device 1A (STEP 1806). FIG. 20A is a front view and FIG. 20B is a rear view of the slider 12 in an initial (e.g., default) position when the needle 201 is loaded into the slider 12. FIG. 20C is a front view and FIG. 20D is a rear view of the slider 12 moved along the loading channel 320 to move the needle 201 into the fixed jaw 5. The needle slider 12 can be moved in the direction of the fixed jaw 5. The slider 12 can be driven in the loading channel 320 to load the needle 201 into the fixed jaw 5. The needle 201 can be loaded into the first grasping slot 103.

As shown in FIGS. 20A-20I, in some embodiments, the slider 12 includes safety notches 121A-122B in the loading channel 320 and protrusions 123A-123B on the slider 12 for making a click effect to inform the operator that the needle 201 is loaded successfully. The safety notches 121A-122B and protrusions 123A-123B can provide a click effect informing the operator that the needle 201 is loaded successfully based on the notches 121A and 121B or unloaded successfully based on the notches 122A and 122B. FIG. 20E and FIG. 20F show closer views of the slider 12 showed in FIG. 20B and FIG. 20D, respectively. FIG. 20G, FIG. 20H, and FIG. 20I show details of the slider 12 from a different view. FIG. 20I shows front views of slider 12 according to the FIG. 20E. FIG. 20G shows a back view of the slider according to the FIG. 20E. FIG. 20H shows perspective view of the slider 12 according to the FIG. 20E.

Figure 21:
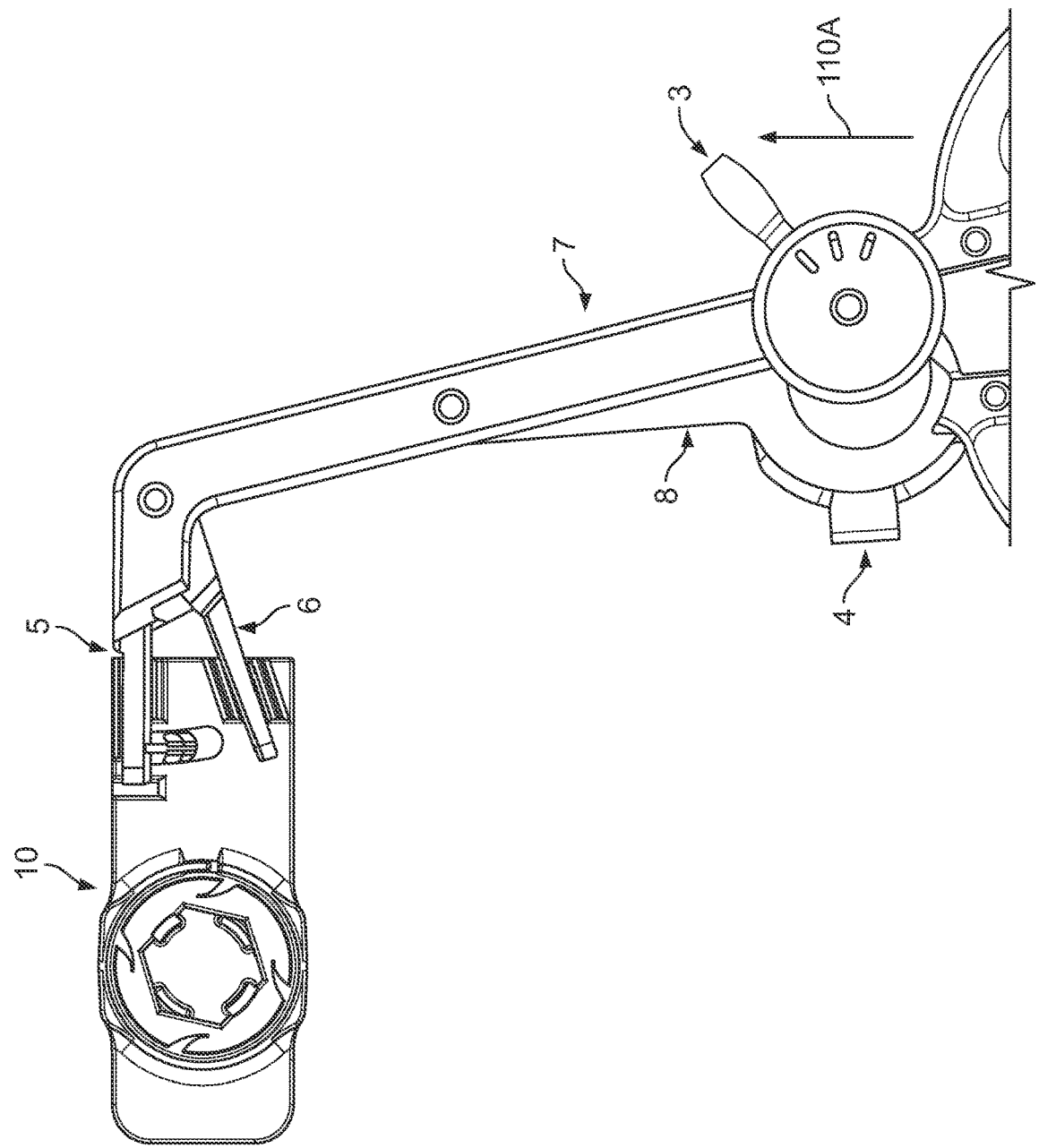
FIG. 21 depicts the suturing device securing the needle loaded by the loading apparatus.

FIG. 21 shows the needle 201 from the loading apparatus 10 being secured in the first grasping slot 103 of the fixed jaw 5. After the slider 12 loads the needle 201 into the first grasping slot 103, the lever 3 can be moved to the first position 110A to grasp the needle 201 in the first grasping slot 103 of the fixed jaw 5. As shown in FIG. 21, the lever 3 can be pulled upwards and into the first position 110A. For example, the lever 3 can be moved to the first position 110A from the second position 110B. The stopper 605 can be in the deactivated position to be able to be move the lever 3 to the second position 110B from the first position 110A or the third position 110C. After securing the needle 201 in the first grasping slot of the fixed jaw 5, the slider 12 can be moved away from the fixed jaw 5 while the needle 201 is secured in the first grasping slot of the fixed jaw 5.

After receiving the needle 201, the suturing device 1A can be separated from the loading apparatus 10 and the needle 201 pulls on the thread 16 that is wound on the pulley 11. The suture thread 16 can be pulled from the pulley 11 and thus from the loading apparatus 10. One end of the thread 16 can remain attached to the curved needle 18 that remains attached to the pulley 11.

In some embodiments, instead of STEP 1804 and STEP 1806, the attachment member 1105A or the attachment member 1105B that has a needle 201 already preloaded can be attached to the suturing device 1A or the suturing device 1B. The attachment can be attached to the fixed jaw 5 or the movable jaw 6 as shown in FIG. 11B and FIG. 1C. For example, instead of having to load the needle 201 with the loading apparatus 10, the operator can attach the attachment to the suturing device 1A or the suturing device 1B for suturing with the attachment. At the conclusion of the suturing operation, the attachment can be removed with the needle 201, and another attachment with a replacement needle 201 can be attached to the fixed jaw 5 or the movable jaw 6.

Figure 22A:
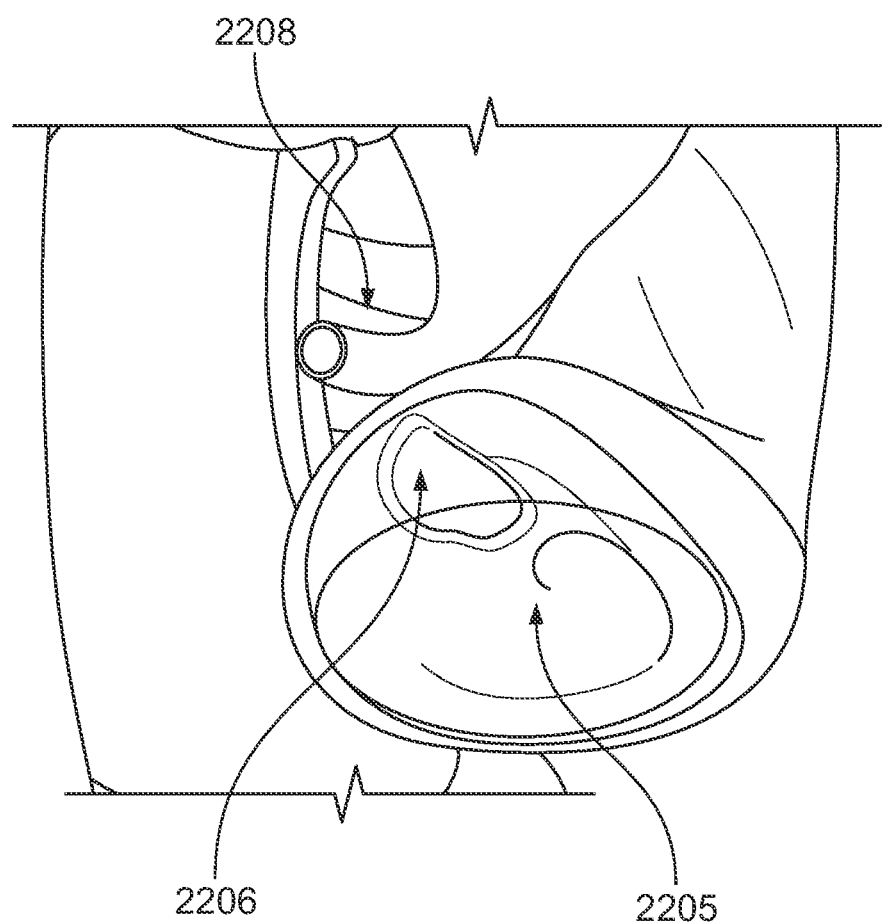
FIG. 22A, FIG. 22B, FIG. 22C, FIG. 22D, FIG. 22E, FIG. 22F, and FIG. 22G depict the suturing device maneuvering in the cavity.
Figure 22B:
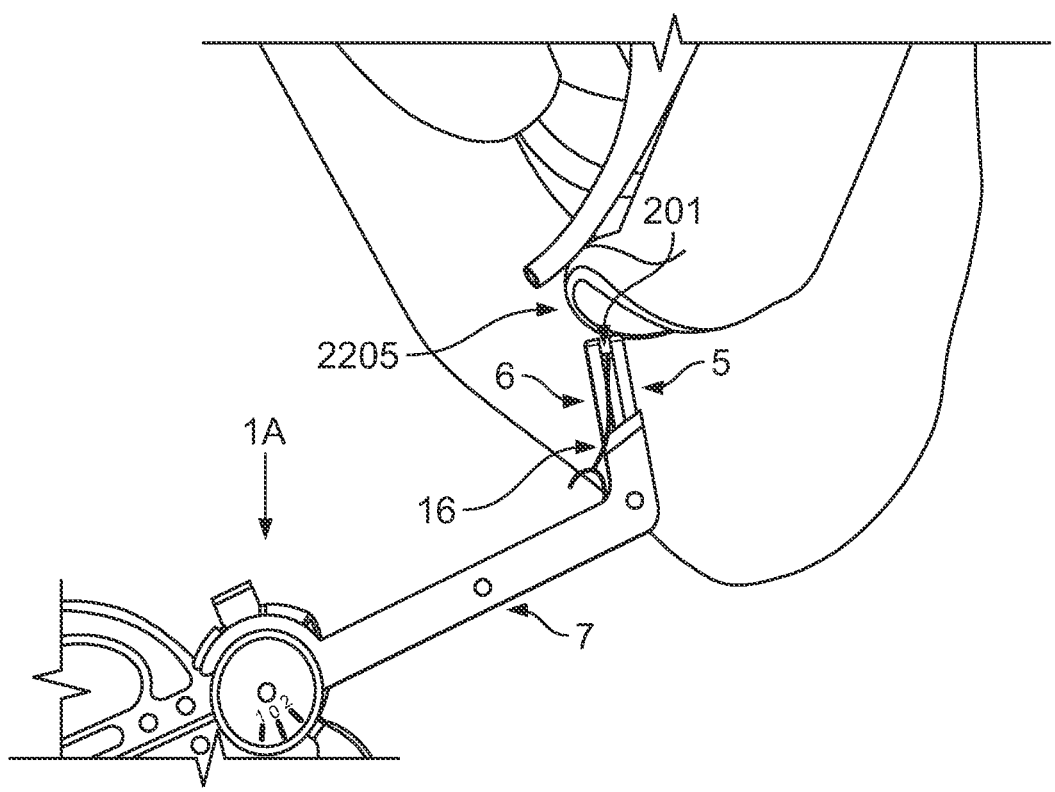
Figure 22C:
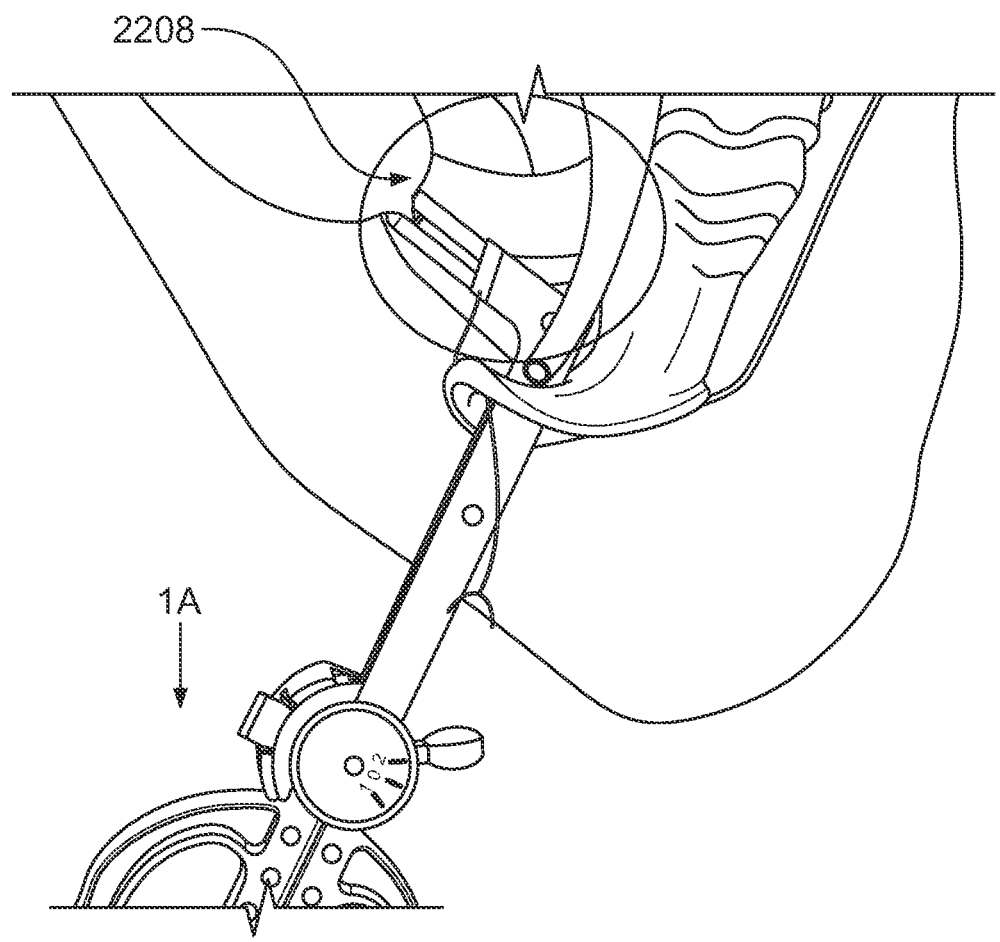

The method 1800 can include moving the suturing device 1A into a vaginal cavity (STEP 1808). As shown in FIG. 22A, the suturing device 1A can be inserted into the vaginal cavity 2205. The operator can cut an incision 2206 (e.g., 3 cm incision) in the wall of the vagina to insert the suturing device 1A through the incision 2206 to reach the pelvic cavity 2208 (e.g., Retzius Space) where the suturing operation is to be performed (e.g., the ATFP is in this cavity) and the sutures are delivered to the pelvic cavity. As shown in FIG. 22B, the suturing device 1A can be inserted into the vaginal cavity 2205. As shown in FIG. 22C, the suturing device 1A can be inserted into the pelvic cavity 2208 through the vaginal cavity 2205 such that no incision in the abdomen is opened to insert the suturing device 1A. The operator can move the suturing device 1A into the vaginal cavity 2205 while the movable jaw 6 is closed relative to the fixed jaw 5.

Figure 22D:
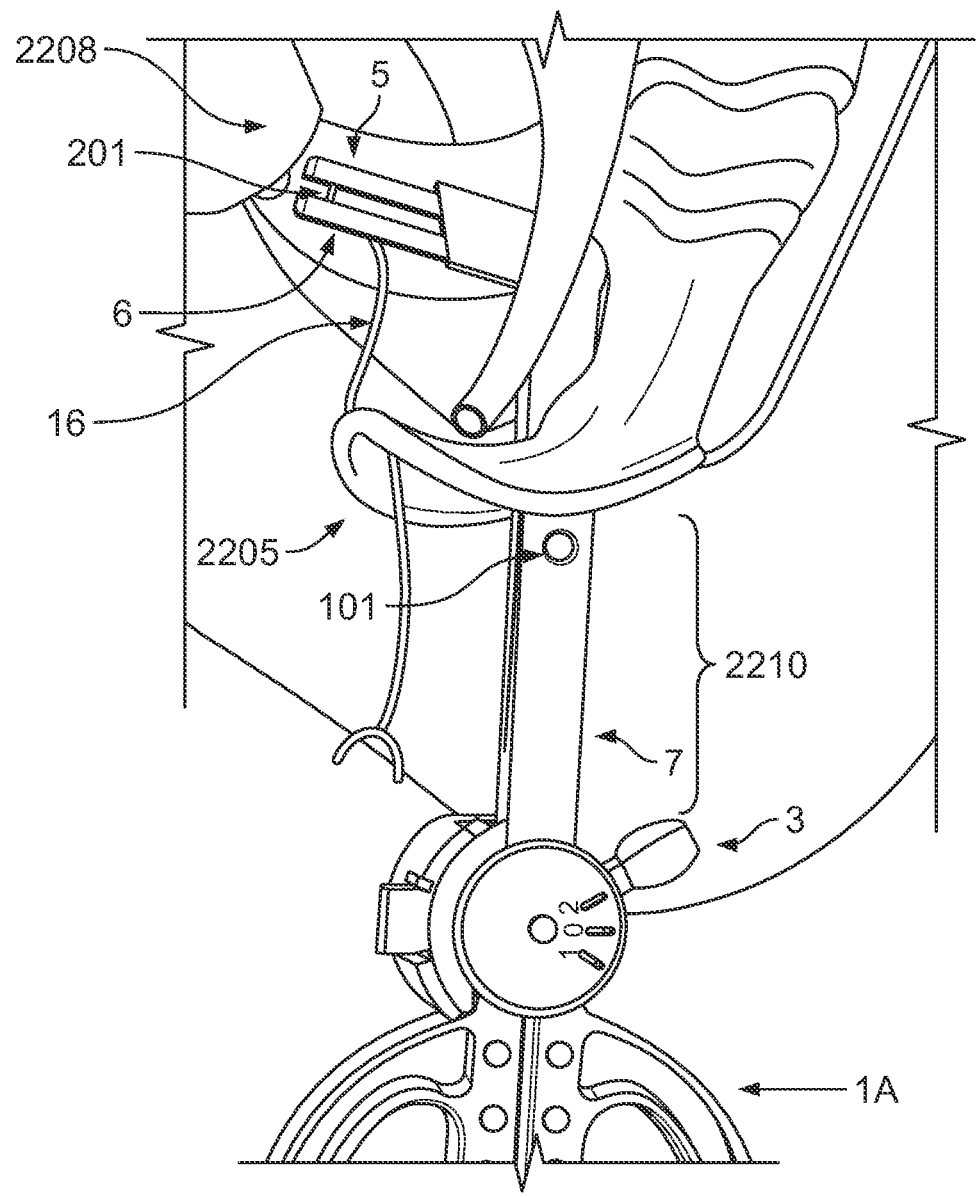
Figure 22D:
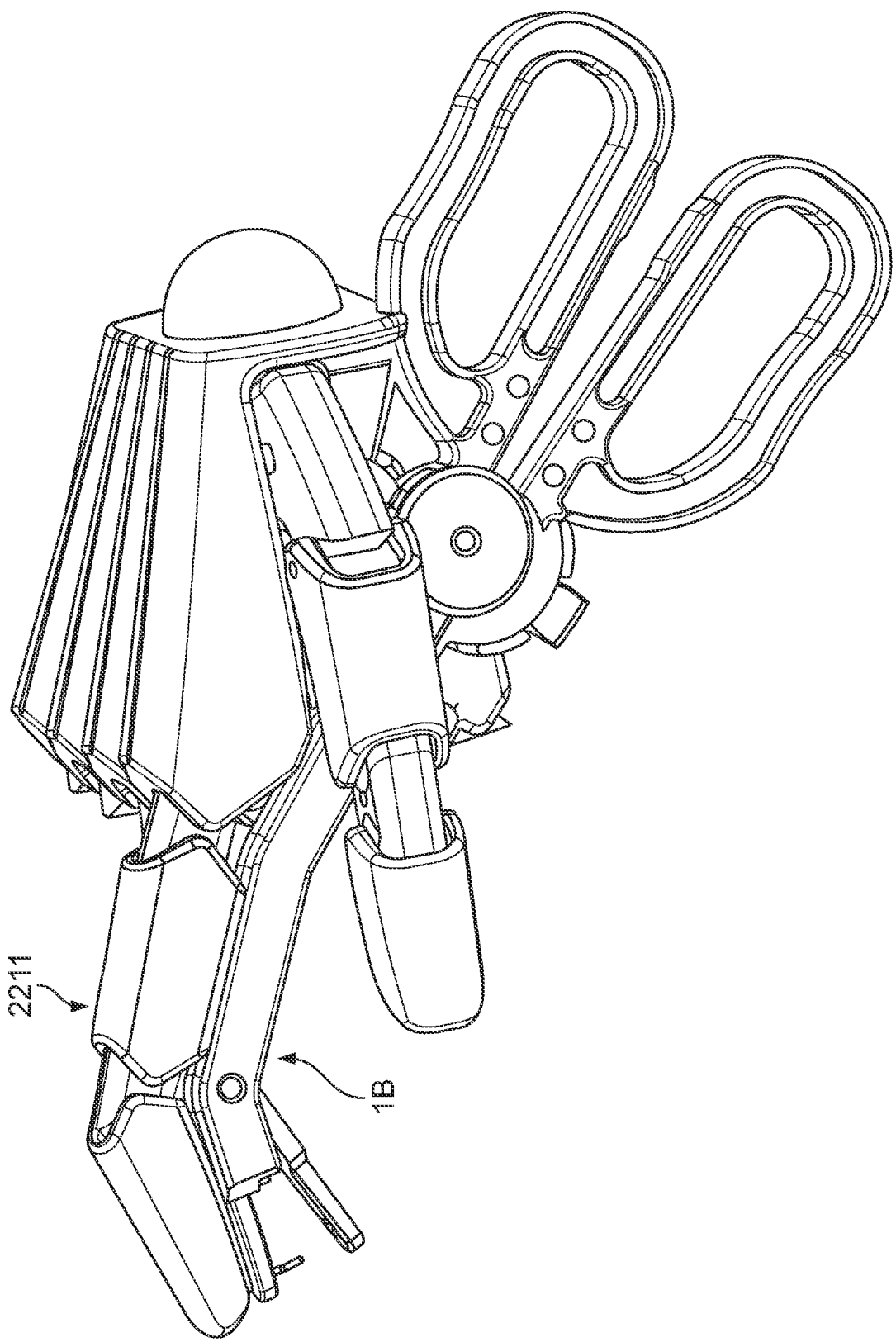

As shown in FIG. 22D, the operator can move the suturing device 1A until the fixed jaw 5 or the movable jaw 6 touches a target tissue inside the pelvic cavity 2208, which allows the operator to safely position the suturing device 1A. For example, the operator can determine the place of target tissue (e.g., ATFP for SUI operations) by palpating the target tissue and then the operator can move the suturing device 1A until the fixed jaw 5 or the movable jaw 6 touches the palpated ligament in a closed position. Once the fixed jaw 5 or the movable jaw 6 touches the palpated tissue, the operator can infer that the suturing device 1A is properly positioned. For example, the suturing device 1A can be inserted into the pelvic cavity 2208, which can be the operation site, through the incision 2206 opened at the wall of vagina.

The suturing device 1A can be designed based on the length of the cavity into which the suturing device 1A is expected to be inserted. The area of points on the suturing device 1A that remains outside the cavity when the operator stops inserting the suturing device 1A can be known as a stop area 2210. For example, the stop area 2210 can be near the arm joint 101. In another example, during operation of the suturing device 1A, the arm joint 101 can be positioned outside the vaginal cavity 2205 while a portion of the suturing device 1A can be positioned inside the vaginal cavity 2205. In another example, the stop area 2210 is closer to the handle 2A and the handle 2B such that the suturing device 1A is inserted further into the vaginal cavity 2205.

As shown in FIG. 22DD, in some embodiments, the shape of the suturing device 1B can be advantageous for palpating during suturing operations. During POP operations, the operator can use their index finger 2211 to locate the ligament where the suture will be placed and determine the safe area on the ligament where to place the suture. The operator can take the suturing device 1B to this safe area and pass the suture. In some embodiments, the shape of suturing device 1B can match the shape of the index finger 2211 during palpation and the size of the suturing device 1B can conform to be moved together with the index finger 2211 of the operator during palpation. The shape and size of the suturing device 1B and the fixed jaw 5 being fixed enable the operator to place the suturing device 1B under their index finger 2211 and in one step, do the palpation and pass the suture. The suturing device 1B, with its size, shape, and fixed jaw 5, can conform to the shape of the index finger 2211 and work together in harmony with the index finger 2211 of the operator.

Figure 22E:
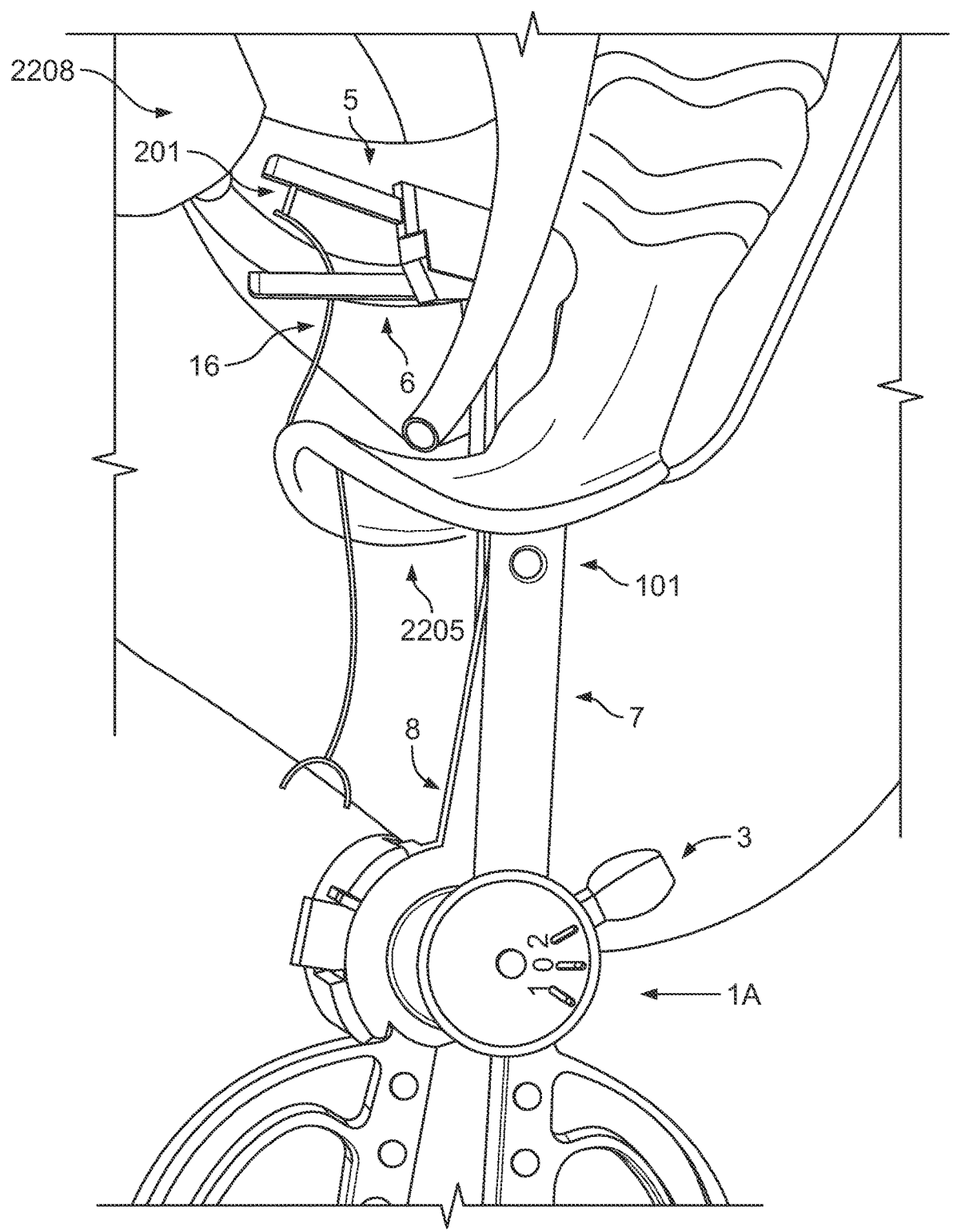

Referring back to FIG. 18, the method 1800 can include opening the movable arm 8 relative to the fixed arm 7 to open the movable jaw 6 until the tissue in the pelvic cavity 2208 is between the fixed jaw 5 and the movable jaw 6 (STEP 1810). As shown in FIG. 22E, the operator can pull the suturing device 1A away from the tissue to create a safe distance to open the movable jaw 6 relative to the fixed jaw 5. After opening the movable jaw 6, the operator can position the fixed jaw 5 on the tissue to be sutured.

The widening of the suturing device 1A caused by the opening of the handle 2A and the handle 2B can remain outside of the vaginal cavity 2205. The movement of the movable arm 8 in the vaginal cavity 2205 can cause the movable jaw 6 to pivot about the jaw joint 100 inside the pelvic cavity 2208. Since the movable arm 8 can cause the movable jaw 6 to move while the fixed jaw 5 and the fixed arm 7 can stay in the same position, the operator can predict where the needle 201 would be suturing, which allows the operator to more safely suture tissue that is difficult to see or not visible at all.

Figure 22F:
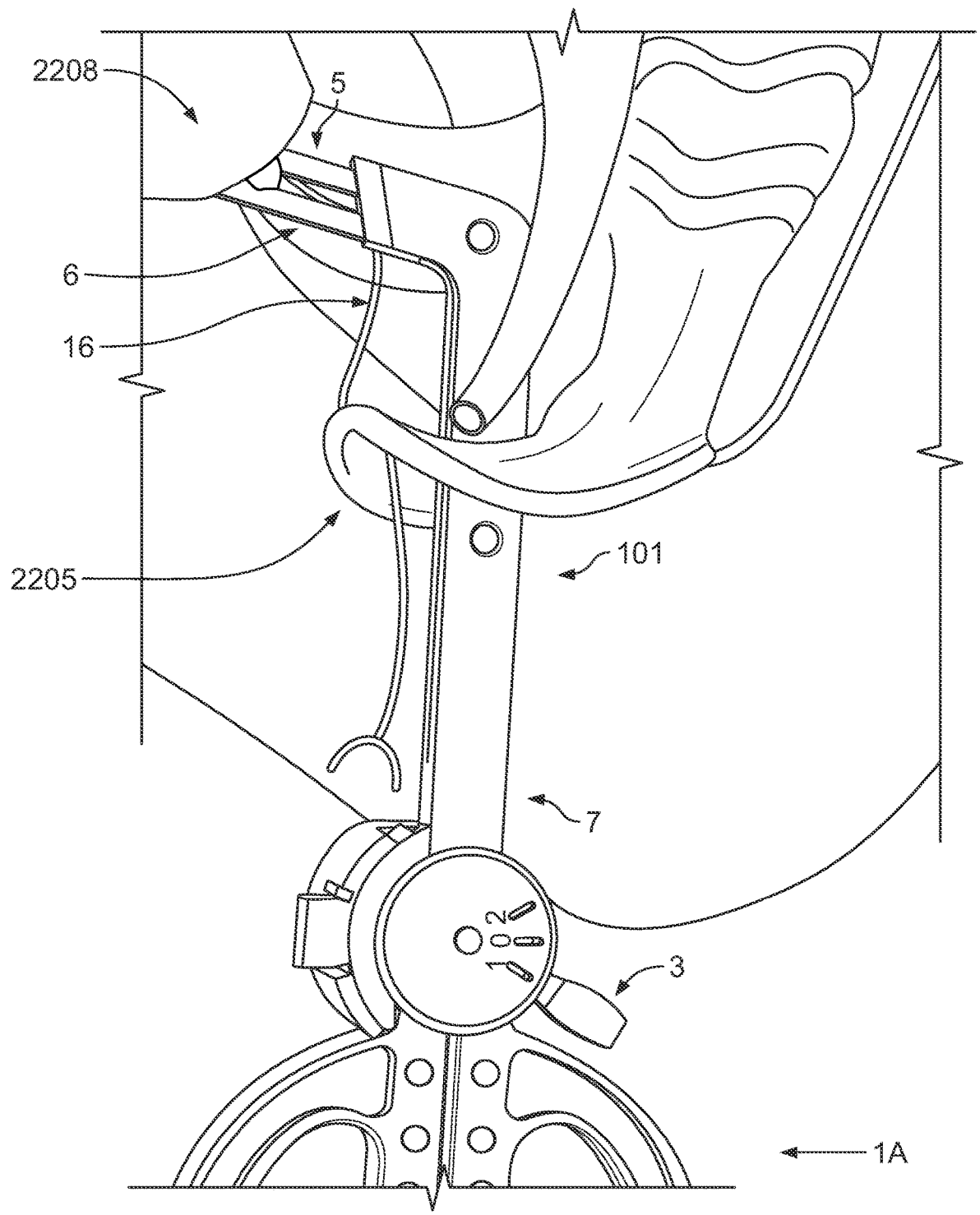

The method 1800 can include closing the movable arm 8 relative to the fixed arm 7 to close the movable jaw 6 to move the needle 201 through the tissue (STEP 1812). As shown in FIG. 22E and FIG. 22F, while the movable jaw 6 moves, the fixed jaw 5 can provide a fixed reference, and the tissue inside the pelvic cavity 2208 to be sutured can be placed between the fixed jaw 5 and the movable jaw 6. By moving the movable jaw 6 relative to the fixed jaw 5, the needle 201 is passed through the tissue. While the location where the suturing is required might be in a narrow, deep, and area that is difficult to see or not visible at all for the operator, the needle 201 can suture in the desired location because the movement of the movable jaw 6 is predictable and precise while the fixed jaw 5 remains stationary with respect to the target tissue. As shown in FIG. 22F, the operator can close the movable arm 8 relative to the fixed arm 7 to close the movable jaw 6 relative to the fixed jaw 5.

The method 1800 can include actuating the needle transfer mechanism 4 to transfer the needle 201 from the fixed jaw 5 to the movable jaw 6 to pass the suture (STEP 1814). The operator can move the lever 3 to transfer the needle 201 from the fixed jaw 5 to the movable jaw 6. By pulling the lever 3 in the direction of the handle 2 and into the third position 110C, the needle 201 is transferred and secured in the movable jaw 6. The needle 201 can be transferred from the first grasping slot 103 of the fixed jaw 5 to the second grasping slot 104 of the movable jaw 6. Having the fixed jaw 5 stay in a fixed location while transferring the needle 201 can enable safe transfer of the needle 201 when the tissue is difficult to see or not visible at all.

Figure 22G:
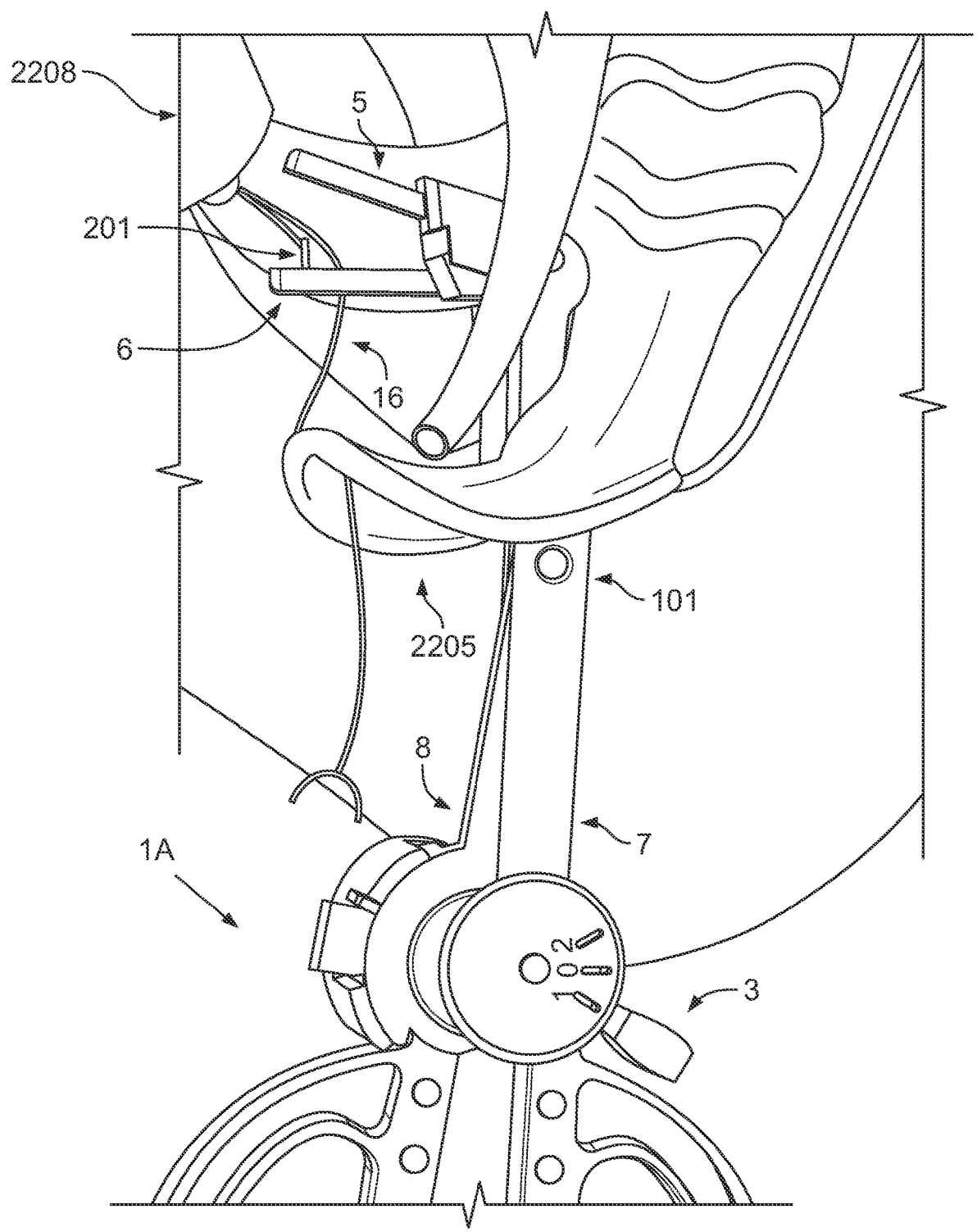

As shown in FIG. 22G, the needle 201 has been transferred to the movable jaw 6. The movable jaw 6 can move away with the needle 201 and open relative to the fixed jaw 5 to position for another suture. As shown in FIG. 22A-22G, the needle 201 was first loaded into the fixed jaw 5 so the needle 201 was transferred from the fixed jaw 5 to the movable jaw 6. However, it is contemplated that the needle 201 can be first loaded into the movable jaw 6 (e.g., second grasping slot 104). The movable jaw 6 and the needle 201 can pierce through the tissue and move towards the fixed jaw 5 until the needle 201 is disposed in the fixed jaw 5 (e.g., first grasping slot 103).

Since the suturing devices described herein can transfer the needle 201 between the jaws, the operator can reach the treatment site and suture with the same device instead of relying on one device to maneuver the treatment site and another device to suture. Moreover, the transfer of the needle 201 between the jaws enables sequential suturing. For example, if the procedure requires so, the operator can also make suture after suture (sequential) with the same needle 201, which is called Z-suture or 8-figure suture.

After making the suture, the suturing device 1A can be removed from the pelvic cavity 2208. The stopper 605 can be moved into the deactivated position, and the lever 3 can be moved into the second position 110B to release the needle 201 from both the fixed jaw 5 and the movable jaw 6. Since the needle 201 is attached to the thread 16, which itself is attached to the curved needle 18, the operator can release the needle 201 to remove the suturing device 1A but keep the thread 16 sutured in the pelvic cavity 2208.

For example, for a stress urinary incontinence operations, the operator can load the device four times to pass four sutures with the needle 201. Two of these sutures can be made on the left ATFP and two sutures can be made on the right ATFP. For example, there are 2 ATFPs in the pelvis that are symmetrically situated; one on the left side and the other on the right side of the pelvis. These sutures can be made by inserting the suturing device into the pelvic cavity 2208 via the incision 2206 in the vaginal cavity 2205, and by turning the jaws of the device to the right and to the left respectively. It is contemplated that the operation can be performed with 2 stitches or a different number of sequential stitches depending on the operation, the suturing devices, and the preferences of the operator. For example, an operation with suturing device 1B may use only 1 suture or 2 sutures at the same side.

After each suture is completed, the operator can move the suturing device 1A out of the pelvic cavity 2208. The operator can release, from the suturing device 1A, the used needle 201 with the thread 16 attached to the curved needle 18 such that the thread 16 remains sutured in the pelvic cavity 2208. The operator can re-load the suturing device 1A with another needle until four such sutures are passed. After making the four sutures, the four threads 16 and their respective curved needles 18 remain attached and sticking out of the pelvic cavity 2208.

After completing 4 sutures with needle 201, the operator can pass or pull the 4 sutures by pulling the curved needle 18 attached to each thread 16. These sutures can be placed on the vaginal wall to form a loop with the sutures passed on ATFP with needle 201. For example, the operator can pull the end of each suture towards one another, which has the effect of bringing the wall of the vagina closer to the ATFP at each side (e.g., Left and Right) as well as lifting the vaginal wall, the bladder and urethra, thus restoring their anatomical position. The operator can tie each loop (e.g., 4 in total) with knots and cut off the extra thread 16 and thus the needle 201 and the curved needle 18.

In some embodiments, the operator can make the loop without the curved needle 18 attached to the other end of the thread 16. For example, the operator can pass the suture from the vaginal tissue in the vaginal cavity 2205 by pulling on the needle 201 to pull the thread 16 and tie the loop with the thread 16.

The operator can use a standard suture to close the incision 2206 that was opened to place the suturing device 1A into the cavity. For example, the operator can use with standard sutures and standard suturing devices such as a needle holder and thumb forceps. In another example, the operator can use a needle holder and thumb forceps to perform suture patterns.

In some embodiments, the suturing device 1A and the suturing device 1B can be used for native tissue repair without a synthetic implant (e.g., by using a sling or mesh or instead of mid-urethral sling operations for SUI, mesh operations for POP). For example, the suturing devices can also be used to assist the placement of an "adjustable single incision sling" in the pelvic cavity 2208 (e.g., mini sling that can tighten and loosen as needed to treat stress urinary incontinence). Each end of the mini sling can include a needle 201, and the needle 201 can be loaded into a specialized loading apparatus to form a kit for placing the mini sling. The suturing devices can use the specialized loading apparatus to load each needle and suture each needle at different ends of the pelvic cavity 2208 to place the mini sling 2300 along the pelvic cavity 2208.

Figures 23A, 23B:
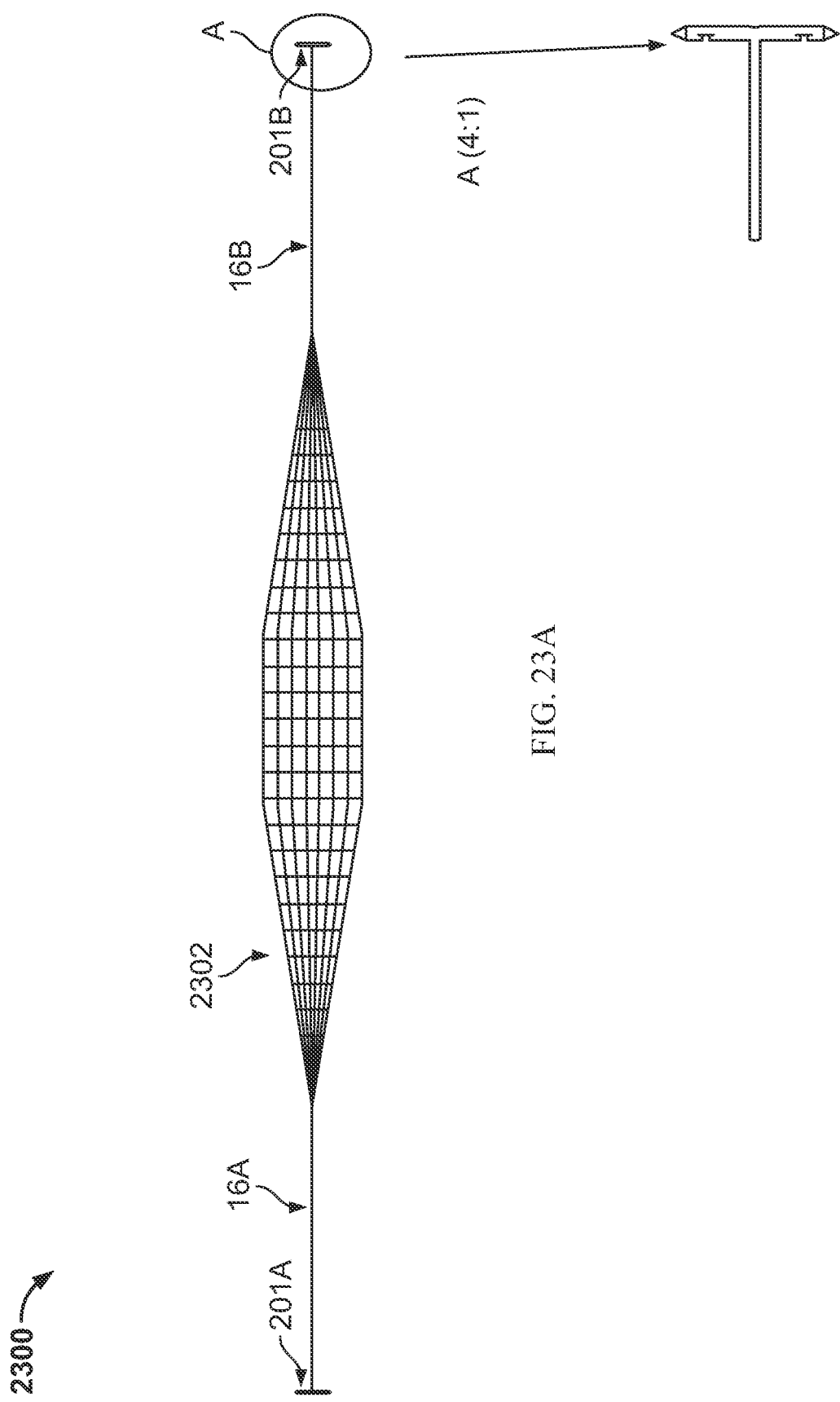
FIG. 23A and FIG. 23B depicts an embodiment of a mini sling.

FIG. 23A depicts an embodiment of a mini sling 2300. The mini sling 2300 can be an adjustable, tension-free single incision mid-urethral sling. The mini sling 2300 can have a rectangular shape that tapers to the edges to allow an a-traumatic placement. The suturing device can be for the placement of an adjustable, tension-free "single incision mid-urethral sling (mini sling)" in addition to the placement of suture that was described in this patent. The tension of the mini sling 2300 can be adjustable. The mini sling 2300 can be tension-free by not having to be fixated to the tissue by anchors. This can be advantageous over slings that only allow the operator to adjust the tension of the sling during the operation, which means that once the tension is adjusted, the mini sling is fixated in the tissue with anchors.

The mini sling 2300 can include a mesh 2302 narrowing from the middle towards the edges. For example, the mesh 2302 (e.g., the rectangular part) can be 6 cm long. One edge is attached to a thread 16A that itself is attached to a needle 201A, and another edge is attached to a thread 16B that itself is attached to a needle 201B. FIG. 23B depicts a close up view of the needle 201B. The operator can use the needle 201A and the needle 201B to load the mini sling 2300 into the suturing device 1A or the suturing device 1B to deliver the mini sling 2300 into the pelvic cavity 2208 for placement. Since the needle 201A and the needle 201B are disposed at opposite ends, the needles 201A and 201B can enable each end of the mini sling 2300 to be loaded into the suturing device 1A or 1B, after which the suturing device 1A or 1B can move the mini sling 2300 to the target location for placement of the mini sling 2300 in the pelvic cavity 2208.

Figure 24:
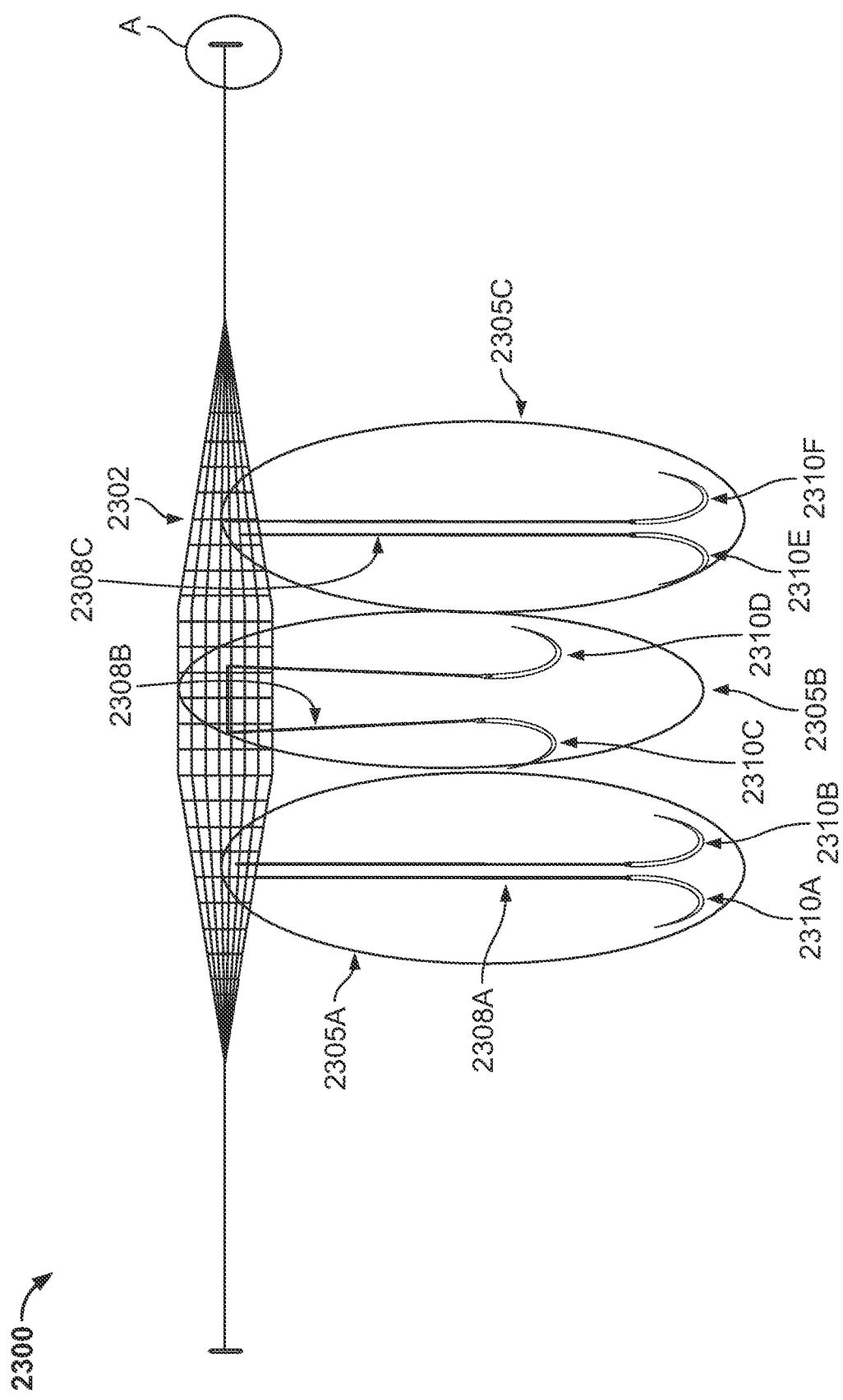
FIG. 24 depicts a close up view of an embodiment of a mini sling including adjustment sutures.

FIG. 24 depicts a close up view of an embodiment of the mini sling 2300 including adjustment sutures 2305A-2305C. For example, the mini sling 2300 can include 3 adjustment sutures 2305A-2305C. While not shown, the mini sling 2300 can include fewer or additional adjustment sutures. Each of the adjustment sutures 2305A-2305C can include threads 2308A-2308C. Each of the threads 2308A-2308C can be attached to the mesh 2302 by the operator after placing the mesh 2302 in the pelvic cavity 2208. Each of the adjustment sutures 2305A-2305C can include curved needles 2310A-2310F attached to each end of the threads 2308A-2308C such that the curved needles 2310A-2310F extend from the mesh 2302 and outside of the pelvic cavity 2208 after the adjustment sutures 2305A-2305C are attached to the mesh 2302 by the operator. The curved needles 2310A-2310F can be pulled on outside of the pelvic cavity 2208 to enable adjustment of the tension of the mesh 2302 of the mini sling 2300.

The adjustment suture 2305B can be disposed in the middle of the mesh 2302 for loosening the mesh 2302. The adjustment suture 2305A and the adjustment suture 2305B can be disposed towards ends of the mesh 2302 (e.g., points where the mesh 2302 was cut at each end) for tightening the mesh 2302. The curved needles 2310A-2310F can be brought into the vaginal cavity 2205 by piercing through the vaginal wall 2207 and cut off. The remaining threads 2308A-2308C can be knotted and stored in a housing to be later used for adjustment.

Figure 25:
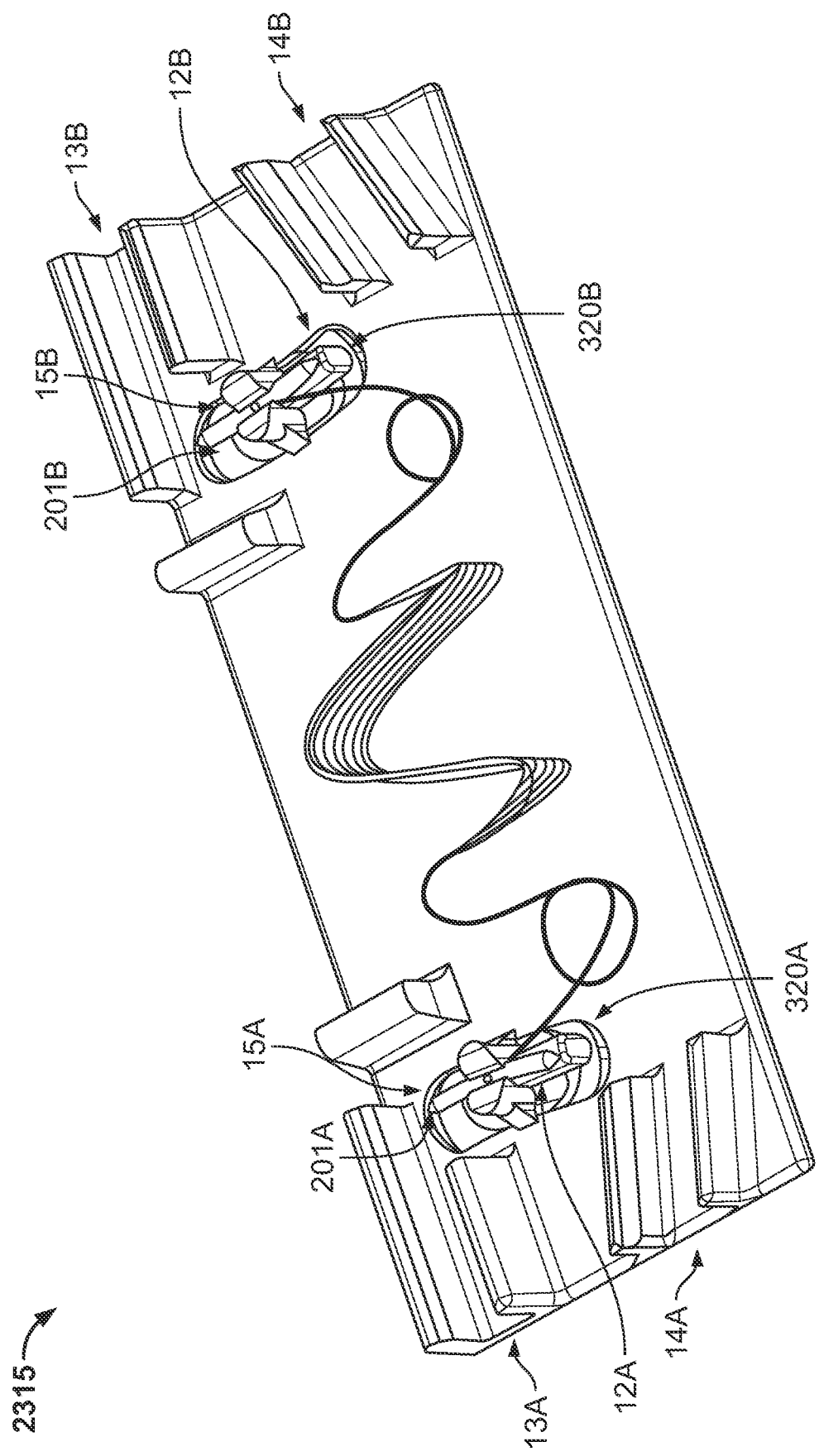
FIG. 25 depicts an embodiment of the sling loader for the mini sling.

FIG. 25 depicts an embodiment of the sling loader 2315 for the mini sling 2300. The sling loader 2315 can be similar to and include the functionality of the loading apparatus 10, but the sling loader 2315 can be specially designed for the mini sling 2300. In some embodiments, the mini sling 2300 can be pre-loaded into the sling loader 2315. For example, the mini sling 2300 and the sling loader 2315 can be a kit. The sling loader 2315 can include a first loading slot 13A and 13B configured to receive the fixed jaw 5. The sling loader 2315 can include a second loading slot 14A and 14B configured to receive the movable jaw 6.

The sling loader 2315 can receive both the needle 201A and needle 201B of the mini sling 2300 to load the mini sling 2300 into the suturing device 1A. The sling loader 2315 can include a slider 12A disposed in a slot 15A that can hold the needle 201A of the mini sling 2300. The sling loader 2315 can include a slider 12B disposed in a slot 15B that can hold the needle 201B of the mini sling 2300.

FIG. 26 and FIGS. 27A-27J depict an embodiment of using the mini sling 2300 to treat urinary incontinence. For example, the mini sling 2300 can be positioned such that the mesh 2302 is positioned under the urethra 2705 to treat urinary incontinence. The mini sling 2300 can be positioned by using the suturing device 1A to pass the needle 201A and the needle 201B through the target tissue in the pelvic cavity 2208 (where ATFP adheres to the pubic bone) as described herein in mesh repair. The thread 16A and the thread 16B of the mini sling 2300 can be passed through the incision 2206 (e.g., vaginal wall) in the vaginal cavity 2205. The thread 16A and thread 16B on the ends of the mini sling 2300 can be pulled simultaneously to position the mesh 2302 of the mini sling 2300. In some embodiments, it is contemplated that suturing device 1B can be used to position the mini sling 2300.

Figure 26:
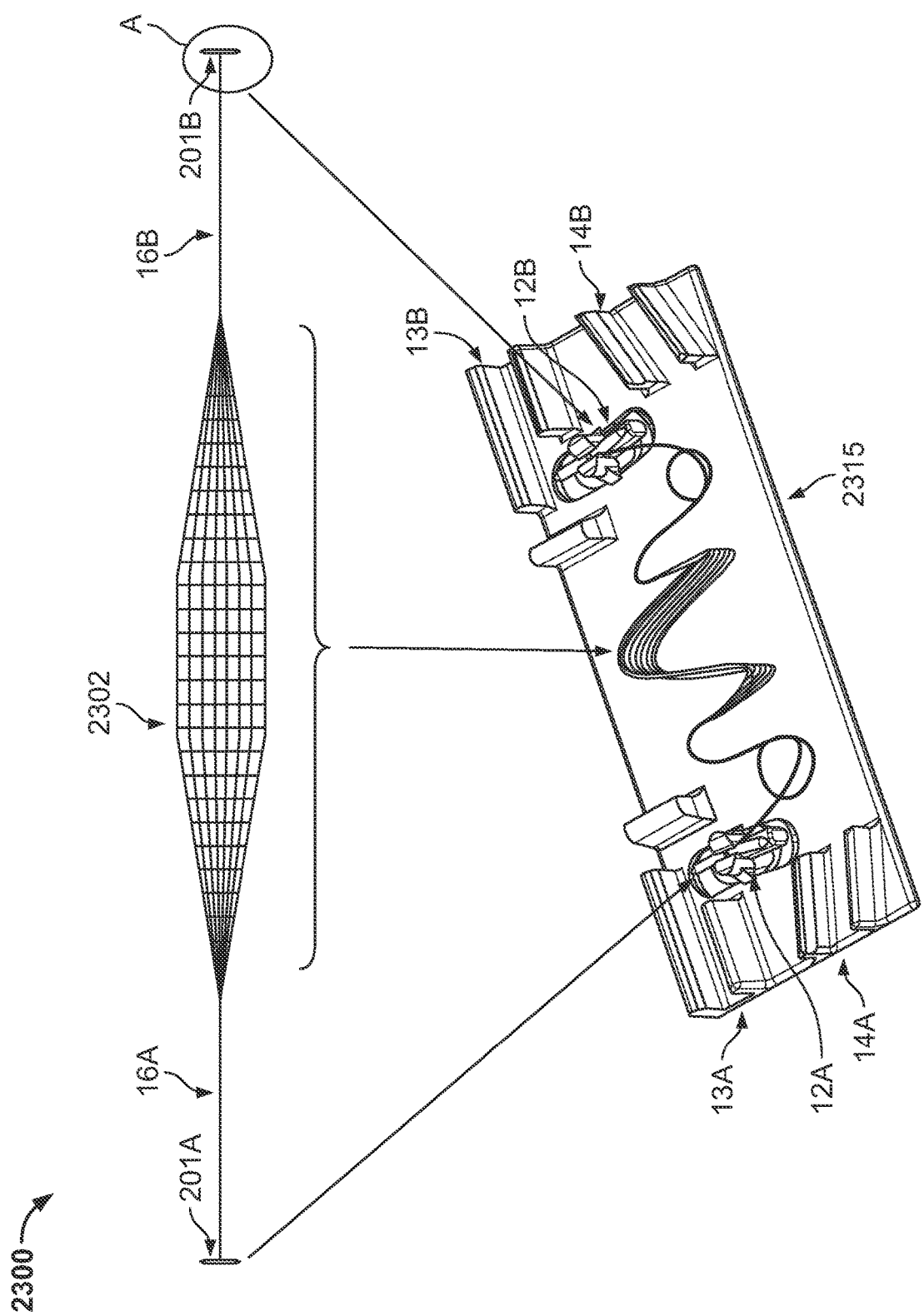
FIG. 26 depicts an embodiment of the mini sling placed on the sling loader.
Figure 27A:
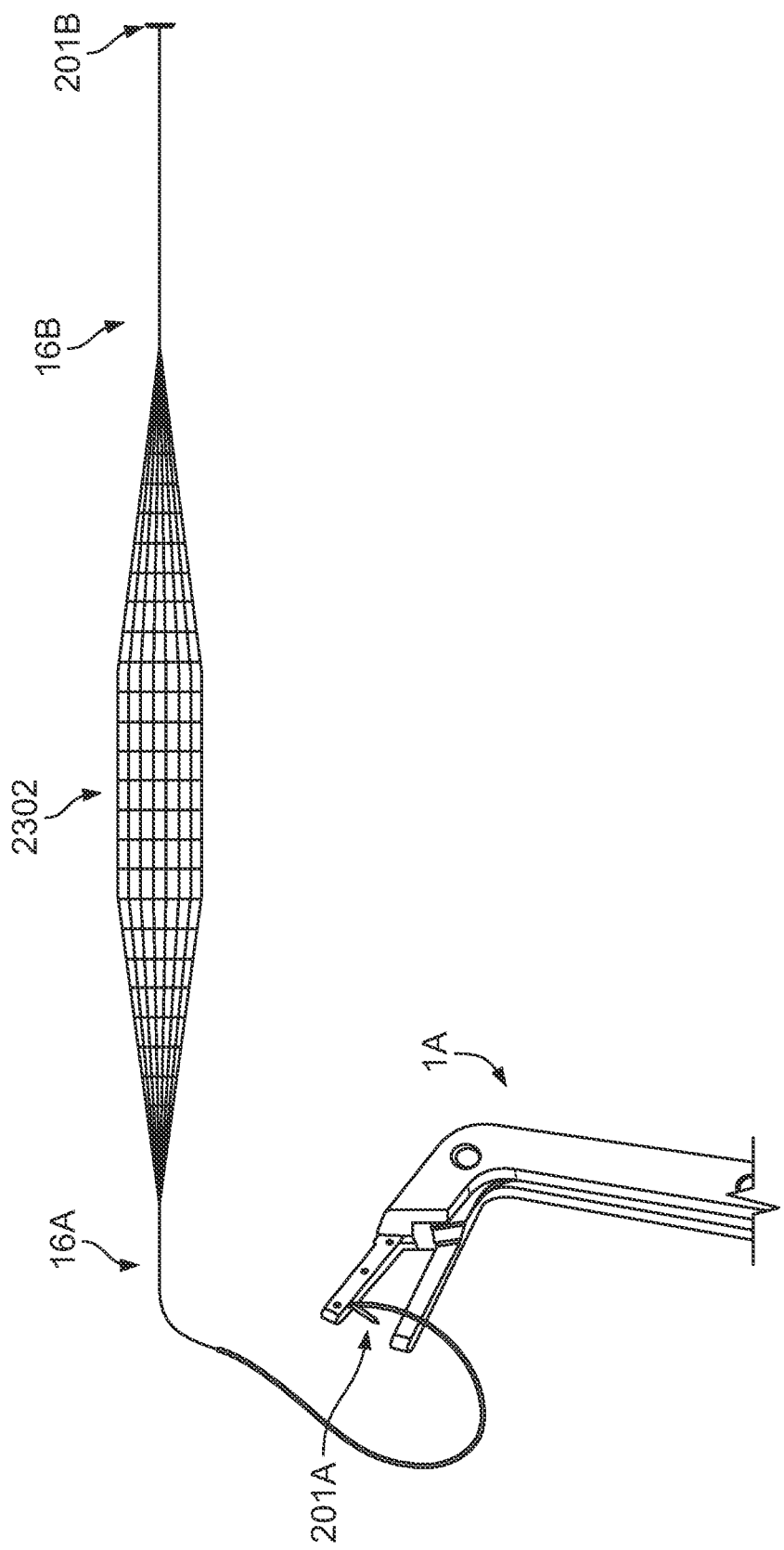

As shown in FIG. 26, the mini sling 2300 can be loaded into the sling loader 2315. In some embodiments, the slider 12A and slider 12B are symmetrically positioned to symmetrically load the needle 201A and needle 201B of the mini sling 2300. The mini sling 2300 can be loaded at the ends by the needle 201A and needle 201B into the suturing device 1A or the suturing device 1B via the sling loader 2315. As shown in FIG. 27A, the needle 201A has been loaded into the suturing device 1A by the sling loader 2315.

Figure 27B:
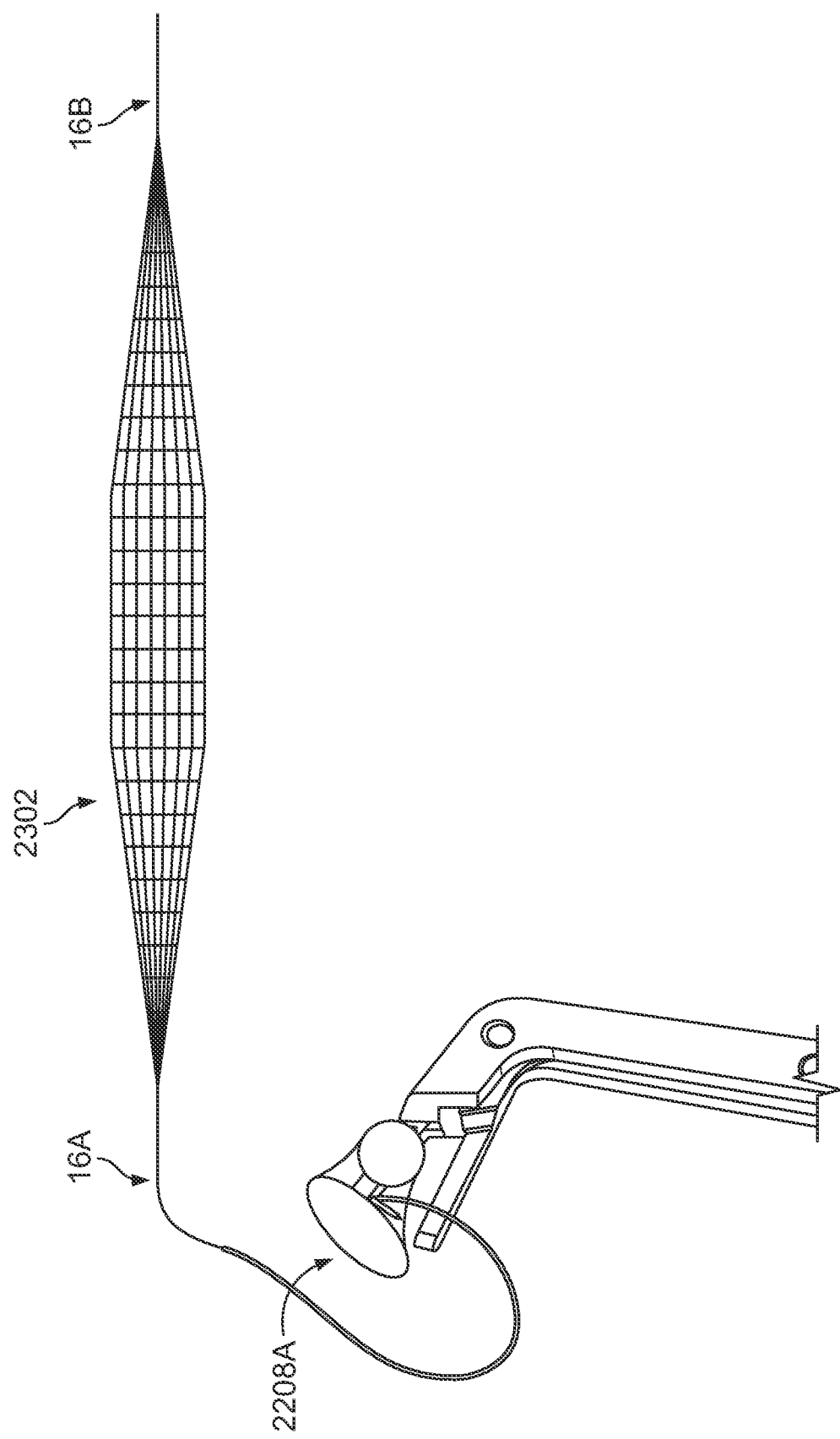

As shown in FIG. 27B and as described in FIGS. 22A-22G, the suturing device 1A can be used to pass the needle 201A through the target tissue in the pelvic cavity 2208A to place one end of the mini sling 2300. The needle 201A can be inserted into the vaginal cavity 2205 and through the incision 2206 to reach the pelvic cavity 2208A. For example, a sharp and blunt dissection (e.g., 3 cm incision) is advanced from under the vesicovaginal fascia towards the junction of the pubic ramus and symphysis pubis, and the arcus tendinous fascia pelvis is detected. The thread 16A follows the needle 201A through the incision 2206, and the mesh 2302 follows the thread 16A into the pelvic cavity 2208A such that the mesh 2302 can be positioned in the pelvic cavity 2208.

As shown in FIG. 27C and as described in FIGS. 22A-22G, the suturing device 1A can be used to pass the needle 201B through the target tissue in the pelvic cavity 2208B to place the other end of the mini sling 2300. For example, the suturing device 1A can release the needle 201A, and then the needle 201B can be loaded into the suturing device 1A by the sling loader 2315. The mini sling 2300 can thus be positioned relative to the urethra 2705 by using the suturing device 1A to pass the needle 201A through the pelvic cavity 2208A, and the needle 201B through the pelvic cavity 2208B. The thread 16A and the thread 16B of the mini sling 2300 can be passed through the incision 2206 (e.g., vaginal wall) in the vaginal cavity 2205.

The device 1A can position thread 16A and thread 16B to position the mini sling 2300 to where it should be placed in the pelvic cavity 2208A and 2208B, respectively. The device 1A can pass the needle 201 through the tissue at the target place, but no stitching is done, such that the thread 16A is not tied in a knot 2720A but only passes through the tissue to pass the end of the mini sling 2300 through the tissue. For example, the ends (e.g., 16A and 16B) of the mini sling 2300 are not secured by stitching because the mini sling 2300 is placed tension-free.

Figure 27D:
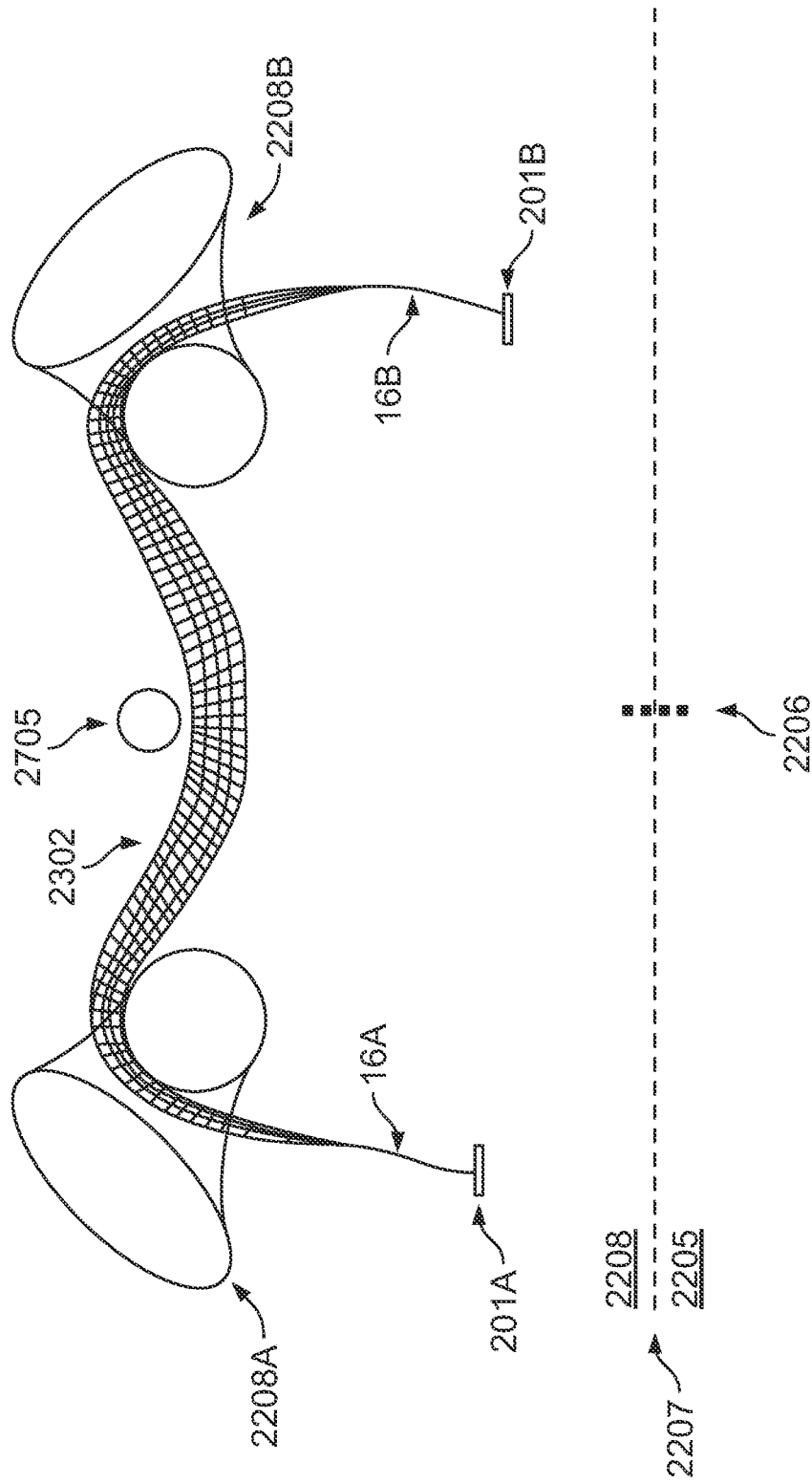

As shown in FIG. 27D, the thread 16A and thread 16B on the ends of the mini sling 2300 can be pulled simultaneously to position the mesh 2302 relative to the urethra 2705. For example, after delivering the mini sling 2300, the mesh 2302 can be elevated up towards the urethra 2705 as both ends of the mini sling 2300 can be pulled by the thread 16A and thread 16B. For example, both the thread 16A and the thread 16B can be pulled simultaneously. The mesh 2302 of the mini sling 2300 can rise under and towards the urethra 2705 when the thread 16A and the thread 16B are pulled.

Figure 27E:
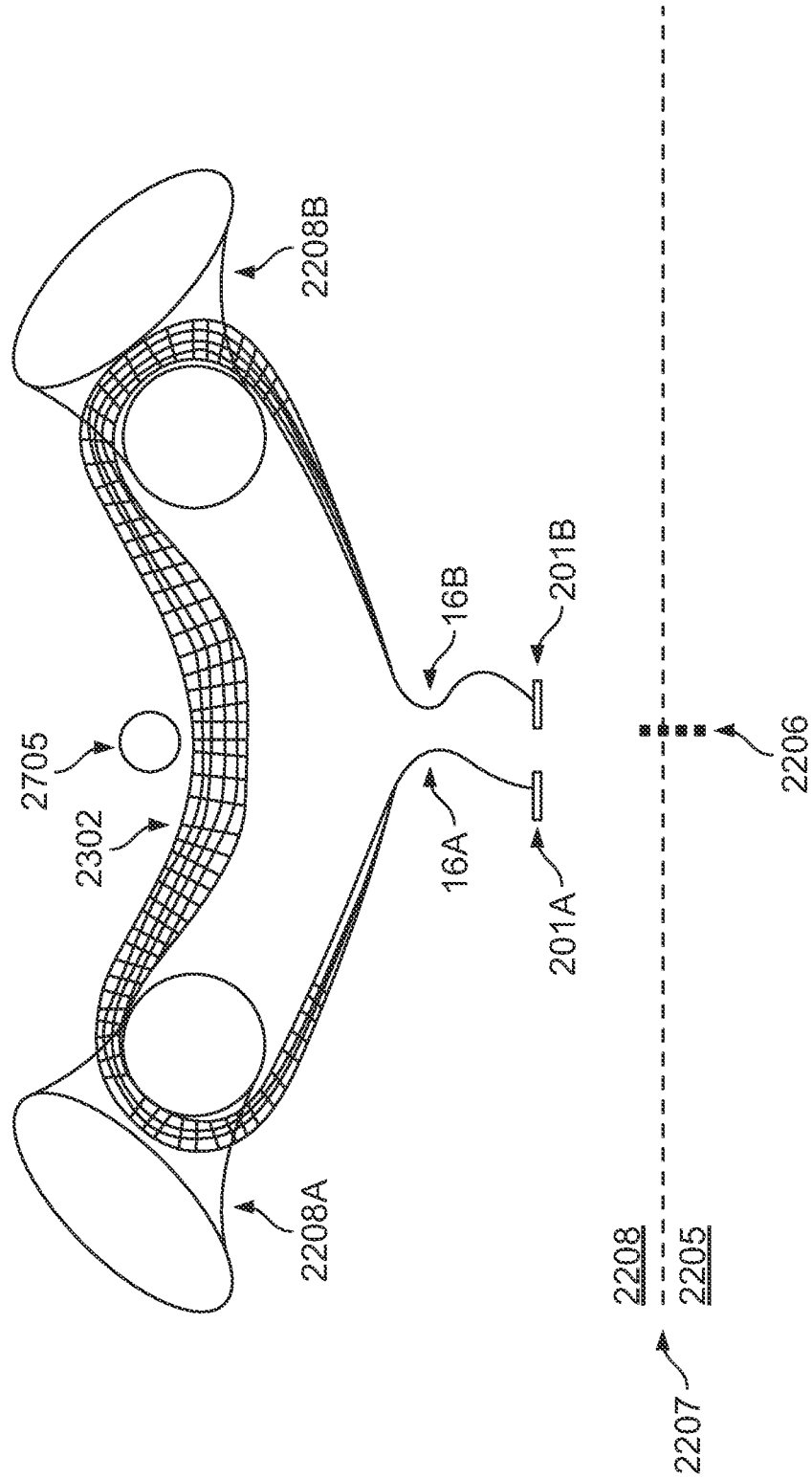

As shown in FIG. 27E, the thread 16A and thread 16B can be pulled such that the mesh 2302 can be placed tension free into the pelvic cavity 2208 instead of fixating in the tissue with anchors. The thread 16A and thread 16B can be pulled until the thread 16A and the thread 16B attached to the mesh 2302 are visible to the operator through the incision 2206. For example, the thread 16A and the thread 16B can be pulled out of the incision towards the vaginal cavity 2205 for the surgeon to be able to cut them as well as the extra portion of the mesh 2302 at its ends and make sure that only the targeted length of mesh 2302 stays in the pelvic cavity 2208.

Figure 27F:
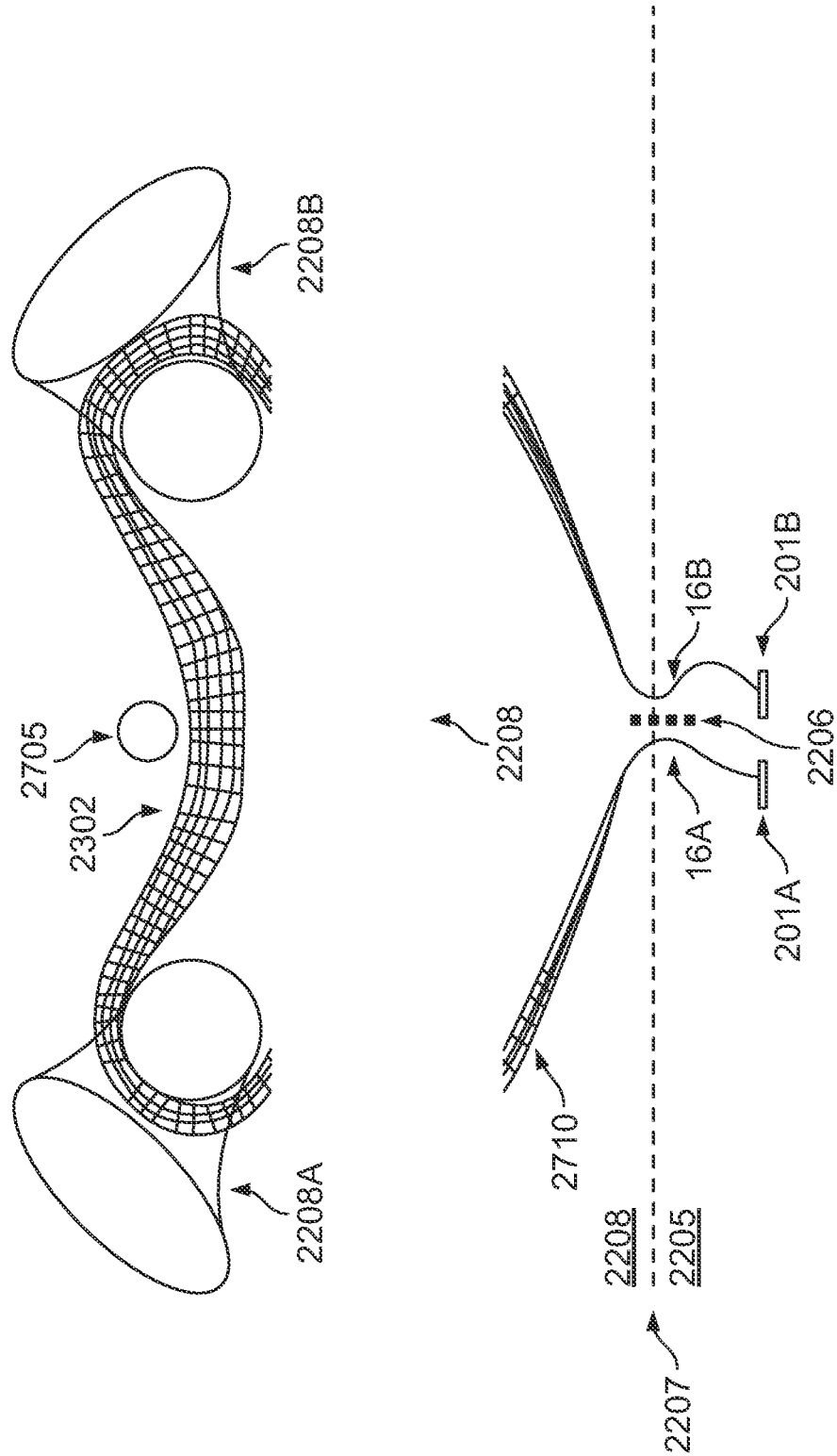

As shown in FIG. 27F, in some embodiments, the excess portion 2710, which can include each excess end of the mesh 2302 attached to the thread 16A and thread 16B with the needle 201A and needle 201B, can be cut after positioning the mesh 2302. As shown in FIG. 27G, the mesh 2302 can be positioned in the pelvic cavity 2208A and 2208B after the excess portion 2710 containing the mesh 2302 attached to the thread 16A and thread 16B and the needle 201A and needle 201B attached thereof are cut off.

Figure 27H:
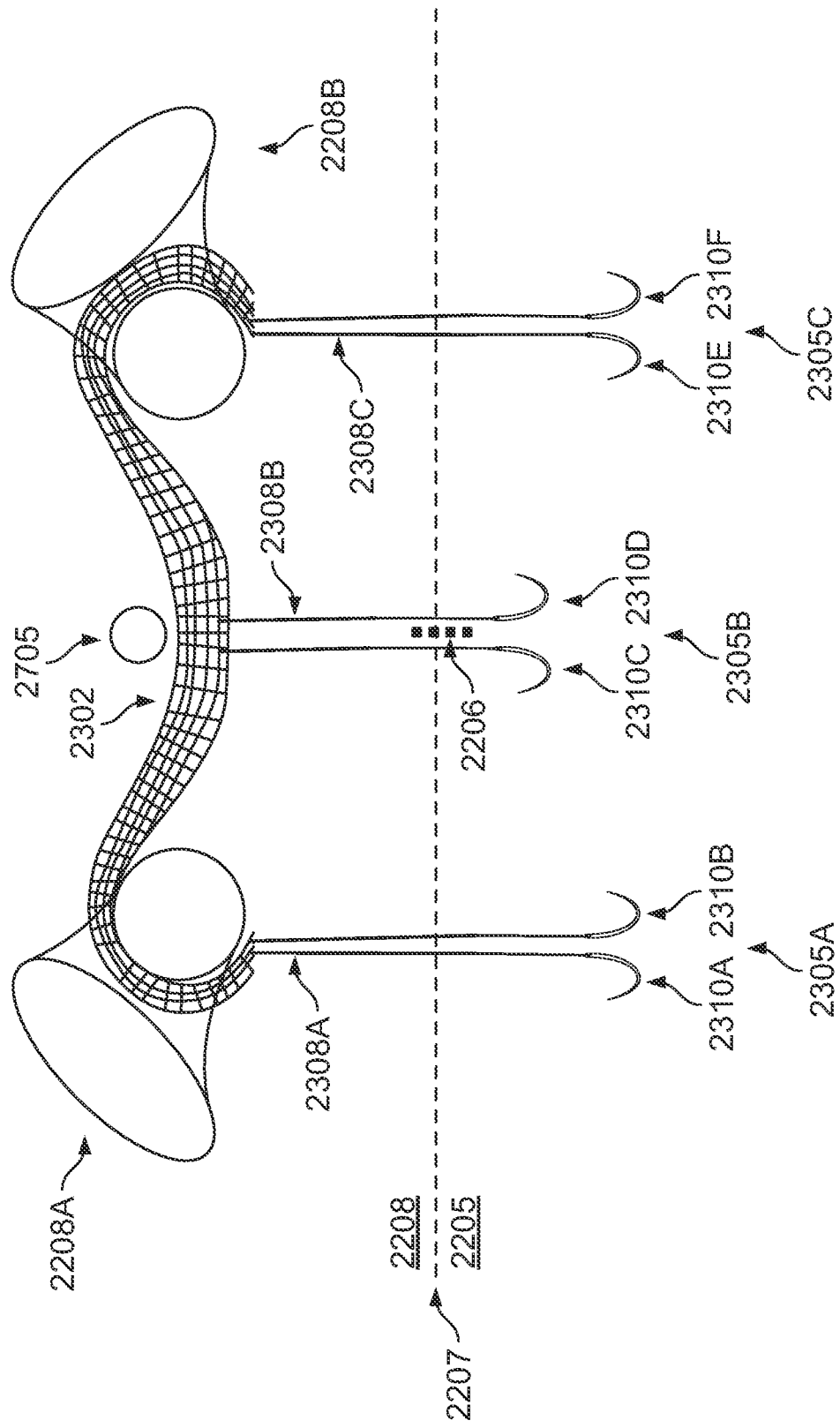

As shown in FIG. 27H, after positioning the mesh 2302, if the operator decides to have the post-operative adjustment, then during the operation, the operator can attach the adjustment sutures 2305A-2305C to the mesh 2302. For example, the operator can insert the adjustment sutures 2305A-2305C through the incision 2206 in the vagina. Each of the adjustment sutures 2305A-2305C can include curved needles 2310A-2310F attached to each end of the threads 2308A-2308C.

The operator can attach the adjustment suture 2305A and the adjustment suture 2305C towards ends of the mesh 2302 (e.g., points where the mesh 2302 was cut at each end) for tensioning the mesh 2302. In some embodiments, the curved needles of the adjustment suture 2305A and the adjustment suture 2305C can be inserted through the incision 2206 and then brought out by piercing the vaginal wall 2207 to bring them back into the vaginal cavity 2205. The operator can attach the adjustment suture 2305B in the middle of the mesh 2302 for loosening the mesh 2302.

In some embodiments, after the operator attaches the adjustment sutures 2305A-2305C to the mesh 2302, each end of the adjustment threads 2308A-2308C, which is attached to respective curved needles 2310A-2310F, can be brought into the vaginal cavity 2205 by piercing through the vaginal wall 2207 by the curved needles 2310A-2310F attached to each end of the adjustment thread 2308.

Figure 27I:
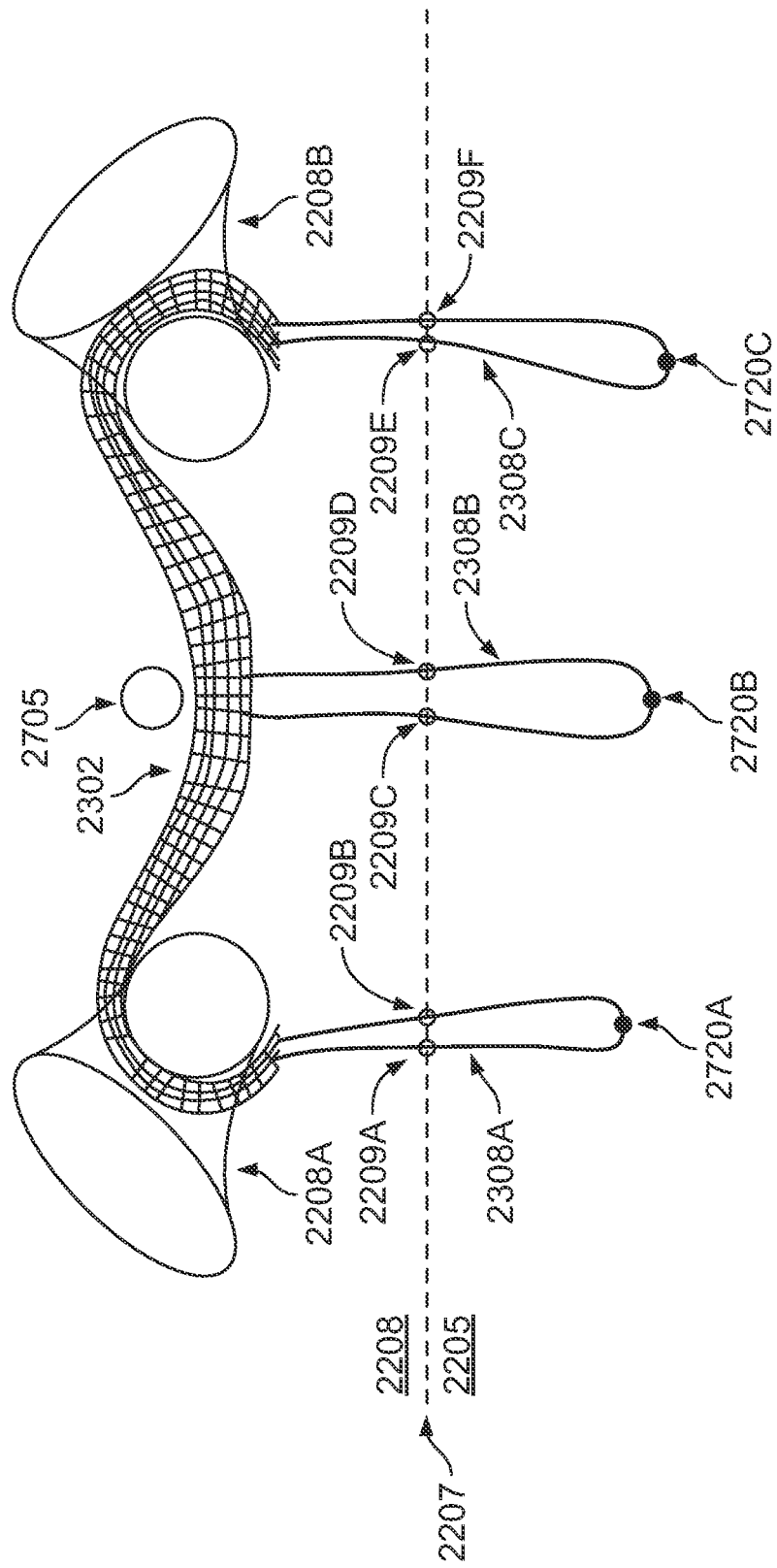

As shown in FIG. 27I, in some embodiments, the curved needles 2310A-2310F pierce through the vaginal wall 2207 at pierce points 2209A-2209F. For example, the 6 curved needles 2310A-2310F can create 6 pierce points 2209A-2209F through which the 6 ends of the 3 adjustment threads 2308A-2308C can be pulled out of the pelvic cavity 2208 and into the vaginal cavity 2205. The curved needles 2310A-2310F can be pulled to pull the adjustment sutures 2305A-2305C through the pierce points 2209A-2209F. For example, each of the adjustment threads 2308A-2308C has 2 ends with curved needles 2310A-2310F attached to both ends, and both ends of each of the adjustment threads 2308A-2308C can be brought to the vaginal cavity 2205 through the vaginal wall 2207.

As shown in FIG. 27I, the operator can cut off part of the threads 2308A-2308C to remove the curved needles 2310A-2310F from the operating site. In some embodiments, the curved needles 2310A-2310F can be brought out from the outside of the incision 2206 (e.g., not through the incision 2206) by piercing through the vaginal wall 2207 to be removed by cutting the curved needles 2310A-2310F. For example, the mesh 2302 can be left positioned relative to the urethra 2705 and the curved needles 2310A-2310C attached thereof can be cut off.

After the curved needles 2310A-2310F are cut off, the operator can make knots 2720A-2720C of the threads 2308A-2308C at their respective ends. The operator can use the knots 2720A-2720C to adjust the tension of the mesh 2302 because the remaining threads 2308A-2308C remain attached to the mesh 2302. The operator can cut the curved needles 2310A-2310F off and make knots 2720A-2720C of the remaining threads 2308 to form a loop and secures the knots 2720A-2720C in the housings 2725A-2725C. The knots 2720A-2720C, the threads 2308, and the housings 2725 do not stick out of the vagina. For example, during the post-operative period, the patient does not see them because they stay in the vaginal cavity 2205.

Figure 27J:
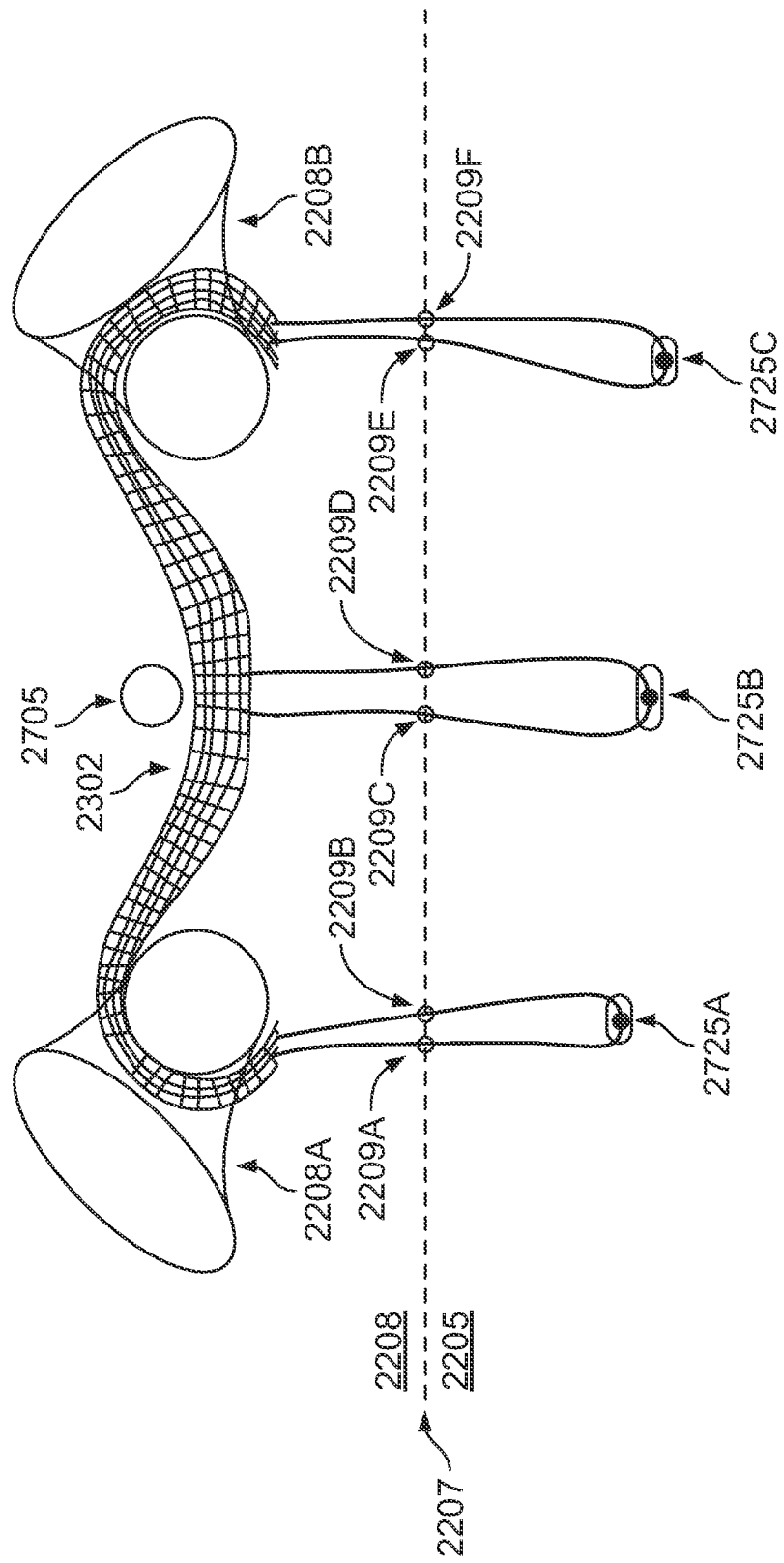

As shown in FIG. 27J, the knots 2720A-2720C can be stored in housings 2725A-2725C. The housings 2725A-2725C can be containers or enclosures for the knots 2720A-2720C. The housings 2725A-2725C can be used to secure the knots 2720A-2720C in the vaginal cavity 2205 of the patient after the operation until the patient's post-operative check-up for adjustment. The housings 2725A-2725C can keep the knots 2720A-2720C intact and keep them from contamination during this period of time. By maintaining the knots 2720A-2720C in the housings 2725A-2725C, the operator can adjust the tension of the mesh 2302 relative to the urethra 2705 after the procedure. For example, the knots 2720A-2720C can be kept in the housings 2725A-2725C for one week following the operation, in case adjustment of the mesh 2302 is needed. In another example, one week after the operation, the patient may report difficulty voiding or incontinence, and both can be remedied by adjusting the tension of the mesh 2302 relative to the urethra 2705. After the tension is readjusted post-operatively, the adjustment sutures 2305A-2305C can be cut off and taken away from the mesh 2302. This possibility of adjusting the mesh 2302 after the operation is advantageous by avoiding the need for a second operation to reinsert the mesh 2302 or additional adjustments sutures.

After the operation (e.g., 1 week), when the operator checks the patient for adjustment, the operator reaches the knots 2720A-2720C secured in the housings 2725 in the vaginal cavity 2205 of the patient and adjusts the tension of the mesh 2302. For example, this adjustment can be done after the operation, does not require a new operation, and can be done in the outpatient clinic or office set up. The operator can pull the knots 2720A-2720C to pull the threads 2308A-2308C attached to the mesh 2302.

In some embodiments, at the post-operative check-up done in office setting or outpatient clinic, the operator can pull on the knots 2720A-2720C of the adjustment suture 2305A and the adjustment suture 2305C to pull the mesh 2302 towards the urethra 2705 to tighten the mesh 2302. For example, the operator can pull on the knots 2720A-2720C secured in the housings 2725A-2725C of the adjustment suture 2305A and of the adjustment suture 2305C to pull the mesh 2302 towards the urethra 2705 to tighten the mesh 2302. In some embodiments, the operator can pull the knots 2720A and 2720C to increase the tension of the mesh 2302.

For example, the knots 2720A and 2720C on the sides of the mesh 2302 can be used for increasing the tension after the operation. The operator can pull the knots 2720A and 2720C at the edges to pull the mesh 2302 towards the urethra 2705 to tighten the mesh 2302.

In some embodiments, the operator can pull the knot 2720B to loosen the mesh 2302. The operator can pull the knot 2720B in the middle to pull the mesh 2302 away from the urethra 2705 to loosen the mesh 2302. In some embodiments, the operator can pull on the knot 2720B secured in the housing 2725B of the adjustment suture 2305B to pull the mesh 2302 away from the urethra 2705 to loosen the mesh 2302. For example, the operator can pull on the knot 2720B secured in the housing 2725B of the adjustment suture 2305B in the middle of the mesh 2302 to pull the mesh 2302 away from the urethra 2705 to loosen the mesh 2302. After the operator completes the adjustment, the operator can cut the loop, discard the housings 2725, and pull on the adjustment thread 2308 to take the thread away.

Now referring generally to the suturing device 1A and the suturing device 1B. The suturing devices can be used for pelvic floor disorders' treatment, such as the treatment of SUI and POP. For example, the suturing devices can be angled for transvaginal approaches or procedures. In another example, the suturing devices can be a minimally invasive operation device of the vaginal wall or uterine prolapse in women. The suturing devices can include various sizes, shapes, and angles calculated and optimized based on the pelvis anatomy for which the suturing device is to be used. The optimal size and shape enable the suturing devices to safely access target tissues for each device for their specified surgeries. The angled design of the suturing devices enables the tip of the devices to reach the target pelvic structures to be sutured via vaginal route. The angled design and sizes prevent unintended contact with other tissues. The shape of the suturing devices can improve performance and provides safety and ease of reach to target tissues by preventing unintended tissue injuries. The suturing devices can be minimally invasive, disposable, sterile, and for single use.

The suturing devices can be a transvaginal device to place sutures in tissues at the operative site during the pelvic floor surgery in women (e.g., to treat stress urinary incontinence or pelvic organ prolapse, which is the bulging of pelvic organs such as bladder, rectum and uterus into the vagina and past the vaginal opening). The suturing devices can be transvaginal devices used with a single incision, which can be advantageous over abdominal and a plurality of incisions. The suturing devices can be used for consistent placement of sutures in difficult to access locations, such as those that are narrow and not visible. The suturing devices can be a one-step suturing device with an operating mechanism that enables the needle to be caught safely at the opposite jaw.

The suturing devices can suture the specified ligament to vesicovaginal fascia at the level of bladder neck to elevate the bladder outlet to its normal position. The suturing devices can be ergonomic and shaped to perform the vaginal native tissue repair procedure for stress urinary incontinence. The suturing devices can be designed for the surgical treatment of stress urinary incontinence in women to facilitate the consistent placement of sutures in difficult to access locations (narrow and not visible). The suturing devices can be designed for regaining anterior vaginal support or vaginal colposuspension procedure. The suturing devices can be used in difficult to access general suturing applications during urogynecological procedures, including but not limited to stress urinary incontinence procedures, to assist in the placement of sutures at the operative site.

The suturing devices can enable the operator to perform surgery via the vagina (e.g., transvaginal route as opposed to abdominal operations) in a minimally invasive way (e.g., single vaginal incision only). The suturing devices can be used for single vaginal incision native tissue repair via stitching vaginal wall to the pelvic floor supportive structures (to assist the placement of sutures in ligaments on to the pelvic floor supportive structures). The suturing devices can be used by an operator (e.g., surgeon) with sensory and/or direct visual control. The suturing device can be designed to enable the operator to perform a native tissue repair, without the placement of an artificial implant (as opposed to mid-urethral sling technique which requires the placement of a synthetic sling/mesh or transvaginal mesh operations).

The suturing devices can be designed to be safely inserted into the cavity. The safety of the suturing devices can be derived from the length of the suturing devices. For example, the lengths (of the arms 7 and 8 and jaws 5 and 6) and angles of the suturing devices can contribute to safety outcomes described herein, and as such the lengths and angles can be designed to not damage the vagina or the incision. In another example, because the entrance point of the suturing device into the body is through the vagina but the entrance to the operating site is through the incision which is opened at the wall of the vagina, the operator can insert the suturing device into the pelvic cavity where the ATFP is located. For example, for stress incontinence operations done with the suturing device, the suturing device does not need to be inserted beyond the ATFP, which is the anatomical landmark used to determine the length of the suturing device. Even if the suturing device is positioned in the vagina past the arm joint 101, the length of the suturing devices enables the widening of the suturing device caused by the opening of the handle to not affect the incision.

The suturing devices can facilitate the consistent and sequential placement of sutures (e.g., making multiple sutures with the same needle; also called Z-suture or 8-figure suture) onto the pelvic floor structures, which are in difficult to access locations during pelvic floor surgery. The suturing devices can be designed to facilitate the consistent placement of sutures in difficult to access locations (deep, narrow, and not visible operating site) during transvaginal prolapse surgery (as opposed to abdominal surgery). The suturing devices can suture the specified ligament to the apical vaginal wall or cervix uteri in order to provide vaginal apex elevation.

The suturing devices can be used for a transvaginal minimally invasive procedure. The suturing devices can be designed for vaginal wall or uterine prolapse surgery based on native tissue repair in women with pelvic organ prolapse (sagging of pelvic organs such as bladder, uterus or bowel into the vagina). The suturing devices can be designed to enable the operator to perform a native tissue repair, without the placement of an artificial implant (as opposed to operations requiring the placement of synthetic mesh). The suturing devices can enable operators to perform surgery via the vagina in a minimally invasive way, such as with just a single incision. The suturing devices can be used in difficult to access general suturing applications during urogynecological procedures, including but not limited to transvaginal pelvic organ prolapse procedures, to assist in the placement of sutures at the operative site. The suturing devices can be used with sensory and/or direct visual control.

The suturing devices 1A and 1B can be used for the positioning of the tension-free single incision mid-urethral sling (mini sling 2300) whose tension can be adjusted post-operatively.

While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added, and/or any desired steps may be eliminated).

What is claimed is:

1. A loading apparatus comprising:
    a base;
    a first loading slot disposed on the base, the first loading slot configured to receive a first arm of a suturing apparatus;
    a suture housing disposed on the base and configured to house a suture; and
    a slider configured to hold a needle coupled to the suture, the slider being slidable on the base from a neutral position away from the first loading slot toward the first loading slot to a first insertion position to insert the needle into the first arm.

2. The loading apparatus of claim 1, wherein the first loading slot comprises one or more side walls that are sized and angled to securely fit the first arm into the first loading slot.

3. The loading apparatus of claim 1, further comprising a fixing wall configured to maintain an end of a first arm in the first loading slot while receiving the needle.

4. The loading apparatus of claim 1, further comprising a second loading slot disposed on the base away from the first loading slot, the second loading slot configured to receive a second arm of a suturing apparatus.

5. The loading apparatus of claim 4, wherein the slider is further configured to slide toward the second loading slot to a second insertion position to insert the needle into the second arm.

6. The loading apparatus of claim 4, wherein the second loading slot comprises one or more side walls that are sized and angled to securely fit the second arm into the second loading slot while the first arm is in the first loading slot.

7. The loading apparatus of claim 1, wherein the suture housing comprises a rotatable pulley, wherein the rotatable pulley is configured to rotate in a first direction to release the suture when the slider slides between the neutral position and the first insertion position or a second insertion position.

8. The loading apparatus of claim 7, wherein the rotatable pulley is configured such that rotation of the rotatable pulley in a second direction winds the suture for the needle to be loaded back into rotatable pulley after being loaded to the suturing apparatus.

9. The loading apparatus of claim 1, wherein the slider comprises a slot sized to receive and secure the needle.

10. The loading apparatus of claim 1, further comprising a loading channel, the loading channel defining a space within which the slider can move, and wherein the loading channel is sized so that the slider slides within the loading channel but does not fall out of the loading channel.

11. The loading apparatus of claim 10, wherein the slider comprises at least one safety notch in the loading channel and at least one protrusion on the slider for informing an operator that the needle has been loaded.

12. The loading apparatus of claim 1, wherein the suture is preloaded into the suture housing.

13. The loading apparatus of claim 1, wherein the needle comprises at least one notch configured to be grasped by a grasping slot of the first arm.

14. A loading apparatus comprising:
    a base;
    a first loader disposed on the base, the first loader comprising:
        a first loading slot configured to receive a first arm of a first suturing apparatus; and
        a first slider configured to hold a first needle coupled to a first suture, the first slider being slidable on the base from a first neutral position away from the first loading slot toward the first loading slot to a first insertion position to insert the needle into the first arm; and
    a second loader disposed on the base away from the first loader, the second loader comprising:
        an opposing first loading slot configured to receive a first arm of a second suturing apparatus; and
        a second slider configured to hold a second needle coupled to a second suture, the second slider being slidable on the base from a second neutral position away from the opposing first loading slot toward the opposing first loading slot to a second insertion position to insert the second needle into the first arm of the second suturing apparatus.

15. The loading apparatus of claim 14, wherein the first slider is symmetrically positioned relative to the second slider.

16. The loading apparatus of claim 14, wherein each of the first suture and the second suture is connected to a mesh.

17. The loading apparatus of claim 16, wherein the mesh is one or more of adjustable and tension-free.

18. The loading apparatus of claim 16, wherein the mesh comprises a rectangular shape with tapered edges.

19. The loading apparatus of claim 16, wherein the mesh comprises one or more adjustment sutures.

* * * * *